(12) United States Patent
Join et al.

(10) Patent No.: US 11,434,220 B2
(45) Date of Patent: Sep. 6, 2022

(54) USE OF PHYSIOLOGICAL COOLING ACTIVE INGREDIENTS, AND COMPOSITIONS COMPRISING SUCH ACTIVE INGREDIENTS

(71) Applicants: BASF SE, Ludwigshafen am Rhein (DE); SYMRISE AG, Holzminden (DE)

(72) Inventors: Benoît Join, Holzminden (DE); Jekaterina Ongouta, Stadtoldendorf (DE); Michael Backes, Holzminden (DE); Rahim Brodhage, Höxter (DE); Arnold Machinek, Holzminden (DE); Hubert Loges, Höxter (DE); Susanne Mundt, Holzminden (DE); Tom Somers, Holzminden (DE); Thomas Subkowski, Schriesheim (DE); Jens Wittenberg, Limburgerhof (DE); Martin Weisel, Mannheim (DE); Wolfgang Siegel, Limburgerhof (DE); Claus Bollschweiler, Heidelberg (DE); Ralf Pelzer, Fürstenberg (DE)

(73) Assignees: BASF SE, Ludwigshafen am Rhein (DE); SYMRISE AG, Holzminden (DE)

(*) Notice: Subject to any disclaimer, the term of this patent is extended or adjusted under 35 U.S.C. 154(b) by 0 days.

(21) Appl. No.: 16/642,954

(22) PCT Filed: Aug. 31, 2018

(86) PCT No.: PCT/EP2018/073486
§ 371 (c)(1),
(2) Date: Feb. 28, 2020

(87) PCT Pub. No.: WO2019/043164
PCT Pub. Date: Mar. 7, 2019

(65) Prior Publication Data
US 2020/0190052 A1 Jun. 18, 2020

(30) Foreign Application Priority Data
Aug. 31, 2017 (EP) .................................... 17188719

(51) Int. Cl.
| | |
|---|---|
| *C07D 317/46* | (2006.01) |
| *C07C 323/41* | (2006.01) |
| *C07D 405/12* | (2006.01) |
| *C07D 213/75* | (2006.01) |
| *C07D 231/40* | (2006.01) |
| *C07D 407/12* | (2006.01) |
| *C07D 307/14* | (2006.01) |
| *C07D 409/12* | (2006.01) |
| *C07D 409/14* | (2006.01) |

(Continued)

(52) U.S. Cl.
CPC ............ *C07D 317/46* (2013.01); *A23G 3/36* (2013.01); *A23L 27/88* (2016.08); *A23L 29/035* (2016.08); *A23L 29/045* (2016.08); *A23L 29/055* (2016.08); *A61K 8/46* (2013.01); *A61K 8/494* (2013.01); *A61K 8/4926* (2013.01); *A61K 8/4973* (2013.01); *A61K 8/4986* (2013.01); *A61Q 11/00* (2013.01); *C07C 323/41* (2013.01); *C07D 213/75* (2013.01); *C07D 231/40* (2013.01); *C07D 307/14* (2013.01); *C07D 405/12* (2013.01); *C07D 405/14* (2013.01); *C07D 407/12* (2013.01); *C07D 409/12* (2013.01); *C07D 409/14* (2013.01); *A23V 2002/00* (2013.01)

(58) Field of Classification Search
CPC .. C07D 317/46; C07D 213/75; C07D 231/40; C07D 307/14; C07D 405/12; C07D 405/14; C07D 407/12; C07D 409/12; C07D 409/14; A23L 27/88; A23L 29/035; A23L 29/055; A23L 29/045; A23G 3/36; A61K 8/46; A61K 8/4926; A61K 8/494; A61K 8/4973; A61K 8/4986; A61Q 11/00; C07C 323/41; A23V 2002/00
See application file for complete search history.

(56) References Cited

U.S. PATENT DOCUMENTS

| | | | |
|---|---|---|---|
| 771,114 | A | 9/1904 | Andriano et al. |
| 2,973,282 | A | 2/1961 | Gross |

(Continued)

FOREIGN PATENT DOCUMENTS

| | | | |
|---|---|---|---|
| CA | 2066226 | A1 | 3/1991 |
| CA | 2140920 | A1 | 3/1994 |

(Continued)

OTHER PUBLICATIONS

"Bioisosteric Replacements: Ring Replacements," from Cambridge MedChem Consulting, downloaded Sep. 8, 2020 from https://www.cambridgemedchemconsulting.com/resources/bioisoteres/ring_bioisosteres.html, copyright 2012. (Year: 2012).*

(Continued)

*Primary Examiner* — Michael P Cohen
(74) *Attorney, Agent, or Firm* — Faegre Drinker Biddle & Reath LLP

(57) ABSTRACT

The invention relates primarily to a method of modulation, preferably of in vitro and/or in vivo modulation, of the cold menthol receptor TRPM8, wherein the receptor is contacted with at least one modulator selected from the group consisting of the compounds of the structure type 1 described herein. The present invention further relates to corresponding uses and compositions comprising such compounds.

16 Claims, No Drawings

(51) Int. Cl.
  *C07D 405/14* (2006.01)
  *A61K 8/49* (2006.01)
  *A61K 8/46* (2006.01)
  *A61Q 11/00* (2006.01)
  *A23L 29/00* (2016.01)
  *A23L 27/00* (2016.01)
  *A23G 3/36* (2006.01)

(56) References Cited

U.S. PATENT DOCUMENTS

| | | | |
|---|---|---|---|
| 3,111,127 | A | 11/1963 | Jarboe |
| 3,307,544 | A | 3/1967 | Gander et al. |
| 4,237,253 | A | 12/1980 | Jacquet et al. |
| 4,262,003 | A | 4/1981 | Urquhart et al. |
| 4,497,800 | A | 2/1985 | Larson et al. |
| 4,514,231 | A | 4/1985 | Kerner et al. |
| 4,670,268 | A | 6/1987 | Mahmoud |
| 4,814,101 | A | 3/1989 | Schieferstein et al. |
| 4,900,566 | A | 2/1990 | Howard |
| 4,921,694 | A | 5/1990 | Hoppe et al. |
| 5,104,677 | A | 4/1992 | Behr et al. |
| 5,223,285 | A | 6/1993 | DeMichele et al. |
| 5,266,592 | A | 11/1993 | Grub et al. |
| 5,318,778 | A | 6/1994 | Schmucker et al. |
| 5,389,395 | A | 2/1995 | Joseph et al. |
| 5,648,067 | A | 7/1997 | Dillenburg et al. |
| 5,703,123 | A | 12/1997 | Pelzer et al. |
| 5,718,887 | A | 2/1998 | Wolf et al. |
| 5,718,888 | A | 2/1998 | Klier et al. |
| 5,725,865 | A | 3/1998 | Mane et al. |
| 5,752,529 | A | 5/1998 | Mane et al. |
| 5,843,466 | A | 12/1998 | Mane et al. |
| 5,880,252 | A | 3/1999 | Kim et al. |
| 5,895,643 | A | 4/1999 | Hoppe et al. |
| 6,893,626 | B2 | 5/2005 | Wei |
| 8,710,096 | B2 * | 4/2014 | Subkowski .......... A61K 8/4953 514/449 |
| 8,927,605 | B2 * | 1/2015 | Subkowski ............. A23L 33/10 514/617 |
| 9,346,823 | B2 * | 5/2016 | Subkowski ............. A61Q 5/02 |
| 10,492,511 | B2 | 12/2019 | Kulke et al. |
| 2002/0137978 | A1 | 9/2002 | Grubbs et al. |
| 2002/0165168 | A1 | 11/2002 | Bunger et al. |
| 2003/0207904 | A1 | 11/2003 | Wei |
| 2004/0028714 | A1 | 2/2004 | Blondeau et al. |
| 2004/0067970 | A1 | 4/2004 | Foster et al. |
| 2004/0132730 | A1 | 7/2004 | Axon et al. |
| 2005/0000529 | A1 | 1/2005 | Bereman et al. |
| 2005/0084447 | A1 | 4/2005 | Wei |
| 2005/0222256 | A1 | 10/2005 | Erman et al. |
| 2005/0267089 | A1 | 12/2005 | Wang et al. |
| 2008/0027029 | A1 | 1/2008 | Colburn et al. |
| 2008/0241872 | A1 | 10/2008 | Julius et al. |
| 2008/0242841 | A1 | 10/2008 | Julius et al. |
| 2009/0163545 | A1 | 6/2009 | Goldfarb |
| 2011/0145970 | A1 * | 6/2011 | Subkowski .......... A61K 8/4953 2/69 |
| 2012/0202806 | A1 | 8/2012 | Duerrenberger et al. |
| 2012/0263659 | A1 | 10/2012 | Subkowski et al. |
| 2015/0086491 | A1 | 3/2015 | Subkowski et al. |
| 2016/0317532 | A1 | 11/2016 | Priest et al. |
| 2017/0096418 | A1 | 4/2017 | Patron et al. |

FOREIGN PATENT DOCUMENTS

| | | |
|---|---|---|
| CH | 651445 A5 | 9/1985 |
| CN | 1048030 A | 12/1990 |
| CN | 102137660 A | 7/2011 |
| DE | 442946 C | 4/1927 |
| DE | 2150557 A1 | 6/1972 |
| DE | 2608226 A1 | 9/1977 |
| DE | 2817369 A1 | 10/1978 |
| DE | 2837851 A1 | 3/1980 |
| DE | 3314742 A1 | 10/1984 |
| DE | 3708451 A1 | 10/1988 |
| DE | 3740186 A1 | 1/1989 |
| DE | 3807283 A1 | 9/1989 |
| DE | 3929973 A1 | 3/1991 |
| DE | 3938140 A1 | 8/1991 |
| DE | 4035378 A1 | 5/1992 |
| DE | 4204321 A1 | 8/1993 |
| DE | 4226043 A1 | 2/1994 |
| DE | 4229707 A1 | 3/1994 |
| DE | 4229737 A1 | 3/1994 |
| DE | 4237081 A1 | 5/1994 |
| DE | 4309372 A1 | 9/1994 |
| DE | 4324219 A1 | 1/1995 |
| DE | 4333238 A1 | 4/1995 |
| DE | 4411664 A1 | 10/1995 |
| DE | 4423410 A1 | 1/1996 |
| DE | 19516705 A1 | 11/1996 |
| DE | 19541967 A1 | 5/1997 |
| DE | 19543695 A1 | 5/1997 |
| DE | 19543696 A1 | 5/1997 |
| DE | 19547160 A1 | 6/1997 |
| DE | 16202110 A1 | 7/1997 |
| DE | 19602108 A1 | 7/1997 |
| DE | 19602111 A1 | 7/1997 |
| DE | 19631003 A1 | 2/1998 |
| DE | 19631004 A1 | 2/1998 |
| DE | 19634019 A1 | 2/1998 |
| DE | 19810951 A1 | 9/1999 |
| DE | 19919816 A1 | 11/2000 |
| EP | 0186071 A2 | 7/1986 |
| EP | 0392608 A2 | 10/1990 |
| EP | 0507190 A1 | 10/1992 |
| EP | 1710345 A1 | 10/2006 |
| EP | 1913976 A1 | 4/2008 |
| EP | 1958627 A2 | 8/2008 |
| EP | 2033688 A2 | 3/2009 |
| EP | 2250998 A1 | 11/2010 |
| EP | 03015121 A1 | 5/2016 |
| GB | 1315761 A | 5/1973 |
| GB | 1368495 A | 9/1974 |
| JP | 54-112882 A | 9/1979 |
| JP | 02-122979 A | 5/1990 |
| JP | 05-125073 A | 5/1993 |
| JP | 2004059474 A | 2/2004 |
| JP | 2004-510699 A | 4/2004 |
| JP | 2005343795 A | 12/2005 |
| JP | 2006-503043 A | 1/2006 |
| JP | 2006-512294 A | 4/2006 |
| JP | 2007-532669 A | 11/2007 |
| JP | 2009-536668 A | 10/2009 |
| JP | 2014-153389 A | 8/2014 |
| RO | 0122199 B1 | 2/2009 |
| RU | 704083 | 10/1993 |
| RU | 704083 C | 10/1993 |
| SU | 636236 A1 | 12/1978 |
| SU | 0776048 A1 | 9/1983 |
| SU | 704082 A1 | 10/1989 |
| WO | 99/56548 A1 | 11/1999 |
| WO | 02/00590 A1 | 1/2002 |
| WO | WO-2002015692 A1 | 2/2002 |
| WO | WO-2004000023 A1 | 12/2003 |
| WO | 2004/024159 A1 | 3/2004 |
| WO | WO-2004026840 A1 | 4/2004 |
| WO | 2005/099711 A1 | 10/2005 |
| WO | 2006/040136 A1 | 4/2006 |
| WO | 2006/069258 A1 | 6/2006 |
| WO | 2007/017093 A1 | 2/2007 |
| WO | WO-2007019719 A1 | 2/2007 |
| WO | 2007/048265 A1 | 5/2007 |
| WO | 2007/073505 A2 | 6/2007 |
| WO | 2008/015403 A1 | 2/2008 |
| WO | 2008/129258 A1 | 10/2008 |
| WO | 2009/012430 A1 | 1/2009 |
| WO | 2009/064388 A2 | 5/2009 |
| WO | 2009/099193 A1 | 8/2009 |
| WO | 2010/010435 A2 | 1/2010 |
| WO | WO-2010026094 A1 | 3/2010 |

(56) References Cited

FOREIGN PATENT DOCUMENTS

| WO | 2011/026835 A1 | 3/2011 |
|---|---|---|
| WO | WO-2011061330 A2 | 5/2011 |
| WO | WO-2014090293 A1 | 6/2014 |

OTHER PUBLICATIONS

Google Search—TRPM8 modulators Feb. 12, 2021 (Year: 2021).*
G.Ali, et al. Input of Isosteric and Bioisosteric Approach in Drug Design. J. Chem. Soc. Pak., vol. 36, No. 1, 2014, 150-169. (Year: 2014).*
European Search Report for EP17188719.3 dated Feb. 29, 2018.
International Preliminary Report on Patentability for PCT/EP2018/073486 dated Oct. 31, 2018.
Akgul et al., "3,4-Dimethoxycinnamic acid tertiary amides: synthesis and evaluation of antiinflammatory and analgesic activities", Farmaco, societa chimica italiana, pavia, IT, vol. 51, No. 8-9, Jan. 1, 1996, pp. 595-599.
Akhrem et al., "Heterocyclic steroid analogs. XIV. Synthesis and some properties of conjugated enamino lactones of the 8-aza-16-oxa steroid series", Zhurnal Organicheskoi Khimii, vol. 21, No. 6, 1348-1354.
Akhrem et al., Heterocyclic steroid analogs XIV. Synthesis and some properties of conjugated enamino lactones of the 8-aza-16-oxa steroid series, Chemical Abstracts, vol. 054, No. 01, 1986, XP002616827.
Andersson et al., "TRPM8 Activation by Menthol, Icilin, and Cold Is Differentially Modulated by Intracellular pH", Journal of Neuroscience, vol. 24, No. 23, Jun. 9, 2004, pp. 5364-5369.
Behrendt H-J et al: Characterization of the mouse cold-menthol receptor TRPM8 and vanilloid receptor type-1 VRI using a fluorometric imaging plate reader (FLIPR) assay 11, British Journal of Pharmacology, Wiley-Blackwell, UK, Bd. 141, Nr. 4, Feb. 1, 2004 (Feb. 1, 2004), Seiten 737-745.
Chen et al., "Inhibitors of Plasmodium falciparum methionine aminopeptidase 1 b possess antimalariai activity," Proceedings of the National Academy of Sciences of the United States of America, 2006, vol. 103, No. 39, p. 14548-14553.
Chinese Office Action dated Feb. 11, 2019 for corresponding Chinese Application No. 201080061894.5 and English translation.
Chinese Office Action dated Feb. 14, 2018 for corresponding Chinese Application No. 201080061894.5 and English translation thereof.
Chinese Office Action issued in parallel Chinese Application No. 201080061894.5, dated Dec. 9, 2016.
Chinese Office Action issued in parallel Chinese Application No. CN102844386A along with (English Translation), dated Aug. 25, 2016.
Chinese Office Action, issued in Chinese Application No. 201080061894.5, along with the English Translation of the Office Action, dated Apr. 8, 2015.
Database WPI Week 198406 Thomson Scientific, London, GB; AN 1984-035077, XP002616829.
Database WPI, Week 199026 Thomson Scientific, London, GB; AN 1990-199211, XP002616831.
Database WPI, Week 197937 Thomson Scientific, London, GB; AN 1979-67490B, XP002617232.
Database WPI, Week 199409 Thomson Scientific, London, GB; AN 1994-073464, XP002616830.
Doherty Elizabeth M et al: "Discovery of potent, orally available vanilloid receptor-1 antagonists. Structure-activity relationship of N-aryl cinnamides", Journal of Medicinal Chemistry, American Chemical Society, Bd. 48, Nr. 1, Jan. 13, 2005, Seiten 71-90, XP002408838, ISSN: 0022-2623, DOI: DOI:10.1021/JM049485I.
Elizabeth et al., "Discovery of potent, orally available vanilloid receptor-1 antagonists. Structure-activity relationship of N-aryl cinnamides", Journal of Medicinal Chemistry, vol. 48, No. 1, Jan. 13, 2005, pp. 71-90.
English translation of Office Action issued in parallel JP Application No. 2012-539353, dated Oct. 7, 2014.

English translation of the Chinese Office Action issued in parallel Chinese Application No. 201080061894.5, dated Dec. 9, 2016.
European Examination Report, European Application No. 10787717.7, received on Apr. 29, 2013.
European Office Action, European Application No. 10 787 717.7, received on Jan. 22, 2015.
German Examination Report, German Application No. 10 2010 002 558.5, received on Jul. 13, 2012.
Gulyakevich et al., "Synthesis and properties of dithioacetals of conformationally restricted 8-azasteroid .alpha.-acyl-.beta.-aminovinyl ketones", Chemical Abstracts, vol. 054, No. 01, 1995, XP002616826.
Gulyakevich et al., Synthesis and properties of dithioacetals of conformationally restricted 8-azasteroid alpha.-acyl-.beta.-aminovinyl ketones, Khimiya Geterotsiklicheskikh Soedinenii, (2), 1995, 187-94.
Indian Journal of Chemistry, 2008, vol. 47B, p. 1559-1567.
International Preliminary Reporton Patentability received for PCT Patent Application No. PCT/EP2010/067936, dated May 31, 2012, 56 pages (33 pages of English Translation and 23 pages of Original Document).
International Preliminary Report on Patentability received for PCT Patent Application No. PCT/EP2018/073486, dated Aug. 8, 2019, 37 pages (5 pages of English Translation and 32 pages of Original Document).
International Search Report and Written Opinion received for PCT Patent Application No. PCT/EP2010/067936, dated May 30, 2011, 70 pages (36 pages of English Translation and 34 pages of Original Document).
International Search Report with references cited and Written Opinion under Rule 43 PCT, attached to Search Report, PCT Application No. PCT/EP2010/067936, filed Nov. 22, 2010.
Japanese Office Action issued in parallel JP Application No. 2012-539353, dated Mar. 15, 2016, along with the English translation of the Japanese Office Action.
Japanese Office Action issued in parallel JP Application No. 2015-078665, dated Feb. 9, 2016, along with the English translation of the Japanese Office Action.
Japanese Office Action issued in parallel JP Application No. 2015-078666, dated Mar. 8, 2016, along with the English translation of the Japanese Office Action.
Kuz et al., "8,16-Diheterosteroids as immunomodulators", Studies in Organic Chemistry, vol. 18, No. Bio-Org. Heterocycl, Jan. 1, 1984, pp. 385-388.
Meeteren et al., "Ring Transformations in Reactions of Heterocyclic Halogeno Compounds with Nucleophiles (XX)," Recueil des Travaux Chimiques des Pays-Bas, 1971, vol. 90, p. 105-116.
Mikhal'chuk et al., "Dithiolene derivative of 8-aza-D-homogona-1,3,5(10),13-tetraene-12 17a-dione", XP002616864.
Sirisoma, et al., "Discovery of substituted 4-anilino-2-arylpyrimidines as a new series of apoptosis inducers using a cell- and caspase-based high throughput screening assay. 2. Structure-activity relationships of the 2-aryl group," Bioorganic & Medicinal Chemistry Letters, Feb. 2009, vol. 19, p. 2305-2309.
Tetrahedron Letters, 2000, vol. 41, p. 5761-5764.
Wei et al., AG-3-5: A Chemical Producing Sensations of Cold Journal of Pharmacy and Pharmacology, vol. 35, No. 2, Jan. 1, 1983, pp. 110-112.
X. Chen: "From the Cover: Inhibitors of Plasmodium falciparum methionine aminopeptidase lb possess antimalarial activity", Proceedings of the National Academy of Sciences, Bd. 103, Nr. 39, Sep. 14, 2006 (Sep. 14, 2006), Seiten 14548-14553.
Youval Shvo et al: "Chemical Shift Nonequivalence of Diastereotopic Protons Due to Restricted Rotation around Aryl-Nitrogen Bonds in Substituted Amides", Journal of the American Chemical Society, 89:19, Sep. 13, 1967, Jan. 1, 1967 (Jan. 1, 1967), Seiten 4910-4917.
Youval Shvo et al: "Chemical Shift Nonequivalence of Diastereotopic Protons Due to Restricted Rotation around Aryl-Nitrogen Bonds in Substituted Amides", Journal of the American Chemical Society, 89:19. Sep. 13, 1967, Jan. 1, 1967. Seiten 4910-4917, XP055059523,

(56) References Cited

OTHER PUBLICATIONS

Gefunden im Internet: URL: http://pubs.acs.org/doi/pdf/10.1021/ja00995a015 [gefunden am Apr. 15, 2013].

* cited by examiner

USE OF PHYSIOLOGICAL COOLING ACTIVE INGREDIENTS, AND COMPOSITIONS COMPRISING SUCH ACTIVE INGREDIENTS

CROSS-REFERENCE TO RELATED APPLICATIONS

This application is a national stage application (under 35 U.S.C. § 371) of PCT/EP2018/073486, filed Aug. 31, 2018, which claims benefit of European Application No. 17188719.3, filed Aug. 31, 2017, both of which are incorporated herein by reference in their entirety.

The invention relates primarily to novel modulators of the cold menthol receptor TRPM8, to methods of modulating the TRPM8 receptor using these modulators, to the use of the modulators for inducing a cold sensation, and to the compositions produced using these modulators.

In a specific aspect, the invention relates to a composition comprising at least one such modulator for achieving a cooling effect on the skin or mucosa, advantageously with a longer-lasting cooling effect compared to known cooling active ingredients (actives), for example to N-ethylmenthane-3-carboxamide (WS3), and/or an earlier onset of the cooling effect compared to known cooling actives, e.g. FEMA 4809 or FEMA 4496.

Moreover, a specific aspect of the invention relates to compositions comprising such selected TRPM8 receptor modulators, wherein the compositions serve particular purposes.

In addition, the invention also relates to a method of achieving a physiological cooling effect on the skin or mucosa, in which the compositions mentioned are used.

Further aspects of the present invention will be apparent from the description that follows, the examples and especially the appended claims.

Physiological cooling actives are used regularly in order to cause a cool sensory impression on the skin or mucosa, for example on the mucosa in the oral cavity, nasal cavity and/or pharyngeal cavity, even though no physical cooling as, for example, in the evaporation of solvents actually takes place. Physiological cooling actives used may be either individual components or mixtures. It should be taken into account here that not all compounds that influence receptors in vitro and are (also) involved in imparting a physiological cooling effect actually generate such an effect in vivo on the skin or mucosa. More particularly, such an effect will not always have an identical progression. This means, for example, that the intensity of the physiological cooling effect imparted and the progression of the intensity of the cooling effect over time cannot be concluded solely from the fact that a particular compound is an agonist of a receptor involved in the imparting of a cool impression.

The most widely known physiologically active cooling active is L-menthol, but it has some disadvantages, for example a strong odor impression, high volatility and, in relatively high concentrations, a bitter and/or sharp intrinsic taste, or an irritating effect on the skin.

There have therefore already been previous searches for strong cooling actives that do not have the disadvantageous properties of L-menthol. For example, there have been descriptions of lactic esters of menthol(s) in DE 2 608 226 and of mixed carbonates with menthol(s) and polyols in DE 4 226 043 and of menthone ketals in EP 0 507 190.

Menthyl monoesters of diacids according to U.S. Pat. Nos. 5,725,865 and 5,843,466 are naturally occurring alternatives of interest, but cannot achieve the intensity of the above-described cooling actives in sensory tests.

J. Soc. Cosmet. Chem. 1978, 29, 185-200 presented the results of a study on about 1200 compounds in which the compounds N-ethyl-L-menthanecarboxamide ("WS3") and especially $N^{\alpha}$-(L-menthanecarbonyl)glycine ethyl ester ("WS5") were found to be the strongest cooling actives. But the latter, while having a strong effect, has the disadvantage of being hydrolysisis-sensitive and forming the corresponding free acid $N^{\alpha}$-(L-menthanecarbonyl)glycine, which itself has only a very slight cooling effect. In spite of the detailed studies described, a systematic prediction of the properties of potential cooling actives, especially with regard to their bitterness and/or their other trigeminal effects is not possible, nor has it been described. For instance, many molecules within the class of the menthanecarboxamides also have a strong cooling effect, but frequently simultaneously have markedly bitter notes (e.g. the N-(alkyloxyalkyl)menthanecarboxamides according to JP 2004059474) or additionally have a strong irritant effect (WS5: N-[[5-methyl-2-(1-methylethyl)cyclohexyl]carbonyl]glycine ethyl ester, US 2005/0222256).

$N^{\alpha}$-(Menthanecarbonyl)alkyloxyalkylamides were described in JP 2004059474. While having a strong cooling effect and high hydrolysis stability, these have the disadvantage, however, of being highly bitter, and they are thus unusable in foods and also in cosmetic products for facecare purposes.

In addition, menthyl glyoxylates and their hydrates have been described as cooling substances in JP 2005343795.

Overviews of the cooling actives produced and used to date can be found in M. Erman, Perfumer & Flavorist 32(10), 20-35 (2007) and M. L. Dewis in D. J. Rowe, Chemistry and Technology of Flavors and Fragrances, Blackwell Publishing Ltd, Oxford 2005, p. 212-222.

The cold menthol receptor TRPM8 (also referred to as cold membrane receptor (CMR)1) belongs to the family of the transient receptor potential ion channels, is specifically expressed in a specific group of neurons and forms pores in the cell membrane (4 units in each case combine to form a tetramer) that selectively allow $Ca^{2+}$ ions to pass through. The protein has 6 transmembrane domains and a cytoplasmic C and N terminus. Low temperatures (preferably 10-25° C.) stimulate this receptor, resulting in signal transduction which is interpreted as a cold sensation by the nervous system. The receptor was described for the first time in 2002 as a cold receptor in multiple publications (Peier A M et al, A TRP channel that senses cold stimuli and menthol. Cell. 2002 Mar. 8; 108(5):705-15; McKemy D D et al. Identification of a cold receptor reveals a general role for TRP channels in thermosensation Nature 2002 Mar. 7; 416 (6876): 52-8; Zuker C S. Neurobiology: A cool ion channel Nature 2002 Mar. 7; 416 (6876): 27-8).

Cooling compounds, for example menthol, have already long played an important role in the flavorings and odorants industry in order to create an association with freshness and cleanliness. For the compound menthol, it has been shown that it acts as a natural modulator of the TRPM8 receptor (McKemy D. D., *Molecular Pain* 1, 2005, 16; McKemy D. D., *Nature* 416, 2002, 52-58; Peier A. M., Cell 108, 2002, 705-715; Dhaka A., *Annu. Rev. Neurosci* 29, 2006, 135-161). Application of menthol activates TRPM8, which brings about an influx of $Ca^{2+}$ into the cold-sensitive neurons. The resultant electrical signal is ultimately perceived as a cold sensation. Excessive menthol concentrations lead to irritation and an anesthetic effect. Furthermore, various publications have described menthol derivatives with a similar effect (British Patent 1971 #1315761 Watson H. R., *J. Soc. Cosmet. Chem.* 29, 1978, 185-200; Furrer S. M., *Chem. Percept.* 1, 2008, 119-126). There are also individual compounds structurally unrelated to menthol that bring about significant TRPM8 modulation, for example icilin (Wei E. T., *J. Pharm. Pharmacol.* 35, 1983, 110-112; WO 2004/026840), WS-23 or compounds detailed in patent application WO 2007/019719.

Further effects of substances that modulate the TRPM8 receptor or its insect analogs are a repellent effect on insects (WO 2002/015692; WO 2004/000023, US 2004/0028714), and activity in antitumor therapy (for example an influence on prostate tumors), activity in the treatment of inflammatory pain/hyperalgesia and an effect as TRPM8 antagonists in the treatment of bladder syndrome or overactive bladder (Beck B. *Cell Calcium,* 41, 2007, 285-294; Levine J. D. *Biochim. Biophys. Acta, Mol. Basis Dis.* 1772, 2007, 989-1003; Mukerji G., *BMC Urology* 6, 2006, 6; US 2003/0207904; US 2005/6893626, thesis by Behrendt H. J. 2004, University of Bochum; Lashinger E. S. R. *Am. J. Physiol. Renal Physiol.* Am J Physiol Renal Physiol. 2008 Jun. 18. [Epub ahead of print]; PMID: 18562636).

However, many of the modulators of TRPM8 that have been found to date have shortcomings in relation to intensity of action, duration of action, skin/mucosa irritation, odor, taste, solubility and/or volatility.

The applicant's prior international patent application PCT/EP2009/061019 proposes individual compounds for modulation of the TRPM8 receptor. For example, the following compounds have been disclosed:

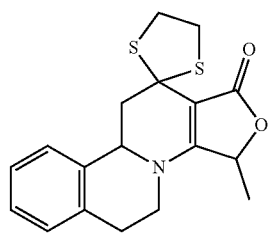

2

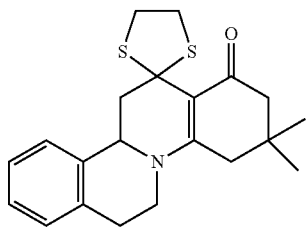

1

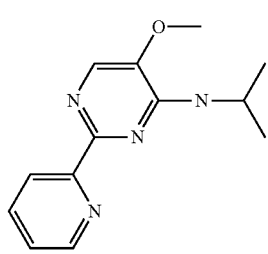

3

-continued

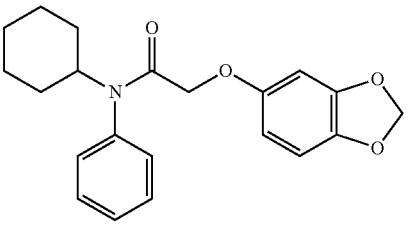

4

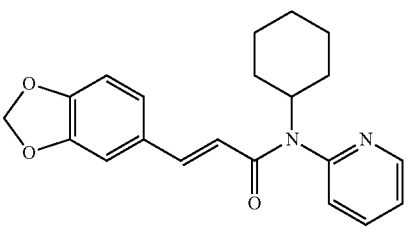

5

These compounds are also commercially available:
Compound 1 under CAS number: 99602-94-5 (3R-cis form)
Compound 2 under CAS number: 165753-08-2
Compound 3 under CAS number: 338771-57-6
Compound 4 under CAS number: 878942-21-3
Compound 5 under CAS number: 748783-13-3 (no stereochemistry)

Reference is additionally made at this point to the applicant's international patent application PCT/EP2010/067936, in which compounds for modulation of the TRPM8 receptor are likewise proposed.

The primary object of the present invention was to identify new substances that have an exceptional physiological cooling effect, preferably those that lead to modulation of the TRPM8 receptor, which are usable as alternatives to, preferably as more suitable agents than, the modulators known to date. Such compounds should especially also be suitable for uses in the cosmetics sector (e.g. haircare, skincare, oral care), foods and feeds, textiles, OTC products (e.g. burn ointment), pharmaceuticals (e.g. tumor treatment, bladder weakness) or packaging. The compounds or mixtures of compounds to be specified should preferably exhibit minimum intrinsic taste, and especially have only a slight bitter taste, if any at all, and cause minimum irritation.

For the achievement of the object of the invention, the search was in particular for compositions having actives that can impart a particularly long-lasting cool sensation. These compositions were preferably additionally to be able to impart cool impressions that are particularly intense and/or set in rapidly.

On the oral mucosa, many of the abovementioned conventional cooling substances known in the prior art all show more or less identical cooling characteristics. The cooling fresh sensation that they impart sets in after about 0.5 minute, but then levels off again relatively quickly after a peak at 3 to 5 minutes, the cooling being clearly perceptible for a total period of at most 30 minutes and, as experience has shown, having an intensity and duration that can be influenced only to a minor degree by a change in the dose. On the consumer side, however, there is a desire for an especially long-lasting cooling effect associated by the user with a corresponding perception of freshness and wellbeing.

It has been found that, surprisingly, the compounds to be used in accordance with the invention have the common property of achieving a particularly long cooling effect on the skin or mucosa in vivo. This was not predictable for the TRPM8 agonists mentioned in this application, nor does it apply to all these agonists.

There were no pointers in the prior art to date that specifically the compounds for use in accordance with the invention are capable of imparting a particularly suitable cooling effect. In order to quantify the long-lasting cooling effect, it is possible to conduct comparative tests with N-ethylmenthane-3-carboxamide. For these comparative tests, the person skilled in the art exchanges the compound for use in accordance with the invention or the compounds for N-ethylmenthane-3-carboxamide (also WS3), preferably in the same concentration. Then the cooling effects of the respective compositions are compared with one another. If the compounds for use in accordance with the invention are present in the composition to be examined in a concentration of higher than 100 ppm, it is preferable that, for the evaluation as to whether the cooling effect is prolonged compared to WS3, the composition to be tested should be diluted such that the inventive compounds for use are present in a concentration of 100 ppm. The same dilution step should of course also be implemented for the comparative composition comprising WS3.

In this connection, it is preferable that, in the corresponding comparisons, the cooling effect of the compositions comprising the compounds for use in accordance with the invention is prolonged preferably by at least 10 minutes, more preferably by at least 15 minutes, further preferably by at least 20 minutes and especially preferably by at least 30 minutes compared to the comparative tests.

The primary object of the present invention is achieved in accordance with the invention by a non-therapeutic method of modulation, preferably of in vitro and/or in vivo modulation, of the cold menthol receptor TRPM8, wherein the receptor is contacted with at least one modulator selected from the group consisting of compounds of the following structure type 1:

Structure Type 1:

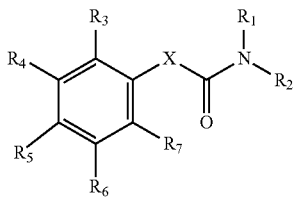

in which
R$_1$ consists of the following structure:

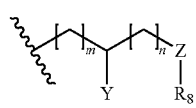

(R1)

in which
Z is selected from the group consisting of O and S;
n=0 or 1;
m
=1 and Y is hydrogen and R8 is a linear or branched C$_1$ to C$_5$ alkane, preferably a C$_5$ alkane, or Y is NR$_9$ or CR$_9$ and R$_9$ together with R$_8$ forms a partly or fully saturated 5- or 6-membered ring, or =0, 2 or 3 and Y is hydrogen and R$_8$ is a linear or branched C$_1$ to C$_5$ alkane, preferably a C$_5$ alkane, or Y is NR$_9$ or CR$_9$ and R$_9$ together with R$_8$ forms an aromatic, partly or fully saturated 5- or 6-membered ring;

R$_2$ is a linear or branched C$_1$ to C$_5$ alkyl radical, a 5- or 6-membered cycloalkyl radical or a 5- or 6-membered aryl radical, where the alkyl radical, the cycloalkyl radical or the aryl radical optionally includes one or two (ring) heteroatoms;

R$_3$, R$_4$, R$_5$, R$_8$ and R$_7$ are the same or different and are selected from the group consisting of
hydrogen;
halogens;
linear or branched C$_1$- to C$_6$-alkyl groups optionally bearing 1, 2, 3 or 4 identical or different substituents selected from the group consisting of NH$_2$, OH, SH, halogens and linear or branched C$_1$- to C$_6$-alkyl groups;
linear or branched C$_1$- to C$_6$-alkoxy groups optionally bearing 1, 2, 3 or 4 identical or different substituents selected from the group consisting of NH$_2$, OH, SH, halogens and C$_1$- to C$_6$-alkoxy groups;
mono- or polycyclic aryl, arylalkyl and heteroaryl groups optionally bearing 1, 2, 3 or 4 identical or different substituents selected from the group consisting of NH$_2$, OH, SH, halogens, linear or branched C$_1$- to C$_6$-alkyl groups; where the heteroaryl groups have 1, 2, 3 or 4 ring heteroatoms that are the same or different and are selected from the group consisting of O, N and S, or two adjacent R$_3$, R$_4$, R$_5$, R$_8$ and R$_7$ radicals together with the carbon atoms to which they are bonded form a 4-, 5-, 6- or 7-membered, mono- or polyunsaturated heterocyclic ring optionally bearing 1, 2, 3, 4 or 5 identical or different substituents selected from the group consisting of linear or branched C$_1$- to C$_6$-alkyl groups, and having 1, 2 or 3 ring heteroatoms that are the same or different and are selected from the group consisting of O, N and S;

X
is selected from the group consisting of
—C$_1$- to C$_4$-alkylene groups; —C$_2$- to C$_4$-alkenylene groups, and -A-C$_1$- to C$_4$- or —C$_1$- to C$_4$-A-alkylene groups or -A-C$_2$- to C$_4$- or —C$_2$- to C$_4$-A-alkenylene groups, in which A is O, S or NH; or
is a chemical single bond;

and salts of these compounds, especially acid addition salts with inorganic or especially organic, mono- and especially polybasic carboxylic acids;
and optionally of these compounds in stereoisomerically pure form or mixtures of stereoisomers thereof.

There are various synonyms in the literature for "TRPM8": TRPP8, LTRPC6, CMR1, MGC2849, transient receptor potential cation channel subfamily M member 8. The scope of the present invention includes all designations. Also included are all functional modifications of the receptor such as, more particularly, splice variants, isoforms, for example TRPM8 CRA_a, TRPM8 CRA_b and all analogous receptors from different organisms, such as man, mouse, rat. The nucleotide or amino acid sequences of the various receptors are known per se and recorded in sequence databases. For example, the sequence information for hTRPM8 is registered under the number NM_024080.

A "modulator" in the context of the invention is a compound that can act as agonist and/or antagonist of the TRPM8 receptor in vivo and/or in vitro, especially in vivo.

Suitable modulators may act here either solely as antagonist or agonist, especially solely as agonist, or both as antagonist and as agonist. It is especially possible here to establish an agonistic or antagonistic effect as a function of the particular modulator concentration chosen.

An "agonist" here is a compound that imparts activation of the TRPM8 receptor, i.e. induces a $Ca^{2+}$ influx into the cold-sensitive neurons and hence imparts a cold sensation.

An "antagonist", by contrast, is a compound that can counteract this activation of the TRPM8 receptor.

The modulators of the invention can exert their effect by binding reversibly or irreversibly, specifically or non-specifically, to a TRPM8 receptor molecule. Usually, the binding is noncovalent via ionic and/or nonionic, for example hydrophobic, interactions with the receptor molecule. "Specific" here comprises exclusive interaction with one or more different TRPM8 receptor molecules (for example TRPM8 molecules of different origin or different isoforms). "Nonspecific", by contrast, is an interaction of the modulator with multiple different receptor molecules of different function and/or sequence, but as a result of which a desired agonistic and/or antagonistic modulation (as described above) of the TRPM8 receptor can be detected.

A modulator of the invention serves especially for induction of a cold sensation in man and/or animals. There is preferably "induction of a cold sensation" when the compound in the cellular activity test described herein shows an agonistic effect on hTRPM8.

Compositions of the invention comprise, as well as the constituents that are customary for the respective composition, an effective amount of at least one modulator of the invention. "Effective" in this context means a concentration of the modulator sufficient for imparting the desired effect on application of the composition (for example application to the skin), for example a pharmacological effect or sensory effect, for example the olfactory cold effect.

Unless stated otherwise, the following general definitions are applicable in the context of the present invention:

Halogen: F, Cl, Br or I

Alkyl and all alkyl moieties in radicals derived therefrom, for example alkoxy, alkylthio, alkoxyalkyl, alkoxyalkoxy, alkylamino and dialkylamino: saturated, linear or branched hydrocarbyl radicals having 1 to 4, 1 to 6, 1 to 8 or 1 to 10 carbon atoms, e.g.

$C_1$- to $C_8$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$- to $C_5$-alkoxy, comprising $C_1$- to $C_4$-alkoxy, for example methoxy, ethoxy, n-propoxy, 1-methylethoxy, butoxy, 1-methylpropoxy, 2-methylpropoxy or 1,1-dimethylethoxy; and, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

Cycloalkyl (ring): carbocyclic radicals having 3 to 20 carbon atoms, for example $C_3$- to $C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl, cycloheptyl, and also cyclopropylmethyl, cyclopropylethyl, cyclobutylmethyl, cyclobutylethyl, cyclopentylmethyl, cyclopentylethyl, cyclohexylmethyl or $C_3$- to $C_7$-cycloalkyl, such as cyclopropyl, cyclobutyl, cyclopentyl, cyclohexyl, cycloheptyl, cyclopropylmethyl, cyclopropylethyl, cyclobutylmethyl, cyclopentylmethyl, cyclopentylethyl, cyclohexylmethyl, where the radical may be attached to the rest of the molecule via any suitable carbon atom, Alkylene: linear or singly or multiply branched hydrocarbon bridging groups having 1 to 20 carbon atoms, for example $C_1$- to $C_7$-alkylene groups selected from —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$—, $(CH_2)_4$—, —$(CH_2)_5$—, —$(CH_2)_6$—, —$(CH_2)_7$—, —$CH(CH_3)$—$CH_2$—$CH_2$—$CH(CH_3)$— or —$CH(CH_3)$—$CH_2$—$CH_2$—$CH_2$—$CH(CH_3)$— or $C_1$- to $C_4$-alkylene groups selected from —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$—.

Alkenylene: the mono- or polyunsaturated, especially monounsaturated, analogs of the above alkylene groups having 2 to 20 carbon atoms, especially $C_2$- to $C_7$-alkenylenes or $C_2$- to $C_4$-alkenylene, such as —CH=CH—, —CH=CH—$CH_2$—, —$CH_2$—CH=CH—, —CH=CH—$CH_2$—$CH_2$—, —$CH_2$—H=CH—$CH_2$—, —$CH_2$—$CH_2$—CH=CH—, —$CH(CH_3)$—CH=CH—, —$CH_2$—$C(CH_3)$=CH—.

Aryl: mono- or polycyclic, preferably mono- or bicyclic, optionally substituted aromatic radicals having 6 to 20, especially 6 to 10, ring carbon atoms, for example phenyl, biphenyl, naphthyl such as 1- or 2-naphthyl, tetrahydronaphthyl, fluorenyl, indenyl and phenanthrenyl. These aryl radicals may optionally bear 1, 2, 3, 4, 5 or 6 identical or different substituents.

Arylalkyl: the aryl-substituted analogs of the above alkyl radicals, where aryl likewise has the definitions stated above, such as phenyl-$C_1$- to $C_4$-alkyl radicals selected from phenylmethyl or phenylethyl.

Heterocyclyl (heterocyclic ring): five- to seven-membered saturated, partially unsaturated or aromatic heterocycles or heterocyclyl radicals containing one, two, three or four heteroatoms from the group of O, N and S, for example 5- or 6-membered saturated or monounsaturated heterocyclyl, comprising one to two nitrogen atoms and/or an oxygen or sulfur atom or one or two oxygen and/or sulfur atoms as ring members, e.g. 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;

5-membered aromatic heterocyclyl (=heteroaryl or hetaryl), comprising, in addition to carbon atoms, one, two or three nitrogen atoms or one or two nitrogen atoms and one sulfur or oxygen atom as ring members, e.g. 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, and 1,3,4-triazol-2-yl;

5-membered aromatic heterocyclyl (=heteroaryl or hetaryl) having 1, 2, 3 or 4 nitrogen atoms as ring members, such as 1-, 2- or 3-pyrrolyl, 1-, 3- or 4-pyrazolyl, 1-, 2- or 4-imidazolyl, 1,2,3-[1H]-triazol-1-yl, 1,2,3-[2H]-triazol-2-yl, 1,2,3-[1H]-triazol-4-yl, 1,2,3-[1H]-triazol-5-yl, 1,2,3-[2H]-triazol-4-yl, 1,2,4-[1H]-triazol-1-yl, 1,2,4-[1H]-triazol-3-yl, 1,2,4-[1H]-triazol-5-yl, 1,2,4-[4H]-triazol-4-yl, 1,2,4-[4H]-triazol-3-yl, [1H]-tetrazol-1-yl, [1H]-tetrazol-5-yl, [2H]-tetrazol-2-yl and [2H]-tetrazol-5-yl;

5-membered aromatic heterocyclyl (=heteroaryl or hetaryl) having 1 heteroatom selected from oxygen and sulfur and optionally 1, 2 or 3 nitrogen atoms as ring members, for example 2-furyl, 3-furyl, 2-thienyl, 3-thienyl, 3- or 4-isoxazolyl, 3- or 4-isothiazolyl, 2-, 4- or 5-oxazolyl, 2-, 4- or 5-thiazolyl, 1,2,4-thiadiazol-3-yl, 1,2,4-thiadiazol-5-yl, 1,3,4-thiadiazol-2-yl, 1,2,4-oxadiazol-3-yl, 1,2,4-oxadiazol-5-yl and 1,3,4-oxadiazol-2-yl;

6-membered heterocyclyl (=heteroaryl or hetaryl), comprising, in addition to carbon atoms, one or two, or one, two or three, nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl; 1,2,4-triazin-5-yl, 1,2,4-triazin-6-yl and 1,3,5-triazin-2-yl;

Substituents, as for the above radicals in particular, are especially selected from keto groups, —COOH, —COO-alkyl, —OH, —SH, —CN, amino, —NO$_2$, alkyl, or where one or more hydrogen atoms in the alkyl groups may be replaced by halogen.

In a preferred embodiment of the method of the invention, the compounds of structure type 1 are selected from the group A consisting of the following compounds:

| Structure | Name |
| --- | --- |
| | (E)-3-(1,3-benzodioxol-5-yl)-N-phenyl-N-tetrahydrofuran-3-yl-prop-2-enamide |
| | (E)-3-(4-methoxyphenyl)-N-phenyl-N-tetrahydrofuran-3-yl-prop-2-enamide |
| | (E)-N-phenyl-3-(p-tolyl)-N-tetrahydrofuran-3-ylprop-2-enamide |
| | 2-(4-methoxyphenoxy)-N-phenyl-N-tetrahydrothiophen-3-ylacetamide |

-continued

| Structure | Name |
|---|---|
| | (E)-3-(1,3-benzodioxol-5-yl)-N-(2-pyridyl)-N-tetrahydrothiophen-3-yl-prop-2-enamide |
| | (E)-3-(p-tolyl)-N-(2-pyridyl)-N-tetrahydrothiophen-3-ylprop-2-enamide |
| | (E)-3-(4-methoxyphenyl)-N-(2-pyridyl)-N-tetrahydrothiophen-3-yl-prop-2-enamide |
| | (E)-3-phenyl-N-(2-pyridyl)-N-tetrahydrothiophen-3-ylprop-2-enamide |
| | (E)-3-(1,3-benzodioxol-5-yl)-N,N-bis(2-pyridyl)prop-2-enamide |
| | (E)-3-(1,3-benzodioxol-5-yl)-N-(1H-pyrazol-3-yl)-N-(tetrahydrofuran-2-ylmethyl)prop-2-enamide |
| | (E)-3-(p-tolyl)-N-(1H-pyrazol-3-yl)-N-(tetrahydrofuran-2-ylmethyl)prop-2-enamide |

-continued

| Structure | Name |
|---|---|
| 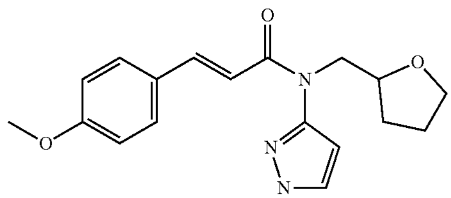 [SMILES: COc1ccc(/C=C/C(=O)N(CC2CCCO2)c2cc[nH]n2)cc1] | (E)-3-(4-methoxyphenyl)-N-(1H-pyrazol-3-yl)-N-(tetrahydrofuran-2-ylmethyl)prop-2-enamide |
| 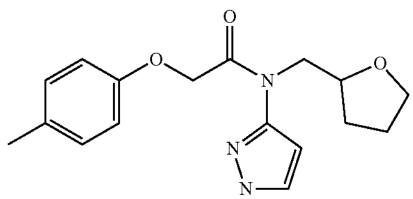 [SMILES: Cc1ccc(OCC(=O)N(CC2CCCO2)c2cc[nH]n2)cc1] | 2-(4-methylphenoxy)-N-(1H-pyrazol-3-yl)-N-(tetrahydrofuran-2-ylmethyl)acetamide |
| 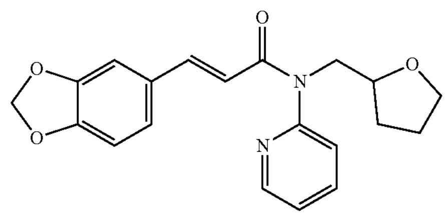 [SMILES: O=C(/C=C/c1ccc2c(c1)OCO2)N(CC1CCCO1)c1ccccn1] | (E)-3-(1,3-benzodioxol-5-yl)-N-(2-pyridyl)-N-(tetrahydrofuran-2-ylmethyl)prop-2-enamide |
| 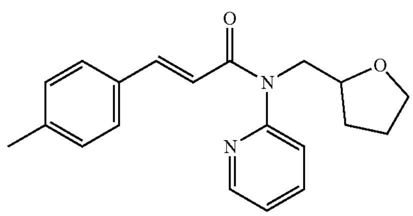 [SMILES: Cc1ccc(/C=C/C(=O)N(CC2CCCO2)c2ccccn2)cc1] | (E)-3-(p-tolyl)-N-(2-pyridyl)-N-(tetrahydrofuran-2-ylmethyl)prop-2-enamide |
| 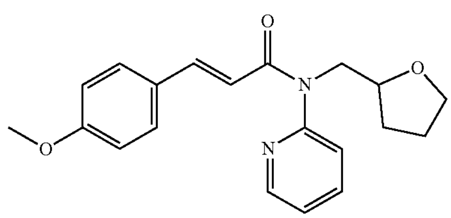 [SMILES: COc1ccc(/C=C/C(=O)N(CC2CCCO2)c2ccccn2)cc1] | (E)-3-(4-methoxyphenyl)-N-(2-pyridyl)-N-(tetrahydrofuran-2-ylmethyl)prop-2-enamide |
| 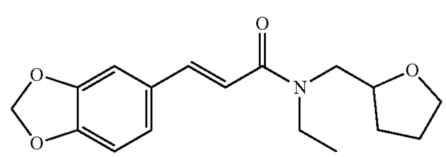 [SMILES: CCN(CC1CCCO1)C(=O)/C=C/c1ccc2c(c1)OCO2] | (E)-3-(1,3-benzodioxol-5-yl)-N-ethyl-N-(tetrahydrofuran-2-ylmethyl)prop-2-enamide |
| 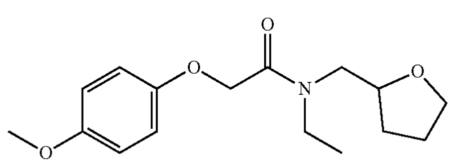 [SMILES: CCN(CC1CCCO1)C(=O)COc1ccc(OC)cc1] | N-ethyl-2-(4-methoxyphenoxy)-N-(tetrahydrofuran-2-ylmethyl)acetamide |
| 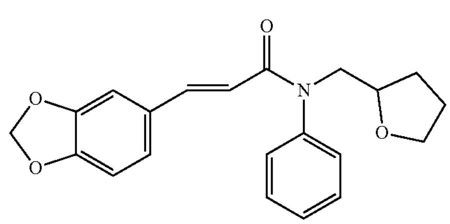 [SMILES: O=C(/C=C/c1ccc2c(c1)OCO2)N(CC1CCCO1)c1ccccc1] | (E)-3-(1,3-benzodioxol-5-yl)-N-phenyl-N-(tetrahydrofuran-2-ylmethyl)prop-2-enamide |

-continued

| Structure | Name |
|---|---|
| 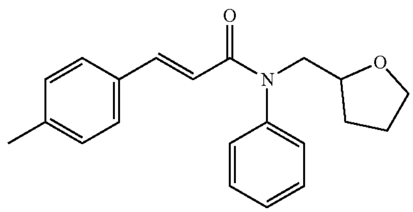 [SMILES: Cc1ccc(/C=C/C(=O)N(CC2CCCO2)c2ccccc2)cc1] | (E)-N-phenyl-3-(p-tolyl)-N-(tetrahydrofuran-2-yl-methyl)prop-2-enamide |
| 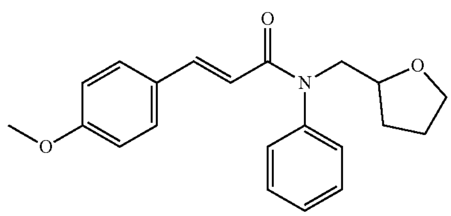 | (E)-3-(4-methoxyphenyl)-N-phenyl-N-(tetrahydro-furan-2-ylmethyl)prop-2-enamide |
| 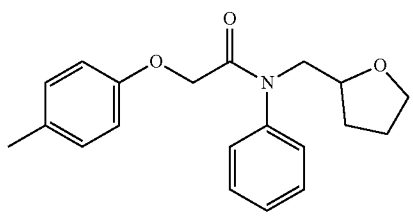 [SMILES: Cc1ccc(OCC(=O)N(CC2CCCO2)c2ccccc2)cc1] | 2-(4-methylphenoxy)-N-phenyl-N-(tetrahydro-furan-2-ylmethyl)acetamide |
| 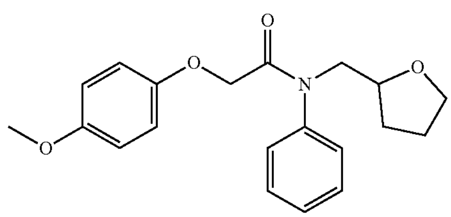 [SMILES: COc1ccc(OCC(=O)N(CC2CCCO2)c2ccccc2)cc1] | 2-(4-methoxyphenoxy)-N-phenyl-N-(tetrahydro-furan-2-ylmethyl)acetamide |
| 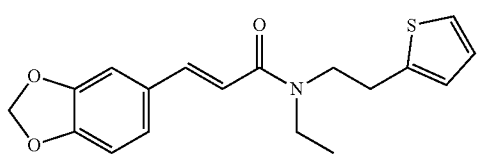 [SMILES: CCN(CCc1cccs1)C(=O)/C=C/c1ccc2c(c1)OCO2] | (E)-3-(1,3-benzodioxol-5-yl)-N-ethyl-N-[2-(2-thienyl)ethyl]prop-2-enamide |
| 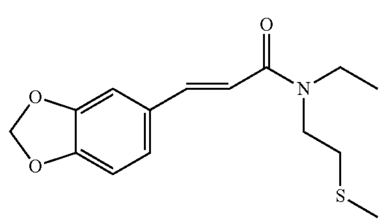 [SMILES: CCN(CCSC)C(=O)/C=C/c1ccc2c(c1)OCO2] | (E)-3-(1,3-benzodioxol-5-yl)-N-ethyl-N-(2-methyl-sulfanylethyl)prop-2-enamide |
| 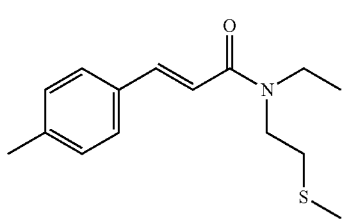 | (E)-N-ethyl-N-(2-methyl-sulfanylethyl)-3-(p-tolyl)prop-2-enamide |

-continued

| Structure | Name |
|---|---|
| 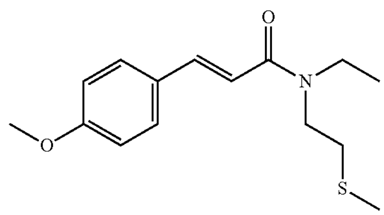 | (E)-N-ethyl-3-(4-methoxy-phenyl)-N-(2-methyl-sulfanylethyl)prop-2-enamide |
| 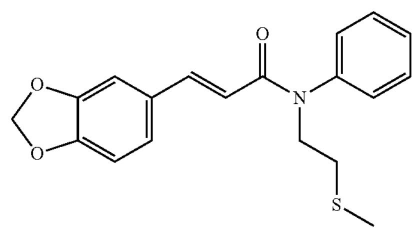 | (E)-3-(1,3-benzodioxol-5-yl)-N-(2-methyl-sulfanylethyl)-N-phenyl-prop-2-enamide |
| 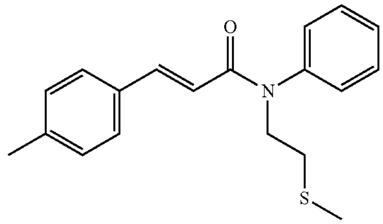 [SMILES: CSCCN(C(=O)/C=C/c1ccc(C)cc1)c1ccccc1] | (E)-N-(2-methyl-sulfanylethyl)-N-phenyl-3-(p-tolyl)prop-2-enamide |
| 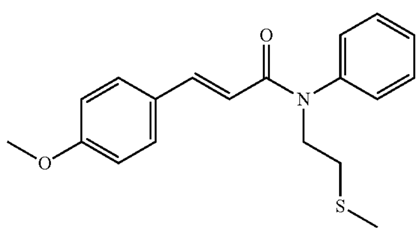 [SMILES: COc1ccc(/C=C/C(=O)N(CCSC)c2ccccc2)cc1] | (E)-3-(4-methoxyphenyl)-N-(2-methylsulfanylethyl)-N-phenyl-prop-2-enamide |
| 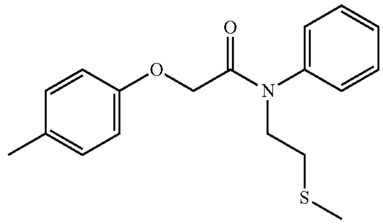 [SMILES: CSCCN(C(=O)COc1ccc(C)cc1)c1ccccc1] | 2-(4-methylphenoxy)-N-(2-methylsulfanylethyl)-N-phenyl-acetamide |
| 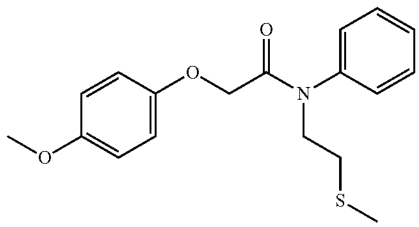 [SMILES: COc1ccc(OCC(=O)N(CCSC)c2ccccc2)cc1] | 2-(4-methoxyphenoxy)-N-(2-methylsulfanylethyl)-N-phenyl-acetamide |

-continued

| Structure | Name |
|---|---|
| 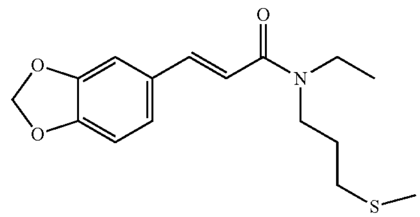 [SMILES: CCN(CCCSC)C(=O)/C=C/c1ccc2c(c1)OCO2] | (E)-3-(1,3-benzodioxol-5-yl)-N-ethyl-N-(3-methyl-sulfanylpropyl)prop-2-enamide |
| 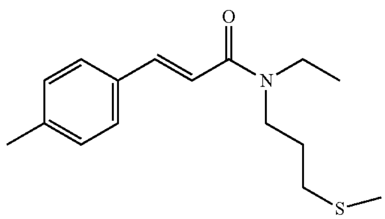 | (E)-N-ethyl-N-(3-methyl-sulfanylpropyl)-3-(p-tolyl)prop-2-enamide |
| 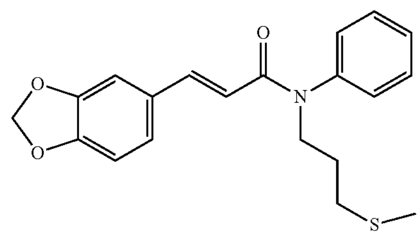 [SMILES: CSCCCN(C(=O)/C=C/c1ccc2c(c1)OCO2)c1ccccc1] | (E)-3-(1,3-benzodioxol-5-yl)-N-(3-methyl-sulfanylpropyl)-N-phenyl-prop-2-enamide |
| 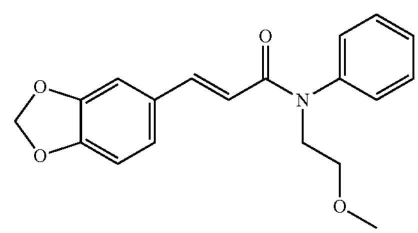 [SMILES: COCCN(C(=O)/C=C/c1ccc2c(c1)OCO2)c1ccccc1] | (E)-3-(1,3-benzodioxol-5-yl)-N-(2-methoxyethyl)-N-phenyl-prop-2-enamide |
| 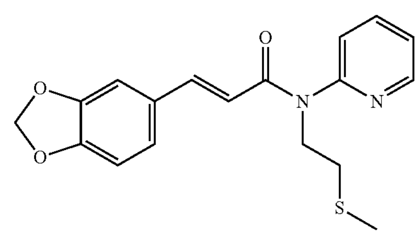 [SMILES: CSCCN(C(=O)/C=C/c1ccc2c(c1)OCO2)c1ccccn1] | (E)-3-(1,3-benzodioxol-5-yl)-N-(2-methyl-sulfanylethyl)-N-(2-pyridyl)prop-2-enamide |
| 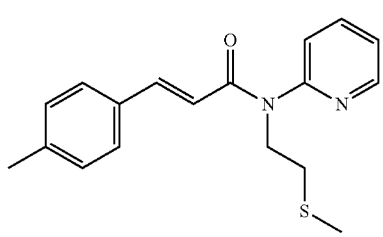 [SMILES: CSCCN(C(=O)/C=C/c1ccc(C)cc1)c1ccccn1] | (E)-N-(2-methyl-sulfanylethyl)-3-(p-tolyl)-N-(2-pyridyl)prop-2-enamide |

-continued

| Structure | Name |
|---|---|
| 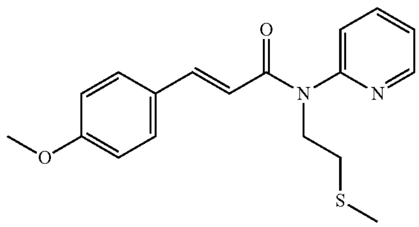 [SMILES: COc1ccc(/C=C/C(=O)N(CCSC)c2ccccn2)cc1] | (E)-3-(4-methoxyphenyl)-N-(2-methylsulfanylethyl)-N-(2-pyridyl)prop-2-enamide |
| 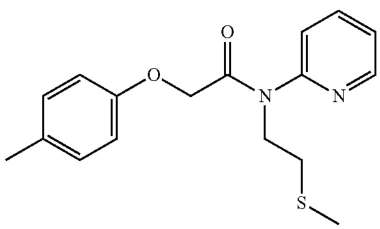 [SMILES: CSCCN(C(=O)COc1ccc(C)cc1)c1ccccn1] | 2-(4-methylphenoxy)-N-(2-methylsulfanylethyl)-N-(2-pyridyl)acetamide |
| 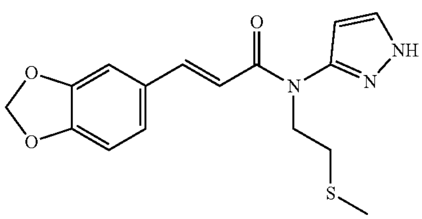 [SMILES: CSCCN(C(=O)/C=C/c1ccc2c(c1)OCO2)c1cc[nH]n1] | (E)-3-(1,3-benzodioxol-5-yl)-N-(2-methyl-sulfanylethyl)-N-(1H-pyrazol-3-yl)prop-2-enamide |
| 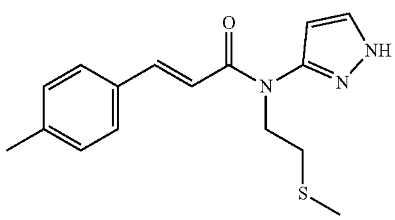 [SMILES: CSCCN(C(=O)/C=C/c1ccc(C)cc1)c1cc[nH]n1] | (E)-N-(2-methyl-sulfanylethyl)-3-(p-tolyl)-N-(1H-pyrazol-3-yl)prop-2-enamide |
| 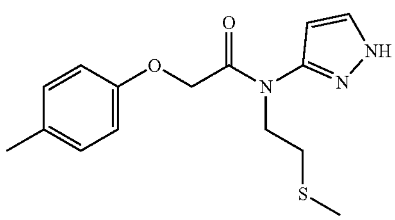 [SMILES: CSCCN(C(=O)COc1ccc(C)cc1)c1cc[nH]n1] | 2-(4-methylphenoxy)-N-(2-methylsulfanylethyl)-N-(1H-pyrazol-3-yl)acetamide |
| 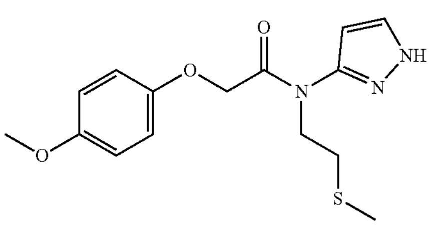 [SMILES: COc1ccc(OCC(=O)N(CCSC)c2cc[nH]n2)cc1] | 2-(4-methoxyphenoxy)-N-(2-methylsulfanylethyl)-N-(1H-pyrazol-3-yl)acetamide |

If there should be differences between the name given and the respective formula image, the evidence of the formula image takes precedence.

Particular preference here is given to the compounds from group A that are selected from group B consisting of the following compounds:

| Structure | Name |
|---|---|
| 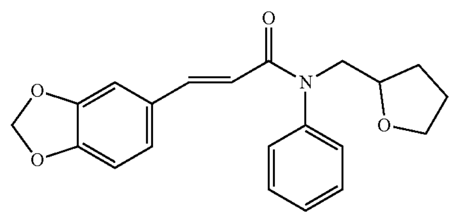 [SMILES: O=C(/C=C/c1ccc2c(c1)OCO2)N(CC1CCCO1)c1ccccc1] | (E)-3-(1,3-benzodioxol-5-yl)-N-phenyl-N-(tetrahydrofuran-2-ylmethyl)prop-2-enamide |
| 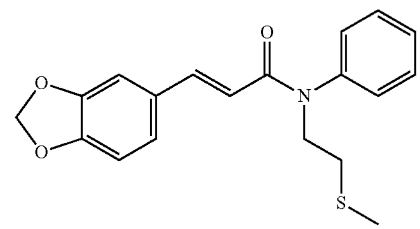 [SMILES: CSCCN(C(=O)/C=C/c1ccc2c(c1)OCO2)c1ccccc1] | (E)-3-(1,3-benzodioxol-5-yl)-N-(2-methylsulfanylethyl)-N-phenyl-prop-2-enamide |
| 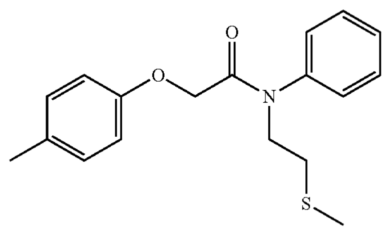 [SMILES: CSCCN(C(=O)COc1ccc(C)cc1)c1ccccc1] | 2-(4-methylphenoxy)-N-(2-methylsulfanylethyl)-N-phenyl-acetamide |
| 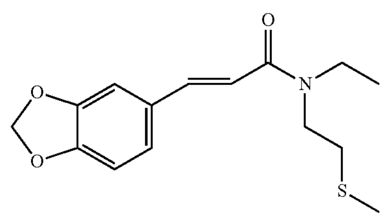 [SMILES: CCN(CCSC)C(=O)/C=C/c1ccc2c(c1)OCO2] | (E)-3-(1,3-benzodioxol-5-yl)-N-ethyl-N-(2-methyl-sulfanylethyl)prop-2-enamide |
| 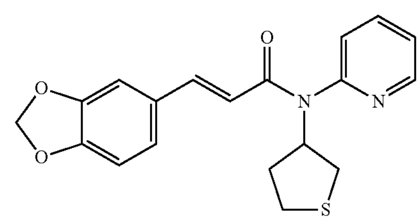 [SMILES: O=C(/C=C/c1ccc2c(c1)OCO2)N(c1ccccn1)C1CCSC1] | (E)-3-(1,3-benzodioxol-5-yl)-N-(2-pyridyl)-N-(tetrahydrothio-phen-3-yl-prop-2-enamide |
| 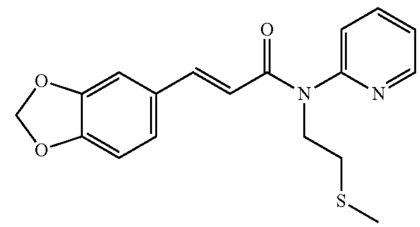 | (E)-3-(1,3-benzodioxol-5-yl)-N-(2-methylsulfanylethyl)-N-(2-pyridyl)prop-2-enamide |

-continued

| Structure | Name |
|---|---|
| 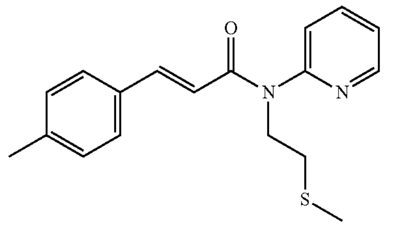 [SMILES: CSCCN(C(=O)/C=C/c1ccc(C)cc1)c1ccccn1] | (E)-N-(2-methylsulfanylethyl)-3-(p-tolyl)-N-(2-pyridyl)prop-2-enamide |
| 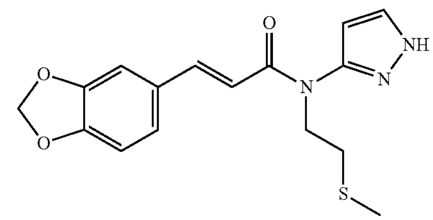 [SMILES: CSCCN(C(=O)/C=C/c1ccc2c(c1)OCO2)c1cc[nH]n1] | (E)-3-(1,3-benzodioxol-5-yl)-N-(2-methylsulfanylethyl)-N-(1H-pyrazol-3-yl)prop-2-enamide |
| 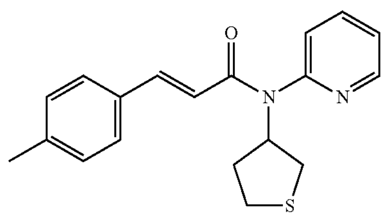 | (E)-3-(p-tolyl)-N-(2-pyridyl)-N-tetrahydrothiophen-3-ylprop-2-enamide |
| 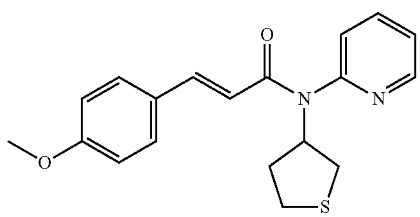 [SMILES: COc1ccc(/C=C/C(=O)N(c2ccccn2)C2CCSC2)cc1] | (E)-3-(4-methoxyphenyl)-N-(2-pyridyl)-N-tetrahydrothiophen-3-yl-prop-2-enamide |
| 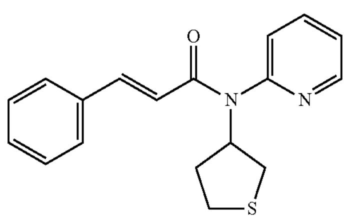 [SMILES: O=C(/C=C/c1ccccc1)N(c1ccccn1)C1CCSC1] | (E)-3-phenyl-N-(2-pyridyl)-N-tetrahydrothiophen-3-ylprop-2-enamide |
| 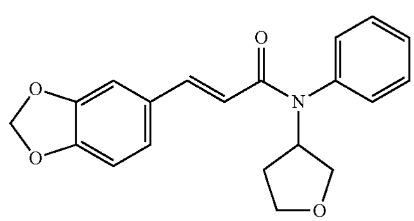 [SMILES: O=C(/C=C/c1ccc2c(c1)OCO2)N(c1ccccc1)C1CCOC1] | (E)-3-(1,3-benzodioxol-5-yl)-N-phenyl-N-tetrahydrofuran-3-yl-prop-2-enamide |
| 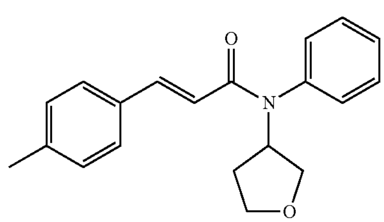 [SMILES: Cc1ccc(/C=C/C(=O)N(c2ccccc2)C2CCOC2)cc1] | (E)-N-phenyl-3-(p-tolyl)-N-tetrahydrofuran-3-ylprop-2-enamide |

Further preference is given to the compounds from groups A and B that are selected from group C consisting of the following compounds:

| Structure | Name |
|---|---|
| 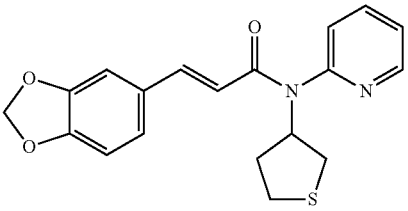 | (E)-3-(1,3-benzodioxol-5-yl)-N-(2-pyridyl)-N-tetrahydrothiophen-3-yl-prop-2-enamide |
| 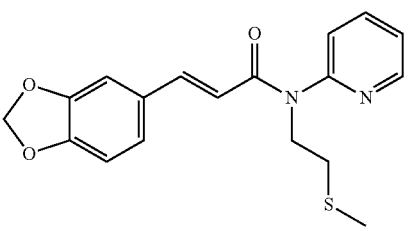 [SMILES: CSCCN(C(=O)/C=C/c1ccc2c(c1)OCO2)c1ccccn1] | (E)-3-(1,3-benzodioxol-5-yl)-N-(2-methyl-sulfanylethyl)-N-(2-pyridyl)prop-2-enamide |
| 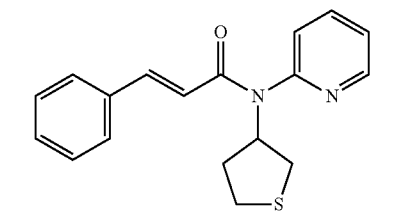 [SMILES: O=C(/C=C/c1ccccc1)N(c1ccccn1)C1CCSC1] | (E)-3-phenyl-N-(2-pyridyl)-N-tetrahydrothiophen-3-ylprop-2-enamide |
| 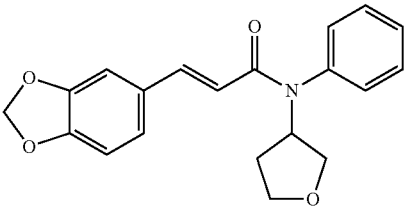 [SMILES: O=C(/C=C/c1ccc2c(c1)OCO2)N(c1ccccc1)C1CCOC1] | (E)-3-(1,3-benzodioxol-5-yl)-N-phenyl-N-tetrahydrofuran-3-yl-prop-2-enamide |

In one configuration of the present invention, the compounds of structure type 1 are not selected from the compounds as described in WO2011/061330.

In a preferred embodiment of the present invention, the compounds of structure type 1 are therefore not selected from the group D consisting of the following compounds:

Structure type 1:

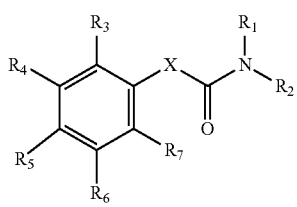

in which
$R_1$ consists of the following structure:

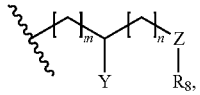

(R1)

in which
Z is selected from the group consisting of O and S;
n=0 or 1;
m=0 and Y is $NR_9$ or $CR_9$ and $R_9$ together with $R_8$ forms an aromatic or fully saturated 5- or 6-membered ring;
and
in which $R_2$ is a linear or branched $C_1$ to $C_5$ alkyl radical, a 5- or 6-membered cycloalkyl radical or a 5- or 6-membered aryl radical, where the cycloalkyl radical and the aryl radical optionally include one or two (ring) heteroatoms that are the same or different and are selected from O, N and S;
$R_3$, $R_4$, $R_5$, $R_6$ and $R_7$ are the same or different and are selected from the group consisting of
hydrogen;
halogens;
linear or branched $C_1$- to $C_6$-alkyl groups optionally bearing 1, 2, 3 or 4 identical or different substituents selected from the group consisting of $NH_2$, OH, SH, halogens and linear or branched $C_1$- to $C_6$-alkyl groups;
linear or branched $C_1$- to $C_6$-alkoxy groups optionally bearing 1, 2, 3 or 4 identical or different substituents selected from the group consisting of $NH_2$, OH, SH, halogens and $C_1$- to $C_6$-alkoxy groups;
mono- or polycyclic aryl, arylalkyl and heteroaryl groups optionally bearing 1, 2, 3 or 4 identical or different substituents selected from the group consisting of $NH_2$, OH, SH, halogens, linear or branched $C_1$- to $C_6$-alkyl groups; where the heteroaryl groups have 1, 2, 3 or 4 ring heteroatoms that are the same or different and are selected from the group consisting of O, N and S, or
two adjacent $R_3$, $R_4$, $R_5$, $R_6$ and $R_7$ radicals together with the carbon atoms to which they are bonded form a 4-, 5-, 6- or 7-membered, mono- or polyunsaturated heterocyclic ring optionally bearing 1, 2, 3, 4 or 5 identical or different substituents selected from the group consisting of linear or branched $C_1$- to $C_6$-alkyl groups, and having 1, 2 or 3 ring heteroatoms that are the same or different and are selected from the group consisting of O, N and S;
X
is selected from the group consisting of
$C_1$- to $C_4$-alkylene groups; $—C_2$- to $C_4$-alkenylene groups, and -A-$C_1$- to $C_4$- or $—C_1$- to $C_4$-A-alkylene groups or -A-$C_2$- to $C_4$- or $—C_2$- to $C_4$-A-alkenylene groups, in which A is O, S or NH; or
is a chemical single bond;
and salts of these compounds, especially acid addition salts with inorganic or especially organic, mono- and especially polybasic carboxylic acids;
and optionally of these compounds in stereoisomerically pure form or mixtures of stereoisomers thereof.

In a further preferred embodiment of the present invention, the compounds of structure type 1 are not selected from the group E consisting of the following compounds:

| Structure | Name |
|---|---|
| 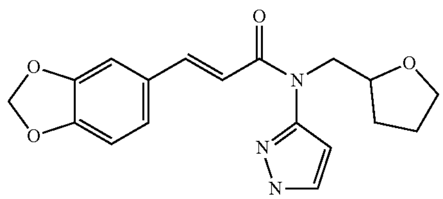 [SMILES: O=C(/C=C/c1ccc2c(c1)OCO2)N(CC1CCCO1)c1cc[nH]n1] | (E)-3-(1,3-benzodioxol-5-yl)-N-(1H-pyrazol-3-yl)-N-(tetrahydrofuran-2-yl-methyl)prop-2-enamide |
| 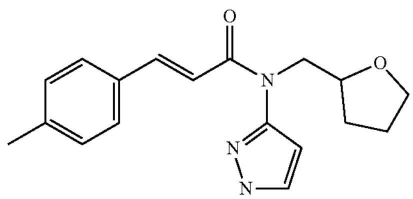 [SMILES: Cc1ccc(/C=C/C(=O)N(CC2CCCO2)c2cc[nH]n2)cc1] | (E)-3-(p-tolyl)-N-(1H-pyrazol-3-yl)-N-(tetrahydro-furan-2-ylmethyl)prop-2-enamide |
| 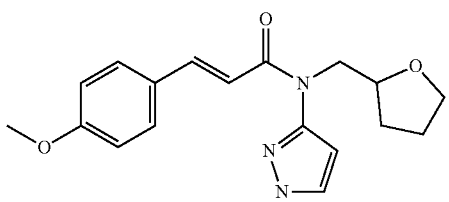 [SMILES: COc1ccc(/C=C/C(=O)N(CC2CCCO2)c2cc[nH]n2)cc1] | (E)-3-(4-methoxyphenyl)-N-(1H-pyrazol-3-yl)-N-(tetrahydrofuran-2-yl-methyl)prop-2-enamide |
| 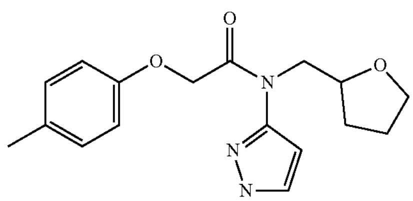 [SMILES: Cc1ccc(OCC(=O)N(CC2CCCO2)c2cc[nH]n2)cc1] | 2-(4-methylphenoxy)-N-(1H-pyrazol-3-yl)-N-(tetra-hydrofuran-2-ylmethyl)acetamide |
| 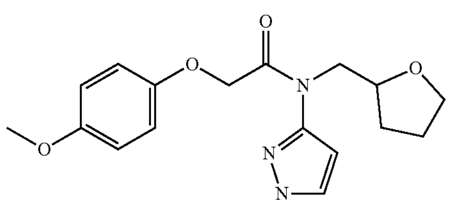 [SMILES: COc1ccc(OCC(=O)N(CC2CCCO2)c2cc[nH]n2)cc1] | 2-(4-methoxyphenoxy)-N-(1H-pyrazol-3-yl)-N-(tetra-hydrofuran-2-ylmethyl)acetamide |
| 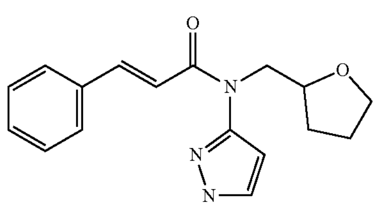 [SMILES: O=C(/C=C/c1ccccc1)N(CC1CCCO1)c1cc[nH]n1] | (E)-3-phenyl-N-(1H-pyrazol-3-yl)-N-(tetrahydrofuran-2-ylmethyl)prop-2-en-amide |
| 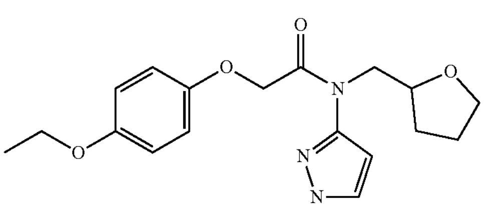 [SMILES: CCOc1ccc(OCC(=O)N(CC2CCCO2)c2cc[nH]n2)cc1] | 2-(4-ethoxyphenoxy)-N-(1H-pyrazol-3-yl)-N-(tetrahydrofuran-2-ylmethyl)acetamide |

-continued

| Structure | Name |
|---|---|
| | (E)-3-(4-ethoxyphenyl)-N-(1H-pyrazol-3-yl)-N-(tetrahydrofuran-2-ylmethyl)prop-2-enamide |
| | 2-(3-methylphenoxy)-N-(1H-pyrazol-3-yl)-N-(tetrahydrofuran-2-ylmethyl)acetamide |
| | 2-(1,3-benzodioxol-5-yloxy)-N-(1H-pyrazol-3-yl)-N-(tetrahydrofuran-2-ylmethyl)acetamide |
| | (E)-3-(3,4-dimethoxyphenyl)-N-(1H-pyrazol-3-yl)-N-(tetrahydrofuran-2-ylmethyl)prop-2-enamide |
| | 2-(2-methylphenoxy)-N-(1H-pyrazol-3-yl)-N-(tetrahydrofuran-2-ylmethyl)acetamide |
| | (E)-3-(1,3-benzodioxol-5-yl)-N-(2-pyridyl)-N-(tetrahydrofuran-2-ylmethyl)prop-2-enamide |
| | (E)-3-(p-tolyl)-N-(2-pyridyl)-N-(tetrahydrofuran-2-ylmethyl)prop-2-enamide |

-continued

| Structure | Name |
|---|---|
|  | (E)-3-(4-methoxyphenyl)-N-(2-pyridyl)-N-(tetrahydrofuran-2-ylmethyl)prop-2-enamide |
|  | 2-(4-methylphenoxy)-N-(2-pyridyl)-N-(tetrahydrofuran-2-ylmethyl)acetamide |
|  | 2-(4-methoxyphenoxy)-N-(2-pyridyl)-N-(tetrahydrofuran-2-ylmethyl)acetamide |
|  | (E)-3-phenyl-N-(2-pyridyl)-N-(tetrahydrofuran-2-ylmethyl)prop-2-enamide |
|  | 2-(4-ethoxyphenoxy)-N-(2-pyridyl)-N-(tetrahydrofuran-2-ylmethyl)acetamide |
|  | (E)-3-(4-ethoxyphenyl)-N-(2-pyridyl)-N-(tetrahydrofuran-2-ylmethyl)prop-2-enamide |
|  | 2-(3-methylphenoxy)-N-(2-pyridyl)-N-(tetrahydrofuran-2-ylmethyl)acetamide |

-continued

| Structure | Name |
|---|---|
| 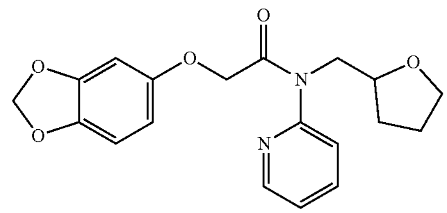 [SMILES: O=C(COc1ccc2c(c1)OCO2)N(CC1CCCO1)c1ccccn1] | 2-(1,3-benzodioxol-5-yloxy)-N-(2-pyridyl)-N-(tetrahydrofuran-2-ylmethyl)acetamide |
| | (E)-3-(3,4-dimethoxyphenyl)-N-(2-pyridyl)-N-(tetrahydrofuran-2-yl-methyl)prop-2-enamide |
| | (E)-3-(1,3-benzodioxol-5-yl)-N-phenyl-N-(tetrahydrofuran-3-yl-prop-2-enamide |
| 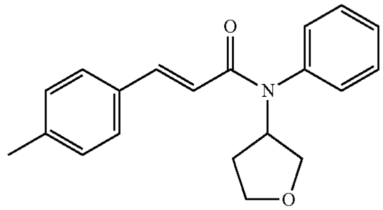 [SMILES: Cc1ccc(/C=C/C(=O)N(c2ccccc2)C2CCOC2)cc1] | (E)-N-phenyl-3-(p-tolyl)-N-tetrahydrofuran-3-yl-prop-2-enamide |
| | (E)-3-(4-methoxyphenyl)-N-phenyl-N-tetrahydrofuran-3-yl-prop-2-enamide |
| 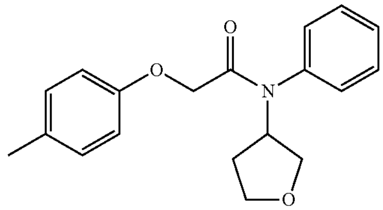 [SMILES: Cc1ccc(OCC(=O)N(c2ccccc2)C2CCOC2)cc1] | 2-(4-methylphenoxy)-N-phenyl-N-tetrahydrofuran-3-yl-acetamide |
| 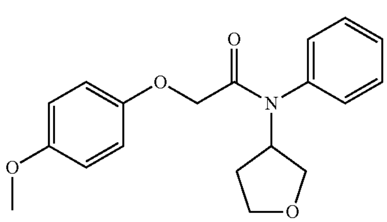 [SMILES: COc1ccc(OCC(=O)N(c2ccccc2)C2CCOC2)cc1] | 2-(4-methoxyphenoxy)-N-phenyl-N-tetrahydrofuran-3-yl-acetamide |

-continued

| Structure | Name |
|---|---|
| 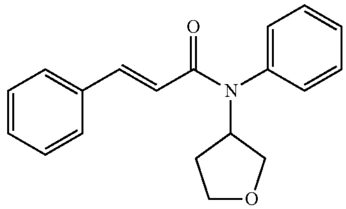 | (E)-N,3-diphenyl-N-tetra-hydrofuran-3-yl-prop-2-enamide |
| 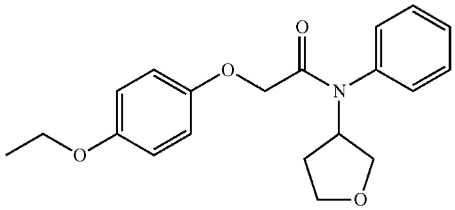 [SMILES: CCOc1ccc(OCC(=O)N(c2ccccc2)C2CCOC2)cc1] | 2-(4-ethoxyphenoxy)-N-phenyl-N-tetrahydrofuran-3-yl-acetamide |
| 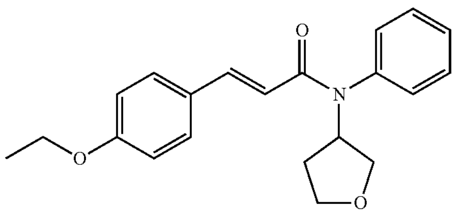 [SMILES: CCOc1ccc(/C=C/C(=O)N(c2ccccc2)C2CCOC2)cc1] | (E)-3-(4-ethoxyphenyl)-N-phenyl-N-tetrahydrofuran-3-yl-prop-2-enamide |
| 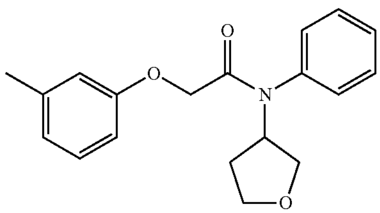 | 2-(3-methylphenoxy)-N-phenyl-N-tetrahydrofuran-3-yl-acetamide |
| | 2-(1,3-benzodioxol-5-yloxy)-N-phenyl-N-tetrahdydrofuran-3-yl-acetamide |
| | (E)-3-(3,4-dimethoxyphenyl)-N-phenyl-N-tetrahydrofuran-3-yl-prop-2-enamide |
| 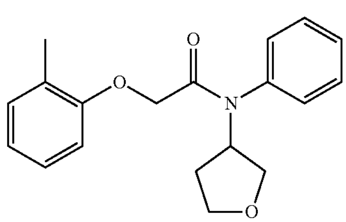 [SMILES: Cc1ccccc1OCC(=O)N(c1ccccc1)C1CCOC1] | 2-(2-methylphenoxy)-N-phenyl-N-tetrahydrofuran-3-yl-acetamide |

-continued

| Structure | Name |
|---|---|
| 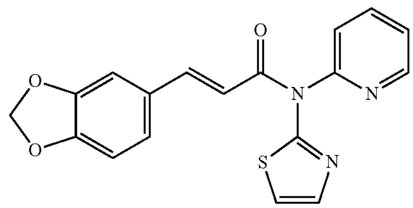 [SMILES: O=C(/C=C/c1ccc2c(c1)OCO2)N(c1ccccn1)c1nccs1] | (E)-3-(1,3-benzodioxol-5-yl)-N-(2-pyridyl)-N-thiazol-2-yl-prop-2-enamide |
| 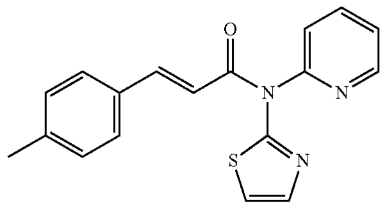 [SMILES: Cc1ccc(/C=C/C(=O)N(c2ccccn2)c2nccs2)cc1] | (E)-3-(p-tolyl)-N-(2-pyridyl)-N-thiazol-2-yl-prop-2-enamide |
| 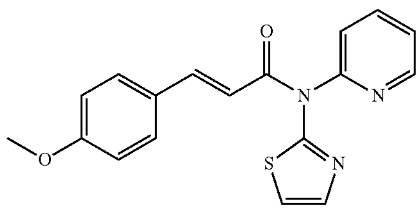 [SMILES: COc1ccc(/C=C/C(=O)N(c2ccccn2)c2nccs2)cc1] | (E)-3-(4-methoxyphenyl)-N-(2-pyridyl)-N-thiazol-2-yl-prop-2-enamide |
| 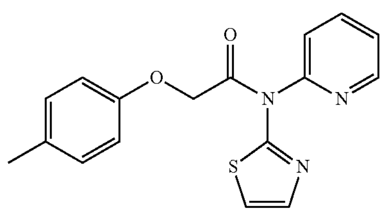 [SMILES: Cc1ccc(OCC(=O)N(c2ccccn2)c2nccs2)cc1] | 2-(4-methylphenoxy)-N-(2-pyridyl)-N-thiazol-2-yl-acetamide |
| 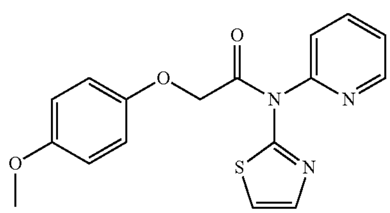 [SMILES: COc1ccc(OCC(=O)N(c2ccccn2)c2nccs2)cc1] | 2-(4-methoxyphenoxy)-N-(2-pyridyl)-N-thiazol-2-yl-acetamide |
| 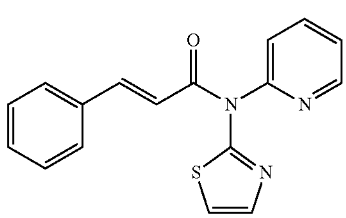 [SMILES: O=C(/C=C/c1ccccc1)N(c1ccccn1)c1nccs1] | (E)-3-phenyl-N-(2-pyridyl)-N-thiazol-2-yl-prop-2-enamide |
| 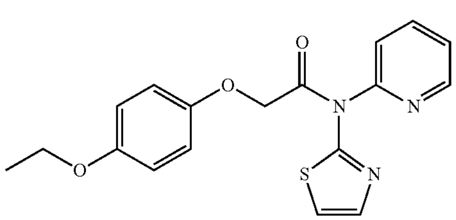 [SMILES: CCOc1ccc(OCC(=O)N(c2ccccn2)c2nccs2)cc1] | 2-(4-ethoxyphenoxy)-N-(2-pyridyl)-N-thiazol-2-yl-acetamide |

| Structure | Name |
|---|---|
| 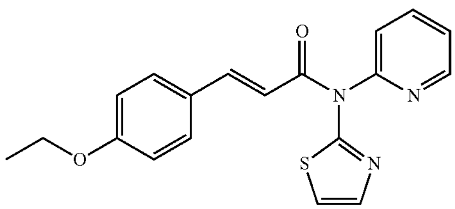 [SMILES: CCOc1ccc(/C=C/C(=O)N(c2ccccn2)c2nccs2)cc1] | (E)-3-(4-ethoxyphenyl)-N-(2-pyridyl)-N-thiazol-2-yl-prop-2-enamide |
| 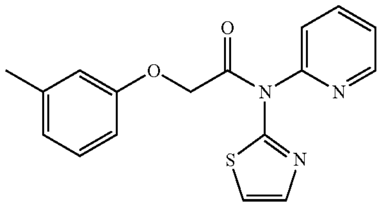 [SMILES: Cc1cccc(OCC(=O)N(c2ccccn2)c2nccs2)c1] | 2-(3-methylphenoxy)-N-(2-pyridyl)-N-thiazolyl-2-yl-acetamide |
| 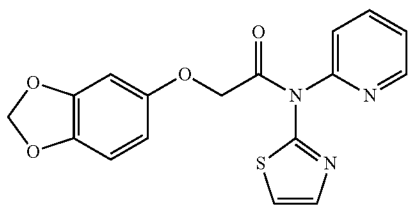 [SMILES: O=C(COc1ccc2c(c1)OCO2)N(c1ccccn1)c1nccs1] | 2-(1,3-benzodioxol-5-yloxy)-N-(2-pyridyl)-N-thiazol-2-yl-acetamide |
| 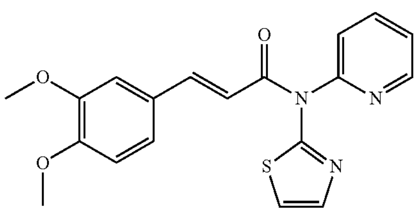 [SMILES: COc1ccc(/C=C/C(=O)N(c2ccccn2)c2nccs2)cc1OC] | (E)-3-(3,4-dimethoxy-phenyl)-N-(2-pyridyl)-N-thiazol-2-yl-prop-2-enamide |
| 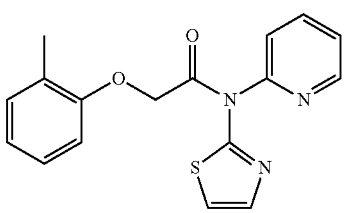 [SMILES: Cc1ccccc1OCC(=O)N(c1ccccn1)c1nccs1] | 2-(2-methylphenoxy)-N-(2-pyridyl)-N-thiazol-2-yl-acetamide |
| | (E)-3-(1,3-benzodioxol-5-yl)-N-phenyl-N-tetrahydrothiophen-3-yl-prop-2-enamide |
| 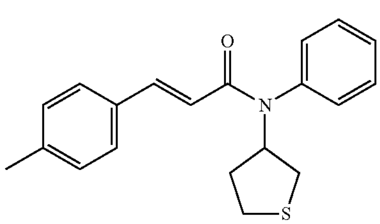 | (E)-N-phenyl-3-(p-tolyl)-N-tetrahydrothiophen-3-yl-prop-2-enamide |

-continued

| Structure | Name |
|---|---|
| | (E)-3-(4-methoxyphenyl)-N-phenyl-N-tetrahydrothiophen-3-yl-prop-2-enamide |
| | 2-(4-methylphenoxy)-N-phenyl-N-tetrahydrothiophen-3-yl-acetamide |
| | 2-(4-methoxyphenoxy)-N-phenyl-N-tetrahydrothiophen-3-yl-acetamide |
| | (E)-N,3-diphenyl-N-tetrahydrothiophen-3-yl-prop-2-enamide |
| | 2-(4-ethoxyphenoxy)-N-phenyl-N-tetrahydrothiophen-3-yl-acetamide |
| | (E)-3-(4-ethoxyphenyl)-N-phenyl-N-tetrahydrothiophen-3-yl-prop-2-enamide |
| | 2-(3-methylphenoxy)-N-phenyl-N-tetrahydrothiophen-3-yl-acetamide |

| Structure | Name |
|---|---|
| | 2-(1,3-benzodioxol-5-yloxy)-N-phenyl-N-tetrahydrothiophen-3-yl-acetamide |
| | (E)-3-(3,4-dimethoxyphenyl)-N-phenyl-N-tetrahydrothiophen-3-yl-prop-2-enamide |
| | 2-(2-methylphenoxy)-N-phenyl-N-tetrahydrothiophen-3-yl-acetamide |
| 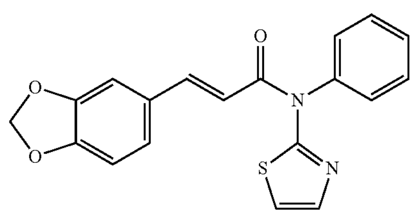 [SMILES: O=C(/C=C/c1ccc2c(c1)OCO2)N(c1ccccc1)c1nccs1] | (E)-3-(1,3-benzodioxol-5-yl)-N-phenyl-N-thiazol-2-yl-prop-2-enamide |
| 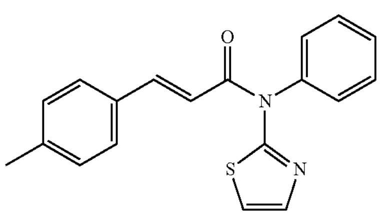 [SMILES: Cc1ccc(/C=C/C(=O)N(c2ccccc2)c2nccs2)cc1] | (E)-N-phenyl-3-(p-tolyl)-N-thiazol-2-yl-prop-2-enamide |
| 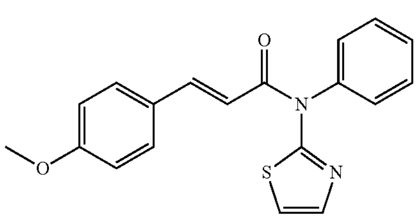 [SMILES: COc1ccc(/C=C/C(=O)N(c2ccccc2)c2nccs2)cc1] | (E)-3-(4-methoxyphenyl)-N-phenyl-N-thiazol-2-yl-prop-2-enamide |
| 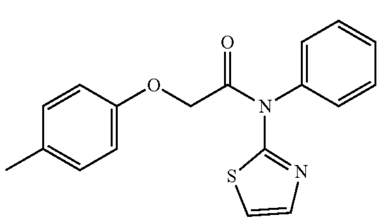 [SMILES: Cc1ccc(OCC(=O)N(c2ccccc2)c2nccs2)cc1] | 2-(4-methylphenoxy)-N-phenyl-N-thiazol-2-yl-acetamide |

| Structure | Name |
|---|---|
| 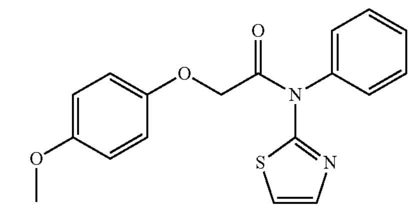 [SMILES: COc1ccc(OCC(=O)N(c2ccccc2)c2nccs2)cc1] | 2-(4-methoxyphenoxy)-N-phenyl-N-thiazol-2-yl-acetamide |
| 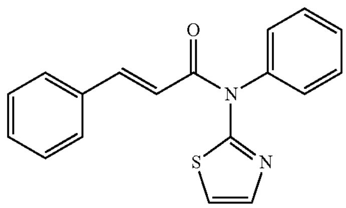 [SMILES: O=C(/C=C/c1ccccc1)N(c1ccccc1)c1nccs1] | (E)-N,3-diphenyl-N-thiazol-2-yl-prop-2-enamide |
| 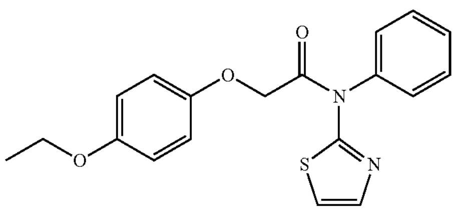 [SMILES: CCOc1ccc(OCC(=O)N(c2ccccc2)c2nccs2)cc1] | 2-(4-ethoxyphenoxy)-N-phenyl-N-thiazol-2-yl-acetamide |
| 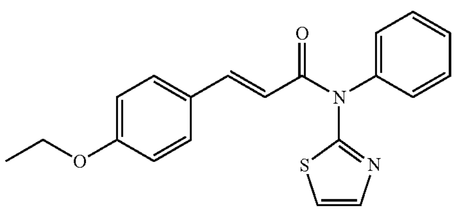 [SMILES: CCOc1ccc(/C=C/C(=O)N(c2ccccc2)c2nccs2)cc1] | (E)-3-(4-ethoxyphenyl)-N-phenyl-N-thiazol-2-yl-prop-2-enamide |
| 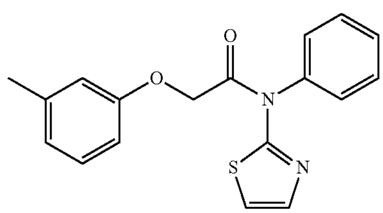 [SMILES: Cc1cccc(OCC(=O)N(c2ccccc2)c2nccs2)c1] | 2-(3-methylphenoxy)-N-phenyl-N-thiazol-2-yl-acetamide |
| 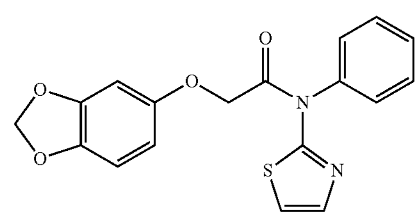 [SMILES: O=C(COc1ccc2c(c1)OCO2)N(c1ccccc1)c1nccs1] | 2-(1,3-benzodioxol-5-yloxy)-N-phenyl-N-thiazol-2-yl-acetamide |
| 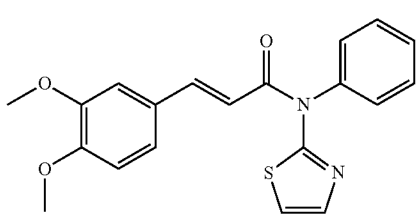 [SMILES: COc1ccc(/C=C/C(=O)N(c2ccccc2)c2nccs2)cc1OC] | (E)-3-(3,4-dimethoxy-phenyl)-N-phenyl-N-thiazol-2-yl-prop-2-enamide |

| Structure | Name |
|---|---|
| 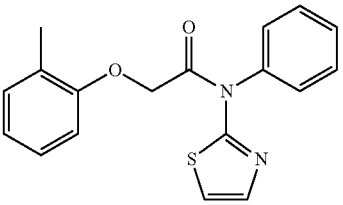 | 2-(2-methylphenoxy)-N-phenyl-N-thiazol-2-yl-acetamide |
| 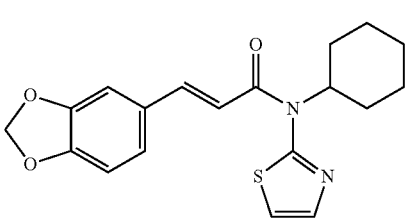 [SMILES: O=C(/C=C/c1ccc2c(c1)OCO2)N(c1nccs1)C1CCCCC1] | (E)-3-(1,3-benzodioxol-5-yl)-N-cyclohexyl-N-thiazol-2-yl-prop-2-enamide |
| 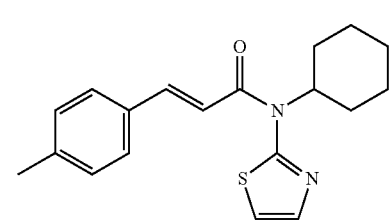 [SMILES: Cc1ccc(/C=C/C(=O)N(c2nccs2)C2CCCCC2)cc1] | (E)-N-cyclohexyl-3-(p-tolyl)-N-thiazol-2-yl-prop-2-enamide |
| 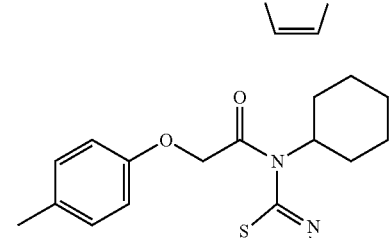 | (E)-N-cyclohexyl-3-(4-methoxyphenyl)-N-thiazol-2-yl-prop-2-enamide |
| 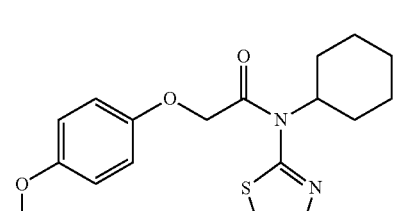 | N-cyclohexyl-2-(4-methylphenoxy)-N-thiazol-2-yl-acetamide |
| 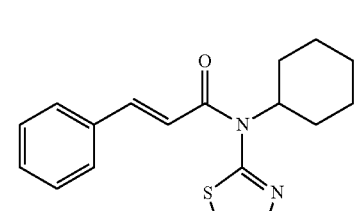 | N-cyclohexyl-2-(4-methoxphenoxy)-N-thiazol-2-yl-acetamide |
| 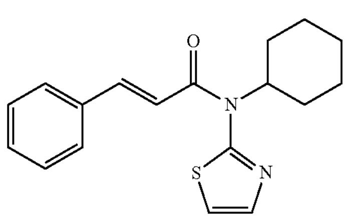 [SMILES: O=C(/C=C/c1ccccc1)N(c1nccs1)C1CCCCC1] | (E)-N-cyclohexyl-3-phenyl-N-thiazol-2-yl-prop-2-enamide |

-continued

| Structure | Name |
|---|---|
| 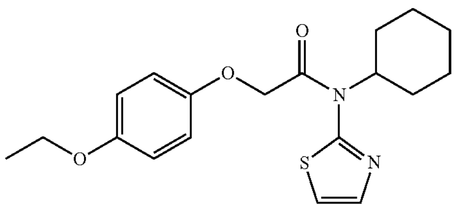 [SMILES: CCOc1ccc(OCC(=O)N(c2nccs2)C2CCCCC2)cc1] | N-cyclohexyl-2-(4-ethoxy-phenoxy)-N-thiazol-2-yl-acetamide |
| 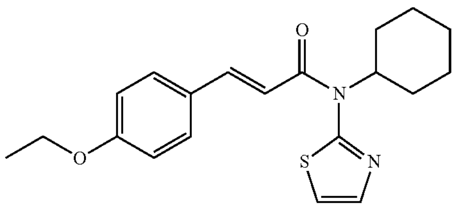 [SMILES: CCOc1ccc(/C=C/C(=O)N(c2nccs2)C2CCCCC2)cc1] | (E)-N-cyclohexyl-3-(4-ethoxyphenyl)-N-thiazol-2-yl-prop-2-enamide |
| 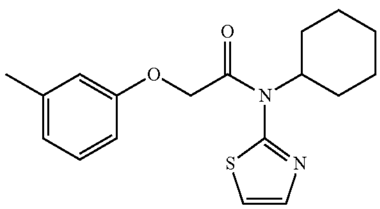 [SMILES: Cc1cccc(OCC(=O)N(c2nccs2)C2CCCCC2)c1] | N-cyclohexyl-2-(3-methylphenoxy)-N-thiazol-2-yl-acetamide |
| 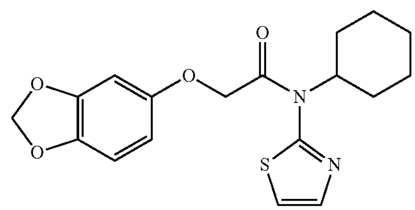 [SMILES: O=C(COc1ccc2c(c1)OCO2)N(c1nccs1)C1CCCCC1] | 2-(1,3-benzodioxol-5-yloxy)-N-cyclohexyl-N-thiazol-2-yl-acetamide |
| 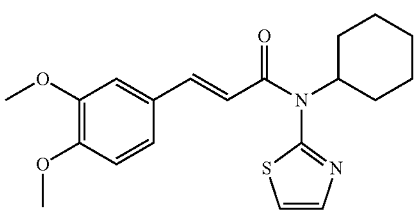 [SMILES: COc1ccc(/C=C/C(=O)N(c2nccs2)C2CCCCC2)cc1OC] | (E)-N-cyclohexyl-3-(3,4-dimethoxyphenyl)-N-thiazol-2-yl-prop-2-enamide |
| 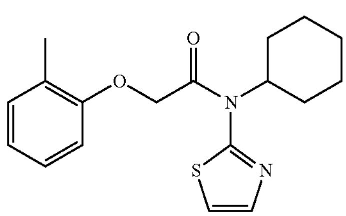 [SMILES: Cc1ccccc1OCC(=O)N(c1nccs1)C1CCCCC1] | N-cyclohexyl-2-(2-methylphenoxy)-N-thiazol-2-yl-acetamide |
| 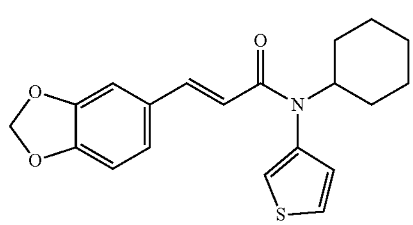 [SMILES: O=C(/C=C/c1ccc2c(c1)OCO2)N(c1ccsc1)C1CCCCC1] | (E)-3-(1,3-benzodioxol-5-yl)-N-cyclohexyl-N-(3-thienyl)prop-2-enamide |

| Structure | Name |
|---|---|
| 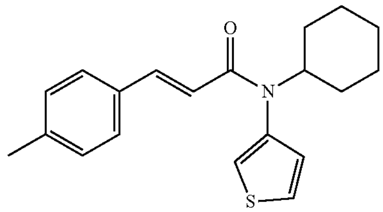 [SMILES: Cc1ccc(/C=C/C(=O)N(c2ccsc2)C2CCCCC2)cc1] | (E)-N-cyclohexyl-3-(p-tolyl)-N-(3-thienyl)prop-2-enamide |
| 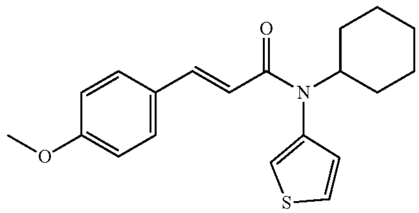 [SMILES: COc1ccc(/C=C/C(=O)N(c2ccsc2)C2CCCCC2)cc1] | (E)-N-cyclohexyl-3-(4-methoxyphenyl)-N-(3-thienyl)prop-2-enamide |
| 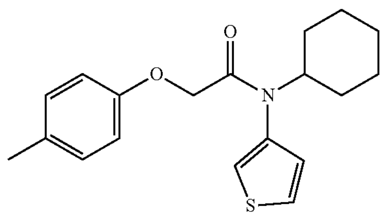 [SMILES: Cc1ccc(OCC(=O)N(c2ccsc2)C2CCCCC2)cc1] | N-cyclohexyl-2-(4-methylphenoxy)-N-(3-thienyl)acetamide |
| 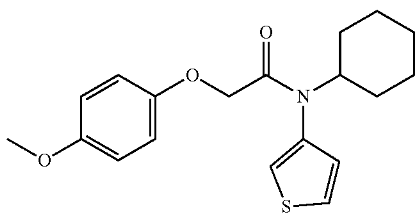 [SMILES: COc1ccc(OCC(=O)N(c2ccsc2)C2CCCCC2)cc1] | N-cyclohexyl-2-(4-methoxyphenoxy)-N-(3-thienyl)acetamide |
| 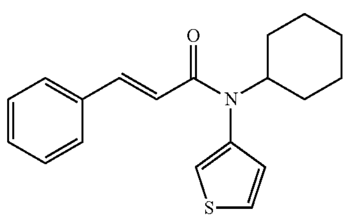 [SMILES: O=C(/C=C/c1ccccc1)N(c1ccsc1)C1CCCCC1] | (E)-N-cyclohexyl-3-phenyl-N-(3-thienyl)prop-2-enamide |
| | N-cyclohexyl-2-(4-ethoxyphenoxy)-N-(3-thienyl)acetamide |
| 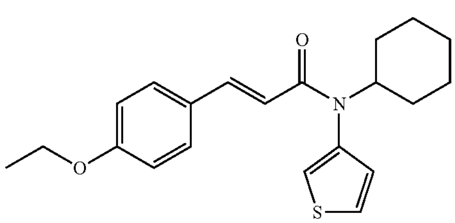 [SMILES: CCOc1ccc(/C=C/C(=O)N(c2ccsc2)C2CCCCC2)cc1] | (E)-N-cyclohexyl-3-(4-ethoxyphenyl)-N-(3-thienyl)prop-2-enamide |

| Structure | Name |
|---|---|
| 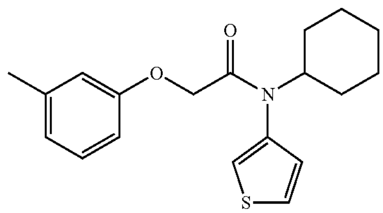 [SMILES: Cc1cccc(OCC(=O)N(c2ccsc2)C2CCCCC2)c1] | N-cyclohexyl-2-(3-methylphenoxy)-N-(3-thienyl)acetamide |
| 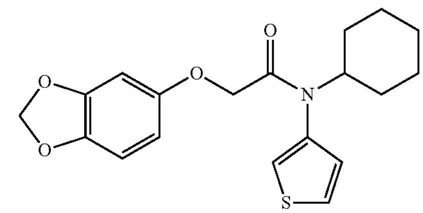 [SMILES: O=C(COc1ccc2c(c1)OCO2)N(c1ccsc1)C1CCCCC1] | 2-(1,3-benzodioxol-5-yloxy)-N-cyclohexyl-N-(3-thienyl)acetamide |
| 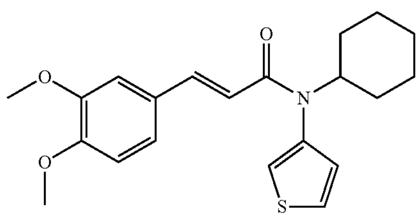 [SMILES: COc1ccc(/C=C/C(=O)N(c2ccsc2)C2CCCCC2)cc1OC] | (E)-N-cyclohexyl-3-(3,4-dimethoxyphenyl)-N-(3-thienyl)prop-2-enamide |
| 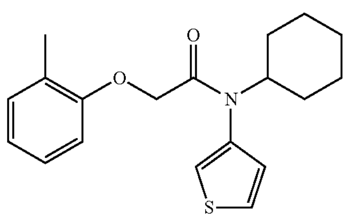 [SMILES: Cc1ccccc1OCC(=O)N(c1ccsc1)C1CCCCC1] | N-cyclohexyl-2-(2-methylphenoxy)-N-(3-thienyl)acetamide |
| 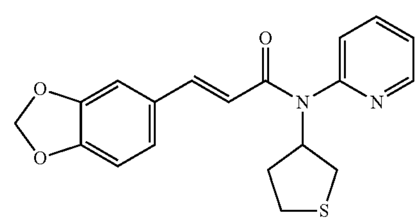 [SMILES: O=C(/C=C/c1ccc2c(c1)OCO2)N(c1ccccn1)C1CCSC1] | (E)-3-(1,3-benzodioxol-5-yl)-N-(2-pyridyl)-N-tetrahydrothiophen-3-yl-prop-2-enamide |
| 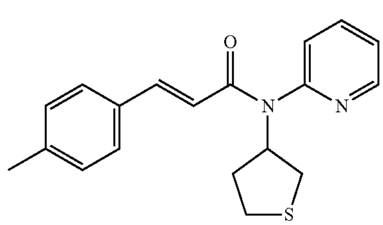 | (E)-3-(p-tolyl)-N-(2-pyridyl)-N-tetrahydrothiophen-3-yl-prop-2-enamide |
| 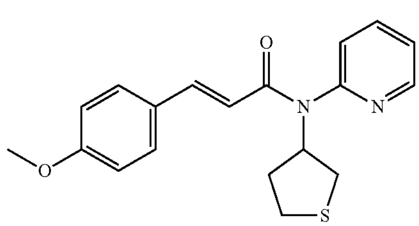 [SMILES: COc1ccc(/C=C/C(=O)N(c2ccccn2)C2CCSC2)cc1] | (E)-3-(4-methoxyphenyl)-N-(2-pyridyl)-N-tetrahydrothiophen-3-yl-prop-2-enamide |

| Structure | Name |
|---|---|
| | 2-(4-methylphenoxy)-N-(2-pyridyl)-N-tetrahydrothiophen-3-yl-acetamide |
| | 2-(4-methoxyphenoxy)-N-(2-pyridyl)-N-tetrahydrothiophen-3-yl-acetamide |
| | (E)-3-phenyl-N-(2-pyridyl)-N-tetrahydrothiophen-3-yl-prop-2-enamide |
| | 2-(4-ethoxyphenoxy)-N-(2-pyridyl)-N-tetrahydrothiophen-3-yl-acetamide |
| | (E)-3-(4-ethoxyphenyl)-N-(2-pyridyl)-N-tetrahydrothiophen-3-yl-prop-2-enamide |
| | 2-(3-methylphenoxy)-N-(2-pyridyl)-N-tetrahydrothiophen-3-yl-acetamide |
| | 2-(1,3-benzodioxol-5-yloxy)-N-(2-pyridyl)-N-tetrahydrothiophen-3-yl-acetamide |

| Structure | Name |
|---|---|
| 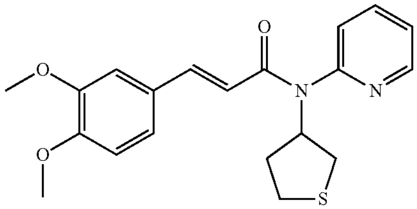 [SMILES: COc1ccc(/C=C/C(=O)N(c2ccccn2)C2CCSC2)cc1OC] | (E)-3-(3,4-dimethoxy-phenyl)-N-(2-pyridyl)-N-tetrahydrothiophen-3-yl-prop-2-enamide |
| 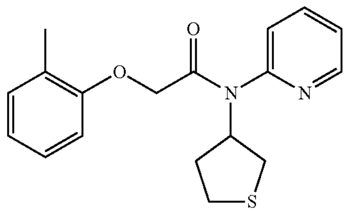 [SMILES: Cc1ccccc1OCC(=O)N(c1ccccn1)C1CCSC1] | 2-(2-methylphenoxy)-N-(2-pyridyl)-N-tetrahydro-thiophen-3-yl-acetamide |
| 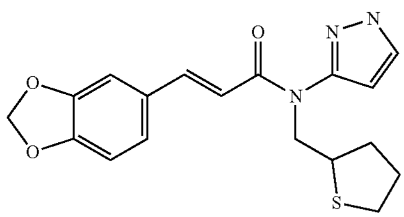 [SMILES: O=C(/C=C/c1ccc2c(c1)OCO2)N(CC1CCCS1)c1cc[nH]n1] | (E)-3-(1,3-benzodioxol-5-yl)-N-(1H-pyrazol-3-yl)-N-(tetrahydrothiophen-2-ylmethyl)prop-2-enamide |
| 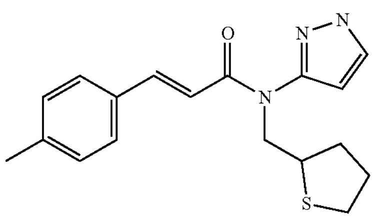 [SMILES: Cc1ccc(/C=C/C(=O)N(CC2CCCS2)c2cc[nH]n2)cc1] | (E)-3-(p-tolyl)-N-(1H-pyrazol-3-yl)-N-(tetrahydro-thiophen-2-ylmethyl)prop-2-enamide |
| 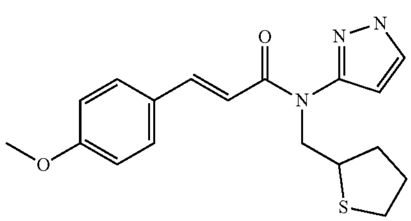 [SMILES: COc1ccc(/C=C/C(=O)N(CC2CCCS2)c2cc[nH]n2)cc1] | (E)-3-(4-methoxyphenyl)-N-(1H-pyrazol-3-yl)-N-(tetrahydrothiophen-2-yl-methyl)prop-2-enamide |
| 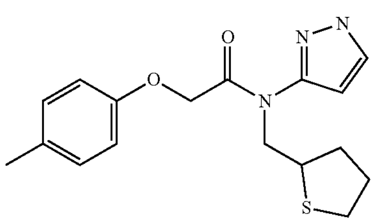 [SMILES: Cc1ccc(OCC(=O)N(CC2CCCS2)c2cc[nH]n2)cc1] | 2-(4-methylphenoxy)-N-(1H-pyrazol-3-yl)-N-(tetrahydrothiophen-2-ylmethyl)acetamide |
| 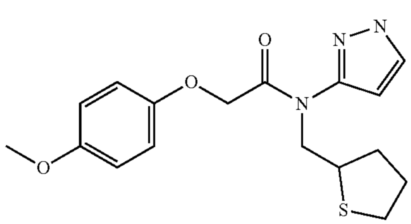 [SMILES: COc1ccc(OCC(=O)N(CC2CCCS2)c2cc[nH]n2)cc1] | 2-(4-methoxyphenoxy)-N-(1H-pyrazol-3-yl)-N-(tetra-hydrothiophen-2-yl-methyl)acetamide |

| Structure | Name |
|---|---|
| | (E)-3-phenyl-N-(1H-pyrazol-3-yl)-N-(tetrahydrothiophen-2-ylmethyl)prop-2-enamide |
| | 2-(4-ethoxyphenoxy)-N-(1H-pyrazol-3-yl)-N-(tetrahydrothiophen-2-yl-methyl)acetamide |
| | (E)-3-(4-ethoxyphenyl)-N-(1H-pyrazol-3-yl)-N-(tetrahydrothiophen-2-yl-methyl)prop-2-enamide |
| | 2-(3-methylphenoxy)-N-(1H-pyrazol-3-yl)-N-(tetrahydrothiophen-2-yl-methyl)acetamide |
| | 2-(1,3-benzodioxol-5-yloxy)-N-(1H-pyrazol-3-yl)-N-(tetrahydrothiophen-2-ylmethyl)acetamide |
| | (E)-3-(3,4-dimethoxyphenyl)-N-(1H-pyrazol-3-yl)-N-(tetrahydrothiophen-2-ylmethyl)prop-2-enamide |
| | 2-(2-methylphenoxy)-N-(1H-pyrazol-3-yl)-N-(tetrahydrothiophen-2-yl-methyl)acetamide |

-continued

| Structure | Name |
|---|---|
| 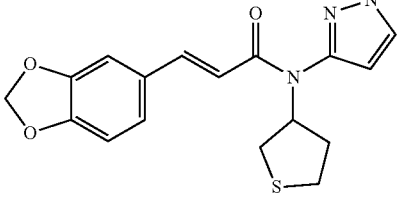 | (E)-3-(1,3-benzodioxol-5-yl)-N-(1H-pyrazol-3-yl)-N-tetrahydrothiophen-3-yl-prop-2-enamide |
| 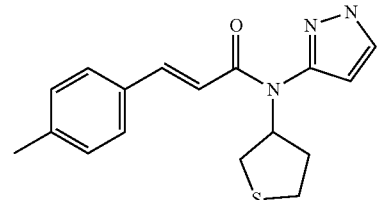 | (E)-3-(p-tolyl)-N-(1H-pyrazol-3-yl)-N-tetrahydrothio-phen-3-yl-prop-2-enamide |
| 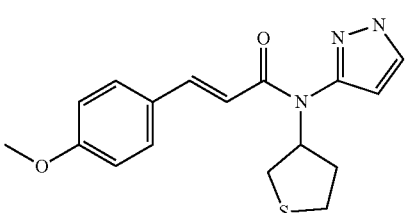 | (E)-3-(4-methoxyphenyl)-N-(1H-pyrazol-3-yl)-N-tetrahydrothiophen-3-yl-prop-2-enamide |
| 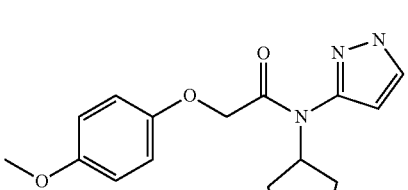 | 2-(4-methoxphenoxy)-N-(1H-pyrazol-3-yl)-N-tetra-hydrothiophen-3-yl-acetamide |
| 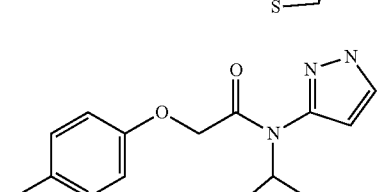 | 2-(4-methylphenoxy)-N-(1H-pyrazol-3-yl)-N-tetra-hydrothiophen-3-yl-acetamide |
| 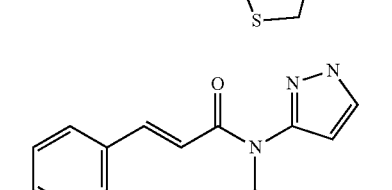 | (E)-3-phenyl-N-(1H-pyra-zol-3-yl)-N-tetrahydrothiophen-3-yl-prop-2-enamide |
| 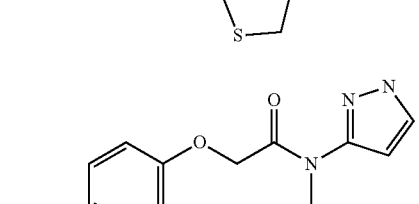 | 2-(4-ethoxyphenoxy)-N-(1H-pyrzol-3-yl)-N-tetrahydrothiophen-3-yl-acetamide |

| Structure | Name |
|---|---|
| | (E)-3-(4-ethoxyphenyl)-N-(1H-pyrazol-3-yl)-N-tetrahydrothiophen-3-yl-prop-2-enamide |
| | 2-(3-methylphenoxy)-N-(1H-pyrazol-3-yl)-N-tetrahydrothiophen-3-yl-acetamide |
| | 2-(1,3-benzodioxol-5-yloxy)-N-(1H-pyrazol-3-yl)-N-tetrahydrothiophen-3-yl-acetamide |
| | (E)-3-(3,4-dimethoxyphenyl)-N-(1H-pyrazol-3-yl)-N-tetrahydrothiophen-3-yl-prop-2-enamide |
| | 2-(2-methylphenoxy)-N-(1H-pyrazol-3-yl)-N-tetrahydrothiophen-3-yl-acetamide |
| | (E)-3-(1,3-benzodioxol-5-yl)-N-ethyl-N-(tetrahydrofuran-2-ylmethyl)prop-2-enamide |
| | (E)-N-ethyl-3-(p-tolyl)-N-(tetrahydrofuran-2-ylmethyl)prop-2-enamide |
| | (E)-N-ethyl-3-(4-methoxyphenyl)-N-(tetrahydrofuran-2-ylmethyl)prop-2-enamide |

-continued

| Structure | Name |
|---|---|
| 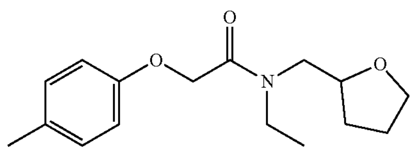 [SMILES: CCN(CC1CCCO1)C(=O)COc1ccc(C)cc1] | N-ethyl-2-(4-methyl-phenoxy)-N-(tetrahydrofuran-2-ylmethyl)acetamide |
| 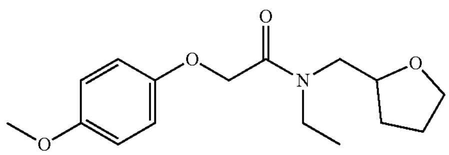 [SMILES: CCN(CC1CCCO1)C(=O)COc1ccc(OC)cc1] | N-ethyl-2-(4-methoxy-phenoxy)-N-(tetrahydrofuran-2-ylmethyl)acetamide |
| 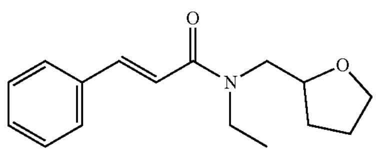 [SMILES: CCN(CC1CCCO1)C(=O)/C=C/c1ccccc1] | (E)-N-ethyl-3-phenyl-N-(tetrahydrofuran-2-yl-methyl)prop-2-enamide |
| 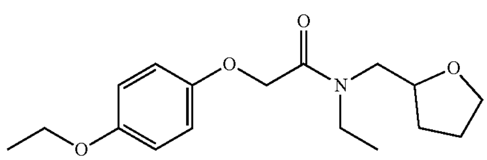 [SMILES: CCOc1ccc(OCC(=O)N(CC)CC2CCCO2)cc1] | 2-(4-ethoxyphenoxy)-N-ethyl-N-(tetrahydrofuran-2-ylmethyl)acetamide |
| 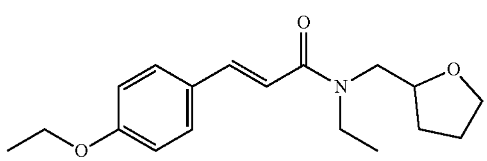 [SMILES: CCOc1ccc(/C=C/C(=O)N(CC)CC2CCCO2)cc1] | (E)-3-(4-ethoxyphenyl)-N-ethyl-N-(tetrahydrofuran-2-ylmethyl)prop-2-enamide |
| 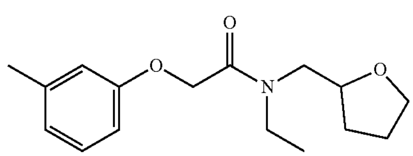 [SMILES: CCN(CC1CCCO1)C(=O)COc1cccc(C)c1] | N-ethyl-2-(3-methyl-phenoxy)-N-(tetrahydrofuran-2-ylmethyl)acetamide |
| 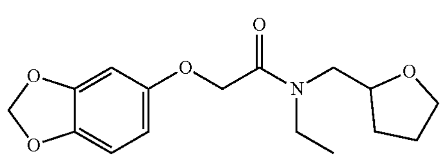 [SMILES: CCN(CC1CCCO1)C(=O)COc1ccc2c(c1)OCO2] | 2-(1,3-benzodioxol-5-yloxy)-N-ethyl-N-(tetra-hydrofuran-2-ylmethyl)acetamide |
| 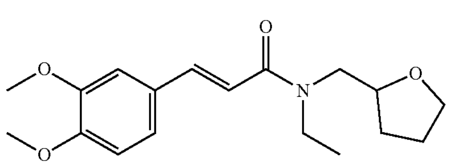 [SMILES: CCN(CC1CCCO1)C(=O)/C=C/c1ccc(OC)c(OC)c1] | (E)-3-(3,4-dimethoxy-phenyl)-N-ethyl-N-(tetra-hydrofuran-2-yl-methyl)prop-2-enamide |
| 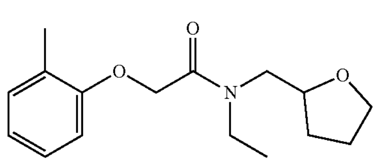 [SMILES: CCN(CC1CCCO1)C(=O)COc1ccccc1C] | N-ethyl-2-(2-methyl-phenoxy)-N-(tetrahydrofuran-2-ylmethyl)acetamide |

| Structure | Name |
|---|---|
| | (E)-3-(1,3-benzodioxol-5-yl)-N-phenyl-N-(tetra-hydrofuran-2-ylmethyl)prop-2-enamide |
| | (E)-N-phenyl-3-(p-tolyl)-N-(tetrahydrofuran-2-yl-methyl)prop-2-enamide |
| | (E)-3-(4-methoxyphenyl)-N-phenyl-N-(tetrahydro-furan-2-ylmethyl)prop-2-enamide |
| | 2-(4-methylphenoxy)-N-phenyl-N-(tetrahydro-furan-2-ylmethyl)acetamide |
| | 2-(4-methoxphenoxy)-N-phenyl-N-(tetrahydro-furan-2-ylmethyl)acetamide |
| | (E)-N,3-diphenyl-N-(tetra-hydrofuran-2-yl-methyl)prop-2-enamide |
| | 2-(4-ethoxyphenoxy)-N-phenyl-N-(tetrahydro-furan-2-ylmethyl)acetamide |

-continued

| Structure | Name |
|---|---|
| | (E)-3-(4-ethoxyphenyl)-N-phenyl-N-(tetrahydrofuran-2-ylmethyl)prop-2-enamide |
| | 2-(3-methylphenoxy)-N-phenyl-N-(tetrahydrofuran-2-ylmethyl)acetamide |
| | 2-(1,3-benzodioxol-5-yloxy)-N-phenyl-N-(tetrahydrofuran-2-ylmethyl)acetamide |
| | (E)-3-(3,4-dimethoxyphenyl)-N-phenyl-N-(tetrahydrofuran-2-yl-methyl)prop-2-enamide |
| | 2-(2-methylphenoxy)-N-phenyl-N-(tetrahydrofuran-2-ylmethyl)acetamide |

In an alternative embodiment of the present invention, the compounds of group D, as described above, are compounds for use with preference within the context of the present invention.

In a further alternative embodiment, the compounds of group E, as described above, are compounds for use with preference within the context of the present invention.

In a method of the invention, especially in its preferred configuration, the receptor is preferably contacted with at least one modulator which, in a cellular activity test using cells that recombinantly express the human TRPM8 receptor, modulates the permeability of these cells for $Ca^{2+}$ ions.

In a method of the invention, preferably in an embodiment described above as preferred, the modulator has agonistic or antagonistic action on the cellular $Ca^{2+}$ ion permeability.

Particular preference is given to an execution of a method of the invention, especially a preferred configuration, wherein the modulator is a TRPM8 receptor agonist.

A further aspect of the present invention comprises the use of a modulator of the invention, especially in one or more of the preferred methods, for non-therapeutic induction of a cold sensation in man and/or animals.

Preferably, such a modulator of the invention in the above-described use is preferably used for non-therapeutic induction of a cold sensation via a packing or textile comprising the modulator. In one alternative of the use of the invention, preference is given to using a composition comprising at least one, two, three or more of the modulators of the invention, especially of the preferred configurations, preferably in a (total) amount of 0.1 ppm to 10% by weight, based on the total weight of the composition, to achieve a cooling effect on the skin or mucosa that has preferably been prolonged compared to the cooling effect of a composition of the same constitution in which the modulator(s) has/have merely been exchanged for N-ethylmenthanecarboxamide, preferably in the same concentration, preferably by at least 10 minutes, and/or a cooling effect that sets in earlier compared to the cooling effect of a composition of the same constitution in which the modulator(s) has/have merely been exchanged for FEMA 4809 or FEMA 4496, preferably in the same concentration.

In order to quantify the long-lasting cooling effect of the compounds to be used in accordance with the invention, preference is given to conducting comparative experiments with N-ethylmenthane-3-carboxamide (as described above).

Preferably, the modulator(s) of the invention is/are for one of the uses described as preferred, selected from the respectively already described group A, group B or group C, or in another embodiment group D or group E.

A further aspect of the present invention relates to a modulator as described above for use as modulator of the TRPM8 receptor, preferably for use in a therapeutic method of modulating the TRPM8 receptor.

The present invention additionally relates to new compounds of structure type 1 per se. More particularly, the present invention relates to compounds selected from group A, group B or group C, or group D or group E, as respectively described herein, or a salt of such a compound, especially selected from acid addition salts with inorganic or especially organic, mono- or especially polybasic carboxylic acids.

The present invention additionally relates, irrespective of the uses described herein, to compositions comprising novel compounds of structure type 1, especially compounds selected from group A, group B or group C, or group D or group E, as respectively described herein.

A further aspect of the present invention relates to a composition comprising at least one modulator as described above for use as modulator of the TRPM8 receptor, preferably for use in a therapeutic method of modulating the TRPM8 receptor.

In a preferred embodiment, such a composition of the invention is for use as a modulator of the TRPM8 receptor, preferably for use in a therapeutic method of modulating the TRPM8 receptor, selected from the group consisting of
- a) foods, preferably ice cream, mousse, cream, drinks and confectionery,
- b) oral care products, preferably toothpaste, mouthwash and chewing gum,
- c) personal care products, preferably skincare or haircare products, for example sun cream, sunburn cream, lotions and shampoos, and patches,
- d) foams and gels.

In a particularly preferred embodiment, a composition of the invention is for use as a modulator of the TRPM8 receptor, preferably for use in a therapeutic method of modulating the TRPM8 receptor, especially in an embodiment described above as preferred, selected from the group consisting of aroma mixtures and formulations for nutrition, oral hygiene or enjoyment purposes or cosmetic formulations, comprising one, two, three or more of the modulators as described above, wherein said modulator(s) is/are present in a (total) amount of 0.05 ppm to 10% by weight, preferably of 0.1 ppm to 10% by weight, based on the total weight of the aroma mixture or formulation.

Preferably, such a composition of the invention for use as a modulator of the TRPM8 receptor, preferably for use in a therapeutic method of modulating the TRPM8 receptor, additionally comprises:
- (1) one or more further substances having physiological cooling action, wherein the further substance or one, more than one or all of the further substances (i) cause(s) a flavoring effect or (ii) do(es) not cause a flavoring effect, and/or
- (2) one or more aromas with no physiological cooling effect and/or
- (3) one or more substances having a trigeminal or mouthwatering effect with no physiological cooling effect and/or
- (4) (iii) one compound or (iv) two or more compounds which, independently or collectively in case (iv), additionally cause(s) a flavor-modulating effect and/or a trigeminal and/or mouthwatering stimulus.

Further substances having a physiological cooling effect include, for example, those as described in WO 2014/090293 A1, preferably menthol, menthol compounds, Optamint or mint oils.

Menthol compounds are preferably selected from the group consisting of menthol, menthyl methyl ether, menthone glyceryl acetal (Frescolat® MGA, FEMA GRAS 3807), menthone glyceryl ketal (FEMA GRAS 3808), menthyl lactate (Frescolat® ML, FEMA GRAS 3748), menthol ethylene glycol carbonate (Fresolcat® MGC, FEMA GRAS 3805), menthol propylene glycol carbonate (Frescolat® MPC, FEMA GRAS 3806), menthyl N-ethyloxamate (Frescolat®), monomethyl succinate (FEMA GRAS 3810), monomethyl glutarate (FEMA GRAS 4006), menthoxy-1,2-propanediol (FEMA GRAS 3784), menthoxy-2-methyl-1,2-propanediol (FEMA GRAS 3849) and menthanecarboxylic esters and -carboxamides, for example WS-3 (FEMA GRAS 3455), WS-5 (FEMA GRAS 4309), WS-12 (Frescolat® SC-1, FEMA GRAS 4681) and WS-23 (FEMA GRAS 3804), and mixtures thereof.

Optamint is a mixture of more than 50 different natural essential oils and natural or nature-identical aromas. Optamints have variable compositions of various (partly fractionated) oils which are preferably a mixture of, for example, different peppermint oils and spearmint oils, and Eucalyptus globulus oil, star anise oil, menthol, menthone, isomenthone, menthyl acetate, anethole, eucalyptol, etc. An exact statement of the composition of the Optamints is therefore not possible. The Optamint® product series is commercially available from Symrise AG.

In a preferred embodiment of the use of a modulator of the invention, especially in one or more of the preferred methods, for non-therapeutic induction of a cold sensation in man and/or animals for achieving a physiological cooling effect on the skin and/or mucosa, the cooling effect has been prolonged by at least 10 minutes compared to the cooling effect of a composition of the same constitution in which the modulator(s) has/have merely been exchanged for N-ethylmenthanecarboxamide, preferably in the same concentration, and/or the cooling effect sets in earlier compared to the cooling effect of a composition of the same constitution in which the modulator(s) has/have merely been exchanged for FEMA 4809 or FEMA 4496, preferably in the same concentration, comprising the following step:

applying an amount of a composition as described above, especially in one or more preferred embodiments, which is sufficient for achieving a physiological cooling effect to the skin and/or mucosa.

More preferably, the modulator(s) in such a use of the invention is/are selected from the above-described group A.

The actives of the invention have a broad field of use in human cosmetics and care, especially in skincare and haircare, but are also usable pharmacologically, and in foods and textile products, but also as repellents and as a constituent of insecticidal compositions.

The compositions of the invention may especially be skin-cosmetic, hair-cosmetic, dermatological, hygiene or pharmaceutical products. More particularly, the actives of the invention, especially having a cooling effect, are employed for skin cosmetics and/or hair cosmetics or as oral care compositions.

The haircare or skincare compositions or formulations of the invention are especially in the form of an emulsion, a dispersion, a suspension, in the form of an aqueous surfactant preparation, a milk, a lotion, a cream, a balsam, an ointment, a gel, granules, a powder, a stick preparation, for example a lipstick, a foam, an aerosol or a spray. Such formulations are highly suitable for topical preparations. Suitable emulsions are oil-in-water emulsions and water-in-oil emulsions or microemulsions.

In general, the hair- or skin-cosmetic formulation is used for application to the skin (topical) or the hair. "Topical preparations" are understood here to mean those formulations suitable for applying the actives to the skin in fine distribution, for example in a form absorbable through the skin. Suitable examples for this purpose are aqueous and aqueous-alcoholic solutions, sprays, foams, foam aerosols, ointments, aqueous gels, emulsions of the O/W or W/O type, microemulsions or cosmetic stick preparations.

In one embodiment of the cosmetic composition of the invention, this comprises a carrier. Preferred carriers are water, a gas, a water-based liquid, an oil, a gel, an emulsion or microemulsion, a dispersion or a mixture thereof. The specified carriers exhibit good skin compatibility. Aqueous gels, emulsions or microemulsions are particularly advantageous for topical preparations.

The teaching of the invention also comprises the use of the actives described herein in pharmaceutical products for treatment of an individual, preferably a mammal, especially a human, farm animal or domestic animal. For this purpose, the actives are administered in the form of pharmaceutical compositions comprising a pharmaceutically compatible excipient together with at least one active of the invention and optionally further actives. These compositions may be administered, for example, by an oral, rectal, transdermal, subcutaneous, intravenous, intramuscular or intranasal route.

Examples of suitable pharmaceutical formulations or compositions are solid medicament forms such as powders, granules, tablets, pastilles, sachets, cachets, sugar-coated tablets, capsules such as hard and soft gelatin capsules, suppositories or vaginal medicament forms, semisolid medicament forms such as ointments, creams, hydrogels, pastes or patches, and liquid medicament forms such as solutions, emulsions, especially oil-in-water emulsions, suspensions, for example lotions, injection and infusion formulations, eye and ear drops. Implanted release devices may also be used for administration of inhibitors of the invention. In addition, it is also possible to employ liposomes, microspheres or polymer matrices.

In the production of products or formulations or compositions of the invention, actives of the invention are usually mixed or diluted with an excipient. Excipients may be solid, semisolid or liquid materials which serve as a vehicle, carrier or medium for the active. The active ingredient content (of one or more actives of the invention present simultaneously) may vary here within a wide range and is, for instance, based in each case on the total weight of the composition, within the ppm range from about 0.05 ppm to 10% by weight, preferably 0.1 ppm to 10% by weight.

Suitable excipients include, for example, lactose, dextrose, sucrose, sorbitol, mannitol, starches, acacia gum, calcium phosphate, alginates, tragacanth, gelatin, calcium silicate, microcrystalline cellulose, polyvinylpyrrolidone, cellulose, water, syrup and methyl cellulose. In addition, the formulations may comprise pharmaceutically acceptable carriers or customary auxiliaries, such as lubricants, for example tallow, magnesium stearate and mineral oil; wetting agents; emulsifying and suspending agents; preservatives, such as methyl and propyl hydroxybenzoates; antioxidants; antiirritants; chelating agents; coating auxiliaries; emulsion stabilizers; film formers; gel formers; odor maskers; taste correctors; resins; hydrocolloids; solvents; solubilizers; neutralizing agents; permeation accelerators; pigments; quaternary ammonium compounds; refatting and superfatting agents; ointment, cream or oil bases; silicone derivatives; spreading auxiliaries; stabilizers; sterilants; suppository bases; tableting auxiliaries, such as binders, fillers, lubricants, disintegrants or coatings; propellants; desiccants; opacifiers; thickeners; waxes; plasticizers; white oils. This kind of configuration is based on specialist knowledge, as represented, for example, in Fiedler, H. P. Lexikon der Hilfsstoffe für Pharmazie, Kosmetik und angrenzende Gebiete [Lexicon of Auxiliaries for Pharmacy, Cosmetics and Related Fields], 4th edition, Aulendorf: ECV-Editio-Kantor-Verlag, 1996, or Hager's Handbuch der Pharmazeutischen Praxis [Hager's Handbook of Pharmaceutical Practice], Springer Verlag, Heidelberg.

The compositions of the invention may, as well as customary additives or auxiliaries, additionally comprise cosmetic and/or dermatological and/or pharmacological actives.

Non-limiting examples of suitable further actives include:

Suitable cosmetic and/or dermatological actives are, for example, coloring actives, skin and hair pigmentation agents, tinting agents, tanning agents, bleaches, keratin-hardening substances, antimicrobial actives, photofilter actives, repellent actives, hyperemic substances, keratolytic and keratoplastic substances, antidandruff actives, antiphlogistics, keratinizing substances, antioxidant actives and actives acting as free-radical scavengers, skin moisturizing or humectant substances, refatting actives, antierythematous or antiallergic actives, branched fatty acids, such as 18-methyleicosanoic acid, and mixtures thereof.

Artificial tanning actives suitable for tanning the skin without natural or artificial irradiation with UV rays; these are, for example, dihydroxyacetone, alloxan and walnutshell extract. Suitable keratin-hardening substances are generally actives as also used in antiperspirants, for example potassium aluminum sulfate, aluminum hydroxychloride, aluminum lactate, etc.

Antimicrobial actives that are used to destroy microorganisms or inhibit their growth. They thus serve both as preservatives and as deodorizing substance that reduces the development or intensity of body odor. These include, for example, customary preservatives known to those skilled in the art, such as p-hydroxybenzoic esters, imidazolidinylurea, formaldehyde, sorbic acid, benzoic acid, salicylic acid, etc. Examples of such deodorizing substances include zinc ricinoleate, triclosan, undecylenoic acid alkylolamides, triethyl citrate, chlorhexidine, etc.

Suitable auxiliaries and additives for producing hair cosmetic or skin cosmetic preparations are known to the person skilled in the art and can be found in handbooks of cosmetics, for example Schrader, Grundlagen und Rezepturen der Kosmetika [Fundamentals and Formulations of Cosmetics], Hüthig Verlag, Heidelberg, 1989, ISBN 3-7785-1491-1. The auxiliaries and additives are preferably cosmetically and/or pharmaceutically acceptable auxiliaries. Pharmaceutically acceptable auxiliaries are auxiliaries which are known for use in the field of pharmacy, food technology and related fields, in particular those listed in the relevant pharmacopoeia (e.g. DAB, Ph. Eur., BP, NF), and other auxiliaries whose properties do not preclude a physiological application.

Suitable auxiliaries may be: lubricants, wetting agents, emulsifying and suspending agents, preservatives, antioxidants, antiirritants, chelating agents, emulsion stabilizers, film formers, gel formers, odor maskers, hydrocolloids, solvents, solubilizers, neutralizing agents, permeation accelerators, pigments, quaternary ammonium compounds, refatting and superfatting agents, ointment, cream or oil bases, silicone derivatives, stabilizers, sterilants, propellants, desiccants, opacifiers, thickeners, waxes, plasticizers, white oils. This kind of configuration is based on specialist knowledge, as represented, for example, in Fiedler, H. P. Lexikon der Hilfsstoffe for Pharmazie, Kosmetik und angrenzende Gebiete, 4th ed., Aulendorf: ECV-Editio-Kantor-Verlag, 1996.

Further suitable additives are selected from perfume oils, hair polymers, hair and skin conditioners, graft polymers, water-soluble or dispersible silicone-containing polymers, light stabilizers, bleaches, care agents, colorants, tinting agents, tanning agents, dyes, bodying agents, humectants, refatting agents, collagen, protein hydrolyzates, lipids, antioxidants, defoamers, antistats, emollients, plasticizers, peroxide decomposers.

Examples of suitable auxiliaries and additives include:

(1) Antioxidants selected from amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl, and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximine, homocysteine sulfoximine, buthionine sulfone, penta-, hexa-, heptathionine sulfoximine), especially in very small, tolerated doses (e.g. pmol to μmol/kg range), and also (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives thereof (e.g. sodium ascorbate, ascorbyl palmitate, Mg ascorbylphosphate, ascorbyl acetate), tocopherol and derivatives (e.g. vitamin E acetate, tocotrienol), vitamin A and derivatives (vitamin A palmitate) and coniferyl benzoate of benzoin, rutic acid and derivatives thereof, α-glycosylrutine, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide).

(2) Peroxide decomposers, i.e. compounds capable of decomposing peroxides, more preferably lipid peroxides. These are understood to mean organic substances, for example pyridine-2-thiol-3-carboxylic acid, 2-methoxypyrimidinolcarboxylic acids, 2-methoxypyridinecarboxylic acids, 2-dimethylaminopyrimidinolcarboxylic acids, 2-dimethylaminopyridinecarboxylic acids.

(3) Thickeners such as crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. In particular, nonionic thickeners are used.

(4) Preservatives listed below with their E number:

| | |
|---|---|
| E 200 | Sorbic acid |
| E 201 | Sodium sorbate |
| E 202 | Potassium sorbate |
| E 203 | Calcium sorbate |
| E 210 | Benzoic acid |
| E 211 | Sodium benzoate |
| E 212 | Potassium benzoate |
| E 213 | Calcium benzoate |
| E 214 | Ethyl p-hydroxybenzoate |
| E 215 | Ethyl p-hydroxybenzoate Na salt |
| E 216 | n-Propyl p-hydroxybenzoate |
| E 217 | n-Propyl p-hydroxybenzoate Na salt |
| E 218 | Methyl p-hydroxybenzoate |
| E 219 | Methyl p-hydroxybenzoate Na salt |
| E 220 | Sulfur dioxide |
| E 221 | Sodium sulfite |
| E 222 | Sodium hydrogensulfite |
| E 223 | Sodium disulfite |
| E 224 | Potassium disulfite |
| E 226 | Calcium sulfite |
| E 227 | Calcium hydrogensulfite |
| E 228 | Potassium hydrogensulfite |
| E 230 | Biphenyl (Diphenyl) |
| E 231 | Orthophenylphenol |
| E 232 | Sodium orthophenylphenoxide |
| E 233 | Thiabendazole |
| E 235 | Natamycin |
| E 236 | Formic acid |
| E 237 | Sodium formate |
| E 238 | Calcium formate |
| E 239 | Hexamethylenetetramine |
| E 249 | Potassium nitrite |
| E 250 | Sodium nitrite |
| E 251 | Sodium nitrate |
| E 252 | Potassium nitrate |
| E 280 | Propionic acid |
| E 281 | Sodium propionate |
| E 282 | Calcium propionate |
| E 283 | Potassium propionate |
| E 290 | Carbon dioxide |

Also suitable in accordance with the invention are preservatives or preservative auxiliaries customary in cosmetics, such as dibromodicyanobutane (2-bromo-2-bromomethylglutaronitrile), 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol, formaldehyde emitters.

Also suitable as preservatives are phenyl hydroxyalkyl ethers, especially the compound known by the phenoxyethanol name, on account of its bactericidal and fungicidal effects on a number of microorganisms.

Other antimicrobial agents are also likewise suitable for incorporation into the preparations of the invention. Advantageous substances are, for example, 2,4,4'-trichloro-2'-hydroxydiphenyl ether (irgasan), 1,6-di(4-chlorophenylbiguanido)hexane (chlorhexidine), 3,4,4'-trichlorocarbanilide, quaternary ammonium compounds, clove oil, mint oil, thyme oil, triethyl citrate, farnesol (3,7,11-trimethyl-2,6,10-dodecatrien-1-ol), and the actives or active combinations described in the laid-open patent specifications DE-37 40 186, DE 39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE 196 02 111, DE-196 31 003, DE-196 31 004 and DE-196 34 019 and the patent specifications DE-42 29 737, DE-42 37 081, DE-43 24 219, DE-44 29 467, DE-44 23 410 and DE-195 16 705. Sodium hydrogencarbonate can also be used advantageously. Antimicrobial polypeptides can also likewise be used.

(5) Photofilter actives which absorb UV rays in the UV-B and/or UV-A region. Suitable UV filters are, for example, 2,4,6-triaryl-1,3,5-triazines in which the aryl groups may in each case bear at least one substituent which is preferably selected from hydroxy, alkoxy, specifically methoxy, alkoxycarbonyl, specifically methoxycarbonyl and ethoxycarbonyl, and mixtures thereof. Additionally suitable are p-aminobenzoic esters, cinnamic esters, benzophenones, camphor derivatives, and pigments which stop UV rays, such as titanium dioxide, talc and zinc oxide.

Useful UV filter substances include any desired UV-A and UV-B filter substances. Examples include:

| No | Substance | CAS No. (= acid) |
|---|---|---|
| 1 | 4-aminobenzoic acid | 150-13-0 |
| 2 | 3-(4'-trimethylammonium)benzylidenebornan-2-one methylsulfate | 52793-97-2 |
| 3 | 3,3,5-trimethylcyclohexyl salicylate (homosalate) | 118-56-9 |
| 4 | 2-hydroxy-4-methoxybenzophenone (oxybenzone) | 131-57-7 |
| 5 | 2-phenylbenzimidazole-5-sulfonic acid and its potassium, sodium and triethanolamine salts | 27503-81-7 |
| 6 | 3,3'-(1,4-phenylenedimethine)bis(7,7-dimethyl-2-oxobicyclo[2.2.1]heptane-1-methanesulfonic acid) and its salts | 90457-82-2 |
| 7 | polyethoxyethyl 4-bis(polyethoxy)aminobenzoate | 113010-52-9 |
| 8 | 2-ethylhexyl 4-dimethylaminobenzoate | 21245-02-3 |
| 9 | 2-ethylhexyl salicylate | 118-60-5 |
| 10 | 2-isoamyl 4-methoxycinnamate | 71617-10-2 |
| 11 | 2-ethylhexyl 4-methoxycinnamate | 5466-77-3 |
| 12 | 2-hydroxy-4-methoxybenzophenone-5-sulfonic acid (sulisobenzone) and the sodium salt | 4065-45-6 |
| 13 | 3-(4'-sulfobenzylidene)bornan-2-one and salts | 58030-58-6 |
| 14 | 3-benzylidenebornan-2-one | 16087-24-8 |
| 15 | 1-(4'-isopropylphenyl)-3-phenylpropane-1,3-dione | 63260-25-9 |
| 16 | 4-isopropylbenzyl salicylate | 94134-93-7 |
| 17 | 3-imidazol-4-ylacrylic acid and its ethyl ester | 104-98-3 |
| 18 | ethyl 2-cyano-3,3-diphenylacrylate | 5232-99-5 |
| 19 | 2'-ethylhexyl 2-cyano-3,3-diphenylacrylate | 6197-30-4 |
| 20 | menthyl-o-aminobenzoate or: 5-methyl 2-(1-methylethyl)-2-aminobenzoate | 134-09-8 |
| 21 | glyceryl p-aminobenzoate or: 1-glyceryl 4-aminobenzoate | 136-44-7 |
| 22 | 2,2'-dihydroxy-4-methoxybenzophenone (dioxybenzone) | 131-53-3 |
| 23 | 2-hydroxy-4-methoxy-4-methylbenzophenone (mexenone) | 1641-17-4 |
| 24 | triethanolamine salicylate | 2174-16-5 |
| 25 | dimethoxyphenylglyoxalic acid or: sodium 3,4-dimethoxyphenylglyoxalate | 4732-70-1 |
| 26 | 3-(4'-sulfobenzylidene)bornan-2-one and its salts | 56039-58-8 |
| 27 | 4-tert-butyl-4'-methoxydibenzoylmethane | 70356-09-1 |
| 28 | 2,2',4,4'-tetrahydroxybenzophenone | 131-55-5 |
| 29 | 2,2'-methylenebis[6-(2H-benzotriazol-2-yl)-4-(1,1,3,3-tetramethylbutyl)phenol] | 103597-45-1 |
| 30 | 2,2'-(1,4-phenylene)bis-1H-benzimidazole-4,6-disulfonic acid, Na salt | 180898-37-7 |
| 31 | 2,4-bis[4-(2-ethylhexyloxy)-2-hydroxy]phenyl-6-(4-methoxyphenyl)[1.3.5]triazine | 187393-00-6 |
| 32 | 3-(4-methylbenzylidene)camphor | 36861-47-9 |
| 33 | polyethoxyethyl 4-bis(polyethoxy) paraaminobenzoate | 113010-52-9 |
| 34 | 2,4-dihydroxybenzophenone | 131-56-6 |
| 35 | 2,2'-dihydroxy-4,4'-dimethoxybenzophenone-5,5'-disodium sulfonate | 3121-60-6 |
| 36 | 2-[4-(diethylamino)-2-hydroxybenzoyl]hexyl benzoate | 302776-68-7 |
| 37 | 2-(2H-benzotriazol-2-yl)-4-methyl-6-[2-methyl-3-[1,3,3,3-tetramethyl-1-[(trimethylsilyl)oxy]disiloxanyl]propyl]phenol | 155633-54-8 |
| 38 | 1,1[(2,2'-dimethylpropoxy)carbonyl]-4,4-diphenyl-1,3-butadiene | 363602-15-7 |

The cosmetic and dermatological compositions or formulations of the invention may advantageously also comprise inorganic pigments that stop UV rays, based on metal oxides and/or other sparingly water-soluble or water-insoluble metal compounds selected from the group of the oxides of zinc (ZnO), titanium (TiO$_2$), iron (e.g. Fe$_2$O$_3$), zirconium (ZrO$_2$), silicon (SiO$_2$), manganese (e.g. MnO), aluminum (Al$_2$O$_3$), cerium (e.g. Ce$_2$O$_3$), mixed oxides of the corresponding metals and blends of such oxides.

The inorganic pigments here may be in coated form, i.e. may have been surface-treated. This surface treatment can, for example, consist in providing the pigments with a thin hydrophobic layer by a method known per se, as described in DE-A-33 14 742.

(6) Repellent actives, i.e. compounds capable of warding off or driving away certain animals, particularly insects, from humans. These include, for example, 2-ethyl-1,3-hexanediol, N,N-diethyl-m-toluamide, etc.

(7) Suitable hyperemic substances, which stimulate perfusion of the skin, are, for example, essential oils, such as dwarf pine extract, lavender extract, rosemary extract, juniperberry extract, roast chestnut extract, birch leaf extract, hayseed extract, ethyl acetate, camphor, menthol, peppermint oil, rosemary extract, eucalyptus oil, etc.

(8) Suitable keratolytic and keratoplastic substances are, for example, salicylic acid, calcium thioglycolate, thioglycolic acid and its salts, sulfur, etc. Suitable antidandruff actives are, for example, sulfur, sulfur polyethylene glycol sorbitan monooleate, sulfur ricinol polyethoxylate, zinc pyrithione, aluminum pyrithione, etc.

(9) Suitable antiphlogistics, which counter skin irritation, are, for example, allantoin, bisabolol, Dragosantol, camomile extract, panthenol, etc.

(10) Cosmetically or pharmaceutically acceptable polymers, such as cationic, amphoteric and uncharged polymers.

Suitable polymers are, for example, cationic polymers with the INCI name Polyquaternium, e.g. copolymers of vinylpyrrolidone/N-vinylimidazolium salts (Luviquat FC, Luviquat HM, Luviquat MS, Luviquat Care), copolymers of N-vinylpyrrolidone/dimethylaminoethyl methacrylate, quaternized with diethyl sulfate (Luviquat PQ 11), copolymers of N-vinylcaprolactam/N-vinylpyrrolidone/N-vinylimidazolium salts (Luviquat E Hold), cationic cellulose derivatives (Polyquaternium-4 and -10), acrylamide copolymers (Polyquaternium-7) and chitosan.

Suitable cationic (quaternized) polymers are also Merquat (polymer based on dimethyldiallylammonium chloride), Gafquat (quaternary polymers formed by the reaction of polyvinylpyrrolidone with quaternary ammonium compounds), Polymer JR (hydroxyethylcellulose with cationic groups) and plant-based cationic polymers, e.g. guar polymers such as the Jaguar products from Rhodia.

Further suitable polymers are also uncharged polymers, such as polyvinylpyrrolidones, copolymers of N-vinylpyrrolidone and vinyl acetate and/or vinyl)propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives thereof. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, for example based on itaconic acid and aliphatic diamines, as described, for example, in DE-A-43 33 238.

Suitable polymers are also amphoteric or zwitterionic polymers, such as the octylacrylamide/methyl methacrylate/tert-butylaminoethyl methacrylate/hydroxypropyl methacrylate copolymers obtainable under the names Amphomer (National Starch), and zwitterionic polymers, as disclosed, for example, in German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacryloylethyl betaine/methacrylate copolymers, which are available commercially under the Amersette name (AMERCHOL), and copolymers of hydroxyethyl methacrylate, methyl methacrylate, N,N-dimethylaminoethyl methacrylate and acrylic acid (Jordapon (D)).

Suitable polymers are also nonionic, siloxane-containing, water-soluble or water-dispersible polymers, e.g. polyether siloxanes, such as Tegopren® (Goldschmidt) or Besi (Wacker).

There follows a detailed elucidation by way of example of individual particular use forms of actives of the invention. Cooling Skincare and Haircare Products:

In a preferred embodiment, the compositions of the invention are a cooling haircare or skincare product or skin cleanser or hair shampoo.

Preferred skin cleansers or hair shampoos are soaps of liquid to gel consistency, such as transparent soaps, luxury soaps, deodorant soaps, cream soaps, baby soaps, skin protection soaps, abrasive soaps and syndets, pasty soaps, greasy soaps and washing pastes, exfoliating soaps, moisturizing wipes, liquid washing, shower and bath preparations, such as washing lotions, shower baths and gels, foam baths, oil baths and scrub preparations, shaving foams, lotions and creams.

In a further preferred embodiment, the compositions of the invention are a shower gel, a shampoo formulation or a bath preparation. Formulations of this kind comprise at least one active of the invention and typically anionic surfactants as base surfactants and amphoteric and/or nonionic surfactants as cosurfactants. Further suitable actives and/or auxiliaries are generally selected from lipids, perfume oils, dyes, organic acids, preservatives and antioxidants, and thickeners/gel formers, skin conditioners and moisturizers.

In principle, the active ingredient content may vary over a wide range, for example 0.05 ppm to 10% by weight, preferably 0.1 ppm to 10% by weight.

i) Specific Configurations for Compositions for Application to the Skin:

Suitable skin-cosmetic compositions are, for example, face tonics, face masks, deodorants and other cosmetic lotions. Products for use in decorative cosmetics comprise, for example, concealing sticks, stage makeup, mascara and eyeshadow, lipsticks, kohl pencils, eyeliners, blushers, powders and eyebrow pencils.

In addition, the dermatological compositions of the invention may be used in nose strips for pore cleansing, in antiacne compositions, repellents, shaving compositions, aftershave and preshave care compositions, aftersun care compositions, hair removal compositions, hair colorants, intimate care compositions, footcare compositions, and in baby care.

The skincare compositions of the invention are especially W/O or O/W skin creams, day creams and night creams, eye creams, face creams, antiwrinkle creams, sunscreen creams, moisturizing creams, bleaching creams, self-tanning creams, vitamin creams, skin lotions, care lotions and moisturizing lotions.

Skin-cosmetic and dermatological compositions especially comprise at least one active of the invention in a proportion of about 0.05 ppm to 10% by weight, preferably 0.1 ppm to 10% by weight, based on the total weight of the composition.

According to the field of application, the skin-cosmetic compositions of the invention can be applied in a form suitable for skincare, for example in the form of a cream, foam, gel, stick, mousse, milk, spray (pump spray or propellant-containing spray) or lotion.

As well as the actives of the invention and suitable carriers, the skin-cosmetic preparations may also comprise further actives and auxiliaries customary in skin cosmetics, as described above. These preferably include emulsifiers, preservatives, perfume oils, cosmetic actives such as phytantriol, vitamin A, E and C, retinol, bisabolol, panthenol, light stabilizers, bleaches, colorants, tints, tanning agents, collagen, enzymes, protein hydrolyzates, stabilizers, pH regulators, dyes, salts, thickeners, gel formers, bodying agents, silicones, humectants, refatting agents and further customary additives.

Preferred oil and fat components of the skin-cosmetic and dermatological compositions are the aforementioned mineral and synthetic oils, for example paraffins, silicone oils and aliphatic hydrocarbons having more than 8 carbon atoms, animal and vegetable oils, for example sunflower oil, coconut oil, avocado oil, olive oil, lanolin, or waxes, fatty acids, fatty acid esters, for example triglycerides of $C_6$- to $C_{30}$ fatty acids, wax esters, for example jojoba oil, fatty alcohols, vaseline, hydrogenated lanolin and acetylated lanolin, and mixtures thereof.

To establish particular properties, for example improving feel to the touch, spreading characteristics, water resistance and/or the binding of actives and auxiliaries, such as pigments, the skin-cosmetic and dermatological preparations may additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are produced by customary methods known to those skilled in the art.

The dermatological compositions of the invention can be produced by mixing or diluting the actives with a suitable auxiliary (excipient). Excipients may be solid, semisolid or liquid materials which can serve as a vehicle, carrier or medium for the active. Further auxiliaries are added, if desired, in the manner known to the person skilled in the art. In addition, the polymers and dispersions are suitable as auxiliaries in pharmacy, preferably as or in coating(s) or binder(s) for solid drug forms. They can also be used in creams and as tablet coatings and tablet binders.

Preferably, the cosmetic and dermatological compositions are in the form of emulsions, in particular water-in-oil (W/O) or oil-in-water (O/W) emulsions. However, it is also possible to choose other types of formulation, for example gels, oils, oleogels, multiple emulsions, for example in the form of W/O/W or O/W/O emulsions, anhydrous ointments or ointment bases, etc. Emulsifier-free formulations such as hydrodispersions, hydrogels or a Pickering emulsion are also advantageous embodiments.

The emulsions are produced by known methods. As well as at least one active of the invention, the emulsions generally comprise customary constituents such as fatty alcohols, fatty acid esters and especially fatty acid triglycerides, fatty acids, lanolin and derivatives thereof, natural or synthetic oils, or waxes and emulsifiers in the presence of water. The selection of additives specific to the type of emulsion and the production of suitable emulsions is described, for example, in Schrader, Grundlagen und Rezepturen der Kosmetika, Hüthig Buch Verlag, Heidelberg, 2nd edition, 1989, part three, which is hereby explicitly incorporated by reference.

A suitable emulsion in the form of a W/O emulsion, for example for a skin cream etc., generally comprises an aqueous phase emulsified in an oil or fatty phase using a suitable emulsifier system. To provide the aqueous phase, a polyelectrolyte complex can be used.

Preferred fat components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophyllum oil, lanolin and derivatives thereof, castor oil, sesame oil, olive oil, jojoba oil, karité oil, hoplostethus oil; mineral oils whose distillation starting point under atmospheric pressure is at about 250° C. and whose distillation end point is at 410° C., for example vaseline oil; esters of saturated or unsaturated fatty acids, such as alkyl myristates, e.g. i-propyl, butyl or cetyl myristate, hexadecyl stearate, ethyl or isopropyl palmitate, octanoic or decanoic acid triglycerides and cetyl ricinoleate.

The fatty phase may also comprise silicone oils soluble in other oils, such as dimethylpolysiloxane, methylphenylpolysiloxane and the silicone glycol copolymer, fatty acids and fatty alcohols.

As well as the actives of the invention, it is also possible to use waxes, for example carnauba wax, candellila wax, beeswax, microcrystalline wax, ozokerite wax, and calcium, magnesium and aluminum oleates, calcium, magnesium and aluminum myristates, calcium, magnesium and aluminum linoleates and calcium, magnesium and aluminum stearates.

In addition, an inventive emulsion may take the form of an O/V emulsion. Such an emulsion typically comprises an oil phase, emulsifiers which stabilize the oil phase in the water phase, and an aqueous phase which is usually in thickened form. Useful emulsifiers are preferably O/W emulsifiers, such as polyglyceryl esters, sorbitan esters or partly esterified glycerides.

In a further preferred embodiment, the compositions of the invention are a shower gel, a shampoo formulation or a bath preparation.

Formulations of this kind comprise at least one active of the invention and typically anionic surfactants as base surfactants and amphoteric and/or nonionic surfactants as cosurfactants. Further suitable actives and/or auxiliaries are generally selected from lipids, perfume oils, dyes, organic acids, preservatives and antioxidants, and thickeners/gel formers, skin conditioners and moisturizers.

These formulations especially comprise 2% to 50% by weight, such as 5% to 40% by weight, or 8% to 30% by weight, of surfactants, based on the total weight of the formulation.

In the washing, shower and bath preparations, it is possible to use any of the anionic, uncharged, amphoteric or cationic surfactants customarily used in personal cleansers.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isothionates, alkyl phosphates, alkyl ether phosphates, alkyl ether carboxylates, alpha-olefinsulfonates, especially the alkali metal and alkaline earth metal salts, e.g. sodium, potassium, magnesium, calcium, and ammonium and triethanolamine salts. The alkyl ether sulfates, alkyl ether phosphates and alkyl ether carboxylates may have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkyl betaines, alkylamidopropyl betaines, alkyl sulfobetaines, alkyl glycinates, alkyl carboxyglycinates, alkyl amphoacetates or alkyl amphopropionates, alkyl amphodiacetates or alkyl amphodipropionates.

For example, it is possible to use cocodimethylsulfopropyl betaine, lauryl betaine, cocamidopropyl betaine or sodium cocamphopropionate.

Examples of suitable nonionic surfactants are the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. In addition, alkylamine oxides, mono- or dialkyl-alkanolamides, fatty acid esters of polyethylene glycols, ethoxylated fatty acid amides, alkyl polyglycosides or sorbitan ether esters are suitable.

The washing, shower and bath preparations may also comprise customary cationic surfactants, for example quaternary ammonium compounds, for example cetyltrimethylammonium chloride.

In addition, the shower gel/shampoo formulations may comprise thickeners, such as, for example, sodium chloride, PEG 55, propylene glycol oleate, PEG 120 methylglucose dioleate and others, and preservatives, further actives and auxiliaries and water.

ii) Specific Configurations for Compositions for Application to the Hair:

In a further preferred embodiment, the compositions of the invention are a hair treatment composition.

Hair treatment compositions of the invention especially comprise at least one active of the invention in an amount in the range from about 0.05 ppm to 10% by weight, preferably 0.1 ppm to 10% by weight, based on the total weight of the composition.

Preferably, the hair treatment compositions of the invention take the form of a setting foam, hair mousse, hair gel, shampoo, hairspray, hair foam, end fluid, neutralizer for permanent waves, hair colorant and bleach or hot-oil treatments. According to the field of application, the hair-cosmetic preparations can be applied in the form of (aerosol) spray, (aerosol) foam, gel, gel spray, cream, lotion or wax. Hairsprays encompass both aerosol sprays and pump sprays without propellant gas. Hair foams encompass both aerosol foams and pump foams without propellant gas. Hairsprays and hair foams preferably comprise predominantly or exclusively water-soluble or water-dispersible components. If the compounds used in the inventive hairsprays and hair foams are water-dispersible, they can be employed in the form of aqueous microdispersions having particle diameters of typically 1 to 350 nm, preferably 1 to 250 nm. The solids contents of these preparations are typically within a range from about 0.5 ppm to 20% by weight. These microdispersions generally do not require any emulsifiers or surfactants for their stabilization.

In a specific embodiment, the hair-cosmetic formulations of the invention comprise a) 0.0001% to 50% by weight or 0.001% to 10% by weight or 0.005% to 1% by weight of at least one active of the invention, b) 20% to 99.95% by weight of water and/or alcohol, c) 0% to 50% by weight of at least one propellant gas, d) 0% to 5% by weight of at least one emulsifier, e) 0% to 3% by weight of at least one thickener, and up to 25% by weight of further constituents.

"Alcohol" is understood to mean any alcohols customary in cosmetics, e.g. ethanol, isopropanol, n-propanol.

Also included here are all styling and conditioner polymers known in cosmetics which can be used in combination with the actives of the invention if very specific properties are to be established.

Suitable conventional hair cosmetic polymers are, for example, the aforementioned cationic, anionic, uncharged, nonionic and amphoteric polymers, to which reference is made here.

To establish certain properties, the preparations may additionally also comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino-functional silicone compounds such as amodimethicones (CTFA).

The polymers of the invention are particularly suitable as setting agents in hairstyling preparations, especially hairsprays (aerosol sprays and pump sprays without propellant gas) and hair mousses (aerosol mousses and pump mousses without propellant gas).

In a preferred embodiment, spray preparations comprise a) 0.0001% to 50% by weight or 0.001% to 10% by weight or 0.005% to 1% by weight of at least one active of the invention, b) 20% to 99.9% by weight of water and/or alcohol, c) 0% to 70% by weight of at least one propellant, d) 0% to 20% by weight of further constituents.

Propellants are the propellants customarily used for hair sprays or aerosol foams. Preference is given to mixtures of propane/butane, pentane, dimethyl ether, 1,1-difluoroethane (HFC-152 a), carbon dioxide, nitrogen or compressed air.

A formulation for aerosol hair foams which is preferred in accordance with the invention comprises a) 0.0001% to 50% by weight or 0.001% to 10% by weight or 0.005% to 1% by weight of at least one active of the invention, b) 55% to 99.8% by weight of water and/or alcohol, c) 5% to 20% by weight of a propellant, d) 0.1% to 5% by weight of an emulsifier, e) 0% to 10% by weight of further constituents.

Emulsifiers used may be any of the emulsifiers customarily used in hair foams. Suitable emulsifiers may be non-ionic, cationic or anionic, or amphoteric.

Examples of nonionic emulsifiers (INCI nomenclature) are laureths, e.g. Laureth-4; ceteths, e.g. Ceteth-1, polyethylene glycol cetyl ether; cetearaths, e.g. Ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimonium bromide, cocotrimonium methyl sulfate, Quaternium-1 to x (INCI).

Anionic emulsifiers may be selected, for example, from the group of alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates may have between 1 and 10 ethylene oxide or propylene oxide units, preferably 1 to 3 ethylene oxide units, in the molecule.

A formulation suitable in accordance with the invention for styling gels may, for example, be of the following composition: a) 0.0001% to 50% by weight or 0.001% to 10% by weight or 0.005% to 1% by weight of at least one active of the invention, b) 80% to 99.85% by weight of water and/or alcohol, c) 0% to 3% by weight, preferably 0.05% to 2% by weight, of a gel former, d) 0% to 20% by weight of further constituents.

The use of gel formers may be advantageous in order to establish specific rheological or other performance properties of the gels. Gel formers used may be any gel formers customary in cosmetics. These include lightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, Polyquaternium-32 (and) Paraffinum Liquidum (INCI), sodium acrylate copolymers (and) Paraffinum Liquidum (and) PPG-1 Trideceth-6, acrylamidopropyltrimonium chloride/acrylamide copolymers, Steareth-10 allyl ether acrylate copolymers, Polyquaternium-37 (and) Paraffinum Liquidum (and) PPG-1 Trideceth-6, Polyquaternium 37 (and) propylene glycol dicaprate dicaprylate (and) PPG-1 Trideceth-6, Polyquaternium-7, Polyquaternium-44.

Specific shampoo formulations comprise a) 0.0001% to 50% by weight or 0.001% to 10% by weight or 0.005% to 1% by weight of at least one active of the invention, b) 25% to 94.95% by weight of water, c) 5% to 50% by weight of surfactants, c) 0% to 5% by weight of a further conditioner, d) 0% to 10% by weight of further cosmetic constituents.

In the shampoo formulations it is possible to use any of the anionic, uncharged, amphoteric or cationic surfactants customarily used in shampoos.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, especially the alkali metal and alkaline earth metal salts, e.g. sodium, potassium, magnesium, calcium, and ammonium and triethanolamine salts. The alkyl ether sulfates, alkyl ether phosphates and alkyl ether carboxylates may have between 1 and 10 ethylene oxide or propylene oxide units, preferably 1 to 3 ethylene oxide units, in the molecule.

For example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate are suitable.

Suitable amphoteric surfactants are, for example, alkyl betaines, alkylamidopropyl betaines, alkyl sulfobetaines, alkyl glycinates, alkyl carboxyglycinates, alkyl amphoacetates or amphopropionates, alkyl amphodiacetates or amphodipropionates.

For example, it is possible to use cocodimethylsulfopropyl betaine, lauryl betaine, cocamidopropyl betaine or sodium cocamphopropionate.

Examples of suitable nonionic surfactants are the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Additionally suitable are alkylamine oxides, mono- or dialkylalkanolamides, fatty acid esters of polyethylene glycols, alkyl polyglycosides or sorbitan ether esters.

In addition, the shampoo formulations may comprise customary cationic surfactants, for example quaternary ammonium compounds, for example cetyltrimethylammonium chloride.

In the shampoo formulations, particular effects can be achieved using customary conditioners in combination with the actives of the invention.

These include, for example, the abovementioned cationic polymers with the INCI name Polyquaternium, especially copolymers of vinylpyrrolidone/N-vinylimidazolium salts (Luviquat FC, Luviquat HM, Luviquat MS, Luviquat Care), copolymers of N-vinylpyrrolidone/dimethylaminoethyl methacrylate, quaternized with diethyl sulfate (Luviquat D PQ 11), copolymers of N-vinylcaprolactam/N-vinylpyrrolidone/N-vinylimidazolium salts (Luviquat D Hold), cationic cellulose derivatives (Polyquaternium-4 and -10), acrylamide copolymers (Polyquaternium-7). In addition, it is possible to use protein hydrolyzates, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and aminofunctional silicone compounds such as amodimethicones (CTFA). In addition, it is possible to use cationic guar derivatives such as guar hydroxypropyltrimonium chloride (INCI).

Cooling Oral Care Compositions:

Oral care compositions of the invention may be formulated in a manner known per se, for example as toothpaste, tooth gel, or aqueous or aqueous-alcoholic mouthwashes.

Oral care compositions of the invention comprise, based on the weight of the composition, preferably 0.05 ppm to 10% by weight, more preferably 0.1 ppm to 10% by weight, of the total amount of at least one active of the invention.

In addition, the oral care compositions, especially toothpastes, may also comprise abrasives such as silicon oxide hydrate, dicalcium phosphate dihydrate, calcium carbonate, sodium hydrogencarbonate, calcium pyrophosphate and aluminum oxide. For example, it is also possible to use a mixture of thickening precipitated silicon and abrasive precipitated silicon [Handbook of Pharmaceutical Excipients, The Pharmaceutical Society of Great Britain, 1 Lambeth High Street, London SE 1 7JN, England, pages 253-256]. The former is used on account of its thixotropic properties, the latter on account of its better efficacy in the removal of the substances adhering to the tooth surfaces. The use of these products ensures a minor abrasive effect since the materials are amorphous solids of moderate hardness that at the same time are fully and entirely compatible with the fluoride used as mineralizer, since they do not contain any limescale salts that would cause them to be insoluble and reduce their bioavailability.

The formulation of the oral care compositions of the invention, for example toothpaste, may also comprise suitable additives and vehicles in order to improve their properties and facilitate production. These are selected, for example, from binders, thickeners, fragrances, dyes, preservatives, wetting agents or humectants, surfactants, lubricants, opacifiers, remineralizers, surfactants, buffers, alcohols, vitamins, water, additional actives and mixtures thereof.

The binder used may be any agent normally used in the production of this kind of formulations, for example tragacanth gum. The binder may be present in the formulation in an amount of 0.5-1.5% by weight of the total amount.

It is also possible for organic thickeners to be incorporated in the oral care composition, such as sodium carboxymethyl cellulose, cellulose ethers, xanthan gum, carrageenans, sodium alginate and Carbopols. It is also possible to use inorganic thickeners such as silica thickeners, sodium aluminum silicates and clays for provision of the appropriate rheology. The thickener may be present in the formulation in an amount of 0.5-5% by weight of the total amount.

The toothpaste may be aromatized by addition of a suitable customary fragrance, for example a peppermint flavoring. Essential oils including clove oil, cinnamon oil, peppermint oil and spearmint oil, inter alia, are likewise suitable. The fragrance may be present in the formulation in an amount of 0.5-15% by weight of the total amount.

Any dye used customarily in the production of toothpaste may be used as dye, for example Brilliant Blue FCF, C.42090 [KIRSCH PHARMA]. The dye may be present in the formulation in an amount of 0.001-0.005% by weight of the total amount.

The preservative may be any customary agent, for example a derivative of benzoic acid, e.g. p-hydroxymethyl benzoate. The preservative may be present in the formulation in an amount of 0.1-0.3% by weight of the total amount.

Sodium saccharine or cyclamic acid and its derivatives, e.g. sodium cyclamate, may be used as sweetener. The sweetener may be present in the formulation in an amount of 0.08-0.15% by weight of the total amount.

The wetting agent or humectant used to prevent the toothpaste from drying out and hardening is especially selected from glycerol, sorbitol, propylene glycol, xylitol and liquid polyethylene glycols, especially a mixture of sorbitol, glycerol and xylitol, for example in a proportion of 1-60% by weight of the total amount.

The lubricant may be any agent customarily used in the formulation of a toothpaste, e.g. dimethicone (polymer of dimethylpolysiloxane), which is a surfactant that contributes to imparting good rheological properties to the toothpaste of the invention. The lubricant may be present in the formulation in an amount of 0.25% to 0.75% by weight of the total amount.

Any of the agents typically used may be used as opacifier, for example titanium dioxide. The opacifier may be present in the formulation in an amount of 0.05% to 1% by weight of the total amount.

A fluoride source is used as the remineralizing agent, for example sodium fluoride, tin(II) fluoride and sodium monofluorophosphate, since, in this way, 100% of an active fluoride as agent for remineralization of the white lesions caused by the organic acids that are a consequence of bacterial metabolism. The remineralizing agent may be present in the formulation in an amount of 0.2% to 0.4% by weight of the total amount.

Typically, it is additionally possible for customary constituents to be present, such as anionic surfactants, for example sodium lauryl sulfate, sodium N-lauryl sarcosinate, sodium lauryl sulfoacetate and sodium alkyl glyceryl ether sulfonate. The surfactant may be present in the formulation in an amount of 0.05% to 5% by weight of the total amount.

If desired, the toothpaste proposed by the invention may also comprise vitamin selected from the group formed by vitamin A, vitamin B5, vitamin C and vitamin E and mixtures thereof. In the case of use, each vitamin may be present in the formulation in an amount of 0.1% to 5% by weight of the total amount. These vitamins may be used as such, in the form of provitamins or in the form of acceptable pharmaceutical salts. Vitamin A, which is generally used in the form of its palmitate salt, promotes the epithelialization of the oral mucosa and protects the gums. Vitamin B5, more specifically D-panthenol, has an analgesic, healing and anti-inflammatory effect, protects the epithelial mucosa, promotes the epithelialization of wounds and smooths the scars; it is suitable for the treatment of wounds that result from tooth extractions, gingivitis, stomatitis, pain after the insertion of dental prostheses, ulcers, traumatic lesions to the mucosa, chronic and recurrent aphthae. Vitamin C regenerates the epithelium of the oral mucosa, promotes collagen synthesis and the immune system (inflammation mechanism), and increases the ability of the phagocytes to protect against bacteria. Vitamin E, which is normally used in the form of its acetate salt, has an analgesic and anti-inflammatory effect, protects the oral mucosa from fat overoxidation owing to the formation of free radicals and from contaminating substances from the environment (ozone, cigarette smoke etc.) and promotes the healing of wounds. By virtue of the addition of one or more of these vitamins, the invention gives a toothpaste which, as well as the aforementioned properties, also has anti-inflammatory features and analgesic effects that increase the ability of the membranes of the oral mucosa to provide protection and reduce the index of plaque and tartar formation and that of bacterial contamination.

Additional actives are, for example, antimicrobial and plaque-penetrating agents, such as betanaphthol, thymol, chlorothymol and hexylresorcinol; or antibacterial compounds, such as quaternary ammonium compounds; tartar control agents such as tetrasodium pyrophosphate, GANTREZ Polymer® S-70, sodium tripolyphosphate and zinc citrate; peroxide compounds such as hydrogen peroxide and inorganic peroxides.

A buffer may optionally also be used, which is present in concentrations suitable for the maintenance of a pH of about 6-8, for example alkali metal phosphate buffer. The presence of potassium ions additionally exerts an oversensitivity-alleviating effect.

Water or alcohol may be present in a proportion of 1% to 20% by weight of the total amount of the composition.

In combination with the alcohol or in place of the alcohol, it is also possible to use glycol compounds such as glycerol, sorbitol or propylene glycol.

The oral care composition of the invention can easily be produced by mixing suitable amounts of the various constituents in a reactor equipped, for example, with stirrer paddles.

Cooling Patches:

In principle, the active ingredient content may vary over a wide range, for example 0.05 ppm to 10% by weight, preferably 0.1 ppm to 10% by weight.

Patches of the invention may be constructed in any desired manner, for example by the matrix system, the membrane system or the nonwoven system (Drug Dev. Ind. Pharm. 14 (1988), 183-209; Drug Dev. Ind. Pharm. 13 (1987), 589-651; Drugs of Today 23 (1987), 625-646).

The matrix system in its simplest form consists of 3 parts: the flexible support foil, the adhesive matrix containing the active, and a foil for removal. If a nontacky matrix is used, an edge zone of the support foil has to be provided with adhesive for adhesion to the skin.

A membrane system, by contrast, has at least 5 parts: a flexible support foil, a reservoir containing dissolved or suspended active, a membrane for control of active release, an adhesive layer attached to the membrane, and a foil for removal.

In the nonwoven system, the layer comprising the active consists of an absorptive nonwoven or porous polymer impregnated with an active solution or suspension. This layer, firmly bonded to the support foil, is covered by a foil for removal. The edge of the support foil has been provided with adhesive for application to the skin.

In principle, all actives of the invention can be formulated in this way.

The auxiliaries to be used are the customary auxiliaries for the production of patches. As well as the adhesive agent, generally a polymer having a glass transition temperature between −70 and −10° C., especially −55 and −25° C., and a carrier film coated with this adhesive agent and the active, emulsifiers, thickeners and substances intended to influence active release and other auxiliaries are frequently added.

The tacky polymers with the abovementioned low glass transition temperatures are known, for example from U.S. Pat. Nos. 2,973,282 and 3,307,544. The self-adhesive tapes and films should stick to the human skin on mere contact, but the cohesion of the adhesive layer and the adhesion thereof to the carrier film should be greater than the adhesion to the skin, such that they can be removed again largely without residue. These generally comprise copolymers that are based on acrylic and methacrylic acid of alcohols having 2 to 12, especially 4 to 8, carbon atoms and may comprise numerous other comonomers in copolymerized form, for example (meth)acrylic acid, (meth)acrylonitrile, (meth)acrylamide, N-tert-butyl(meth)acrylamide, vinyl esters such as vinyl acetate, propionate or butyrate, other vinyl compounds such as styrene, and butadiene. Particular emphasis should be given to butyl acrylate and 2-ethylhexyl acrylate. The polymers may have been crosslinked by addition of small amounts of comonomers having 2 or more copolymerizable double bonds, i.e., for example, of diacrylates such as butanediol diacrylate, or divinyl compounds such as divinylbenzene, or by addition of other crosslinkers, e.g. melamine-formaldehyde resins. Tacky polymers used may also be polyisobutylenes and polyvinyl ethers of different molecular weight.

The particle size of the dispersions should be between 50 and 500 nm, especially between 50 and 200 nm. The particle size and degree of crosslinking can be adjusted in a known manner depending on the polymerization conditions and the comonomers. Smaller particle sizes and an elevated level of crosslinking can result in an increase in active release.

Matrix patches can be produced in a customary manner by dissolving or finely dispersing the active in a suitable polymer solution and then drawing down this active-containing self-adhesive composition by means of roll or squeegee application methods to give a film. In some cases, it is appropriate to dissolve or ultrafinely disperse the active in an organic solvent, e.g. ethanol or acetone, prior to the addition to the polymer solution. This can achieve better distribution of the active in the polymer.

The patches may also be produced according to German patent application P 38 07 283.1 by incorporating the active in fine pulverulent form (particle size below 200 µm, especially below 50 µm) into the aqueous latex dispersion, or dispersing or dissolving it in an aqueous emulsifier solution and mixing this mixture into the aqueous latex dispersion at a temperature of 10 to 80° C., especially 30 to 70° C. In addition, the salt of an active in aqueous solution may also be mixed with the polymer dispersion at a pH at which the active is predominantly in the water-soluble ionized form. By adjusting the pH, the active is then converted to the uncharged water-insoluble form and simultaneously emulsified into the dispersion.

Appropriately, the active is initially charged, the emulsifier and water are added, and then they are mixed with the polymer dispersion. The active-containing dispersion thus obtained is optionally provided with further auxiliaries and, as mentioned, drawn down in a manner known per se on a support foil to form a film and dried. The drying temperature here may be between room temperature and 100° C., with an optimum between the aims of rapid drying and avoidance of blister formation in the film and thermal stress on the active generally at 35 to 45° C.

This process has the great advantage of the avoidance of organic solvents. However, all other customary production methods for matrix patches are also useful in principle.

The resulting films have thicknesses of 10 to 800 µm, preferably 50 to 300 µm. The films can be produced continuously or batchwise. The application method can be repeated multiple times until the film has attained the desired thickness. The tacky polymer layer comprises the active in a concentration in the range from 1% to 40% by weight, especially 5% to 25% by weight. The same concentration also applies to the reservoir liquid in the membrane system and to the active solution or dispersion with which the nonwoven in the case of the nonwoven system or the porous polymer is impregnated.

Emulsifiers used both for the actives and the polymers are the surfactants customary for the purpose, such as the sodium salt of relatively long-chain fatty acids and of the sulfuric monoester of an (optionally ethoxylated) fatty alcohol as examples of anionic surfactants, and polyethoxylated alkylphenols and relatively long-chain fatty alcohols (e.g. hexadecan-1-ol) and glycerol fatty acid partial esters as examples of nonionic surfactants and coemulsifiers.

The desired viscosity of the mass ready for drawdown may be adjusted, for example, with polyacrylic acids or cellulose derivatives.

Examples of additional crosslinking agents that may be used to improve the cohesion and hence the bonding properties of the films include melamine-formaldehyde resins.

Swelling agents such as polyvinylpyrrolidone, cellulose derivatives or polyacrylates are effective for the purpose of improving active release, since the film can absorb an increased amount of water and hence diffusion resistance falls. The release of the actives can also be improved by the addition of hydrophilic plasticizers such as glycerol, propane-1,2-diol, the polyethylene glycols and lipophilic plasticizers such as triacetin, dibutyl phthalate or isopropyl myristate.

Matrix patches typically give 1st order active release. The use of fillers that adsorb the active, such as aerosil, microcrystalline cellulose or lactose, results in nearly 0th order release.

The support foil onto which the active-containing self-adhesive composition is dried is appropriately virtually impervious both to the active and to water vapor. It may consist, for example, of an aluminum-plastic composite foil, a metallized plastic foil, a polymer film provided with a barrier layer of polyvinylidene chloride, for example, on the active side, or of a simple polymer film, e.g. polyester film.

The patches of the invention constructed by the membrane system are likewise produced in a customary manner (e.g. EP 0 186 071 A2, U.S. Pat. No. 4,262,003).

The patches constructed by the nonwoven system are produced by impregnating nonwovens or porous polymers secured to the support foil with a solution or dispersion of the active in a hydrophilic or lipophilic solvent or solvent mixture. Subsequently, the impervious foil for removal is attached.

Cooling Foods;

Cooling foods of the invention (at ambient temperature) may be in solid, liquid, semisolid, pasty, creamy or foamed form. As well as conventional food constituents, they comprise at least an effective (i.e. cooling-effective) amount of at least one active of the invention.

Typical constituents here are fats, carbohydrates, proteins, dietary fibers, water, alcohol and the like.

The protein content may, for example, be 0% to 50% by weight, based on the total weight of the food;
the fat content may, for example, be 0% to 50% by weight, based on the total weight of the food;
the carbohydrate content may, for example, be 0% to 90% by weight, based on the total weight of the food;
the dietary fiber content may, for example, be 0% to 90% by weight, based on the total weight of the food;
the water content may, for example, be 0% to 95% by weight, based on the total weight of the food;
the alcohol content may, for example, be 0% to 15% by weight, based on the total weight of the food;
the proportion of actives of the invention may, for example, be in the range from 0.05 ppm to 10% by weight, preferably 0.1 ppm to 10% by weight, based on the total weight of the food.

Examples of carbohydrates are, for example, mono- and disaccharides, glucose, galactose, mannose, lactose, maltose and sucrose; fructose and mannose; polysaccharides, for example starches, maltodextrins; flour.

The term "dietary fiber" relates to soluble, insoluble, fermentable, non-fermentable or any combination of such dietary fibers. The dietary fiber may comprise, for example, soya fibers, pectin, particular resistant starches, oligofructose, inulins, oat fibers, pea fibers, guar gum, acacia gum, modified cellulose.

The fat constituent may be any lipid or fat of known suitability for use in foods. Typical fats include milk fat, safflower oil, canola oil, egg yolk lipid, olive oil, cottonseed oil, coconut oil, palm oil, palm kernel oil, soybean oil, sunflower oil, fish oil and fractions of all aforementioned oils that derive therefrom, such as palmolein, mid-chain triglycerides (MCTs), and fatty acid esters, where the fatty acids are, for example, arachidonic acid, linoleic acid, palmitic acid, stearic acid, docosahexaenoic acid, eicosapentaenoic acid, linolenic acid, oleic acid, lauric acid, capric acid, caprylic acid, caproic acid. Forms of various oils having a high oleic acid content are also considered suitable for the present use, such as high-oleic sunflower oil and high-oleic safflower oil.

The protein may be any protein and/or amino acid mixture of known suitability for use in foods. Typical proteins are animal proteins, plant proteins such as soya protein, milk protein such as skimmed milk protein, whey protein and casein, and amino acids (or salts thereof) such as isoleucine, phenylalanine, leucine, lysine, methionine, threonine, tryptophan, arginine, glutamine, taurine, valine. Preferred protein sources are whey protein, sodium caseinate or calcium caseinate, optionally with added amino acids. For some applications, a preferred protein source is hydrolyzed protein (protein hydrolyzate), optionally with added amino acids.

The protein hydrolyzate may be any suitable protein hydrolyzate which is used in a food, such as soya protein hydrolyzate, casein hydrolyzate, whey protein hydrolyzate, other animal and vegetable protein hydrolyzates, and mixtures thereof. The protein hydrolyzate in the composition of the invention is preferably a soya protein, whey protein or casein protein hydrolyzate comprising short peptides and amino acids and optionally with added additional amino acids. In a preferred embodiment, the protein hydrolyzate suitable in accordance with the invention comprises a high proportion of free amino acids (for example more than 40%) and low molecular weight peptide fragments.

The hydrolyzed protein in the composition of the invention has also preferably been admixed with various free amino acids in order to provide a nutritionally balanced amino acid content. Examples of such free amino acids include L-tryptophan, L-methionine, L-cystine, L-tyrosine and L-arginine.

The foods of the invention optionally also comprise vitamins and minerals. The person skilled in the art is familiar with minimum requirements that have been established for particular vitamins and minerals that are needed for normal physiological function. The person skilled in the art also knows that additional amounts of vitamin and mineral constituents appropriate to the foods must be added in order to compensate for certain losses in the processing and storage of such compositions. The composition of the invention optionally contains significant amounts of vitamins and minerals for nutrition purposes.

Examples of minerals, vitamins and other nutrients that may be present in the composition of the invention include vitamin A, vitamin $B_6$, vitamin $B_{12}$, vitamin E, vitamin K, vitamin C, vitamin D, inositol, taurine, folic acid, thiamine, riboflavin, niacin, biotin, pantothenic acid, choline, calcium, phosphorus, iodine, iron, magnesium, copper, zinc, manganese, chloride, potassium, sodium, beta-carotene, nucleotides, selenium, chromium, molybdenum and L-carnitine. Minerals are typically added in salt form.

The composition of the invention optionally also typically comprises emulsifiers and/or stabilizers such as lecithin (for example from egg or soya), modified lecithin (for example enzymatic or acetylated), carrageenan, xanthan gum, mono- and diglycerides, guar gum, carboxymethyl cellulose, stearoyl lactylates, succinylated monoglycerides, sucrose esters of fatty acids, diacetyltartaric esters of monoglycerides, polyglycerol esters of fatty acids or any mixtures thereof.

The composition of the invention optionally comprises one or more natural or synthetic flavor carriers to improve palatability. It is possible to use any flavor carrier used in the sector, such as strawberry, cherry, chocolate, orange, coconut, vanilla; spices such as nutmeg and cinnamon; or citric acid. In some cases in which natural flavor carriers such as pieces of coconut are used, the constituent contributes to the overall nutritional profile of the composition, meaning that it contributes to the quality and quantity of the fat, protein and/or carbohydrate constituent.

The composition of the invention optionally also comprises various other constituents that contribute to the nutritional profile of the composition and/or can impart desirable flavor properties, such as enhancement of flavor or mouthfeel. Such constituents include peanuts, raisins, cheese powder, vinegar, salt, sodium bicarbonate. In the case of bars, the composition is typically provided with a chocolate or aromatized coating (e.g. chocolate, vanilla, strawberry etc.).

The composition of the invention optionally also comprises natural or synthetic dyes in order to improve the visual impression.

The compositions of the invention may be in multiple physical manifestations, for example in the form of liquid enteral foods or drinks for adults or children, in a semisolid form such as blancmange, cream, mousse, or a solid form, such as a nutrition bar or biscuit.

The composition of the invention may be produced by known standard methods in food technology, for example by methods analogous to those described in the following publications: U.S. Pat. Nos. 4,670,268; 4,497,800; 4,900,566; 5,104,677; 5,389,395; and 5,223,285; Chocolate, Cocoa and Confectionery: Science and Technology, 3rd edition, Bernard W. Minifie, Van Nostrand Reinhold, New York, 1989, p. 502-506; which are fully incorporated by reference.

In the case of nutrition bars and biscuits, the aim is typically to bake the composition after the so physical shaping.

The composition of the invention can if desired be sterilized by known methods, for example by heat treatment such as autoclaving or sterilizing or irradiating, or produced and packaged by sterile methods.

The composition of the invention can be packed in any kind of container or packing known to be suitable for storage of foods, such as paper, glass, coated cardboard, plastic or coated metal cans.

The composition of the invention may be nutritionally balanced. The term "nutritionally balanced" is understood to mean that the composition comprises appropriate nutrients to maintain healthy human life over extended periods of time.

Textile Products Modified with Actives of the Invention:

The modification of textiles with actives of the invention is of interest from various points of view.

For instance, the modification of textiles with cooling compounds find use especially where items of clothing come into direct contact with the skin, such that the active, via transdermal transfer, can display its effects, for example locally or systemically. There have recently been reports of textiles modified with "wellness additives", i.e. substances that promote wellness (R. Breier "Megatrend Wellness—Innovative Ideen für die Textilausrüstung [Wellness, The Megatrend—Innovative Ideas for Textile Modification]", 31. Aachener Textiltage November 2004).

Insecticidal modification is again of interest with regard to material protection, for example modification of the textile to counter moth damage, etc., but especially also to ward off parasitic insects such as mosquitoes.

A fundamental problem in the modification of textiles with actives is the binding of the active to the textile carrier, which on the one hand must ensure permanence of the modification and on the other hand must be chosen such that the active does not lose its effect. Various approaches are proposed in the prior art for this purpose.

For example, cyclodextrins have been suggested for binding of actives to textiles (see, for example, DE-A-19810951 and EP-A-0 392 608). Cyclodextrins are cyclic oligosaccharides that are formed by enzymatic degradation of starch. The most common cyclodextrins are α-, β- and γ-cyclodextrins, consisting respectively of six, seven and eight α-1,4-bonded glucose units. A characteristic property of the cyclodextrin molecules is their ring structure with largely unchanging dimensions. The internal diameter of the rings is about 570 μm for α-cyclodextrin, about 780 μm for β-cyclodextrin and about 950 μm for γ-cyclodextrin. Owing to their structure, cyclodextrins are capable of including guest molecules, especially hydrophobic guest molecules, in varying amounts up to saturation.

EP-A-1710345 describes the modification of textiles with fragrances and other organic actives of low molecular weight that are bound to the textile by means of an amylose-containing substance with an amylose content of at least 30%.

As a result of the amylose contents of the amylose-containing substance, the active is bound to the textile and released in a controlled manner, such that the effect is maintained over a long period of time. It is assumed that the active, in a similar manner to cyclodextrins, is reversibly bound within the cavities formed by the helical conformation of the amylose in the manner of an inclusion compound, which firstly achieves fixing of the active on the surface of the textile carrier and secondly enables controlled release.

For the inventive modification of textiles, as well as amylose, all substances are suitable in principle, especially amylose-containing starches, i.e. native starches, modified starches and starch derivatives, having an amylose content of at least 30% by weight and especially at least 40% by weight. The starch may be native, for example corn starch, wheat starch, potato starch, sorghum starch, rice starch or arrowroot starch, or may have been obtained or chemically modified by partial digestion of native starch. Also suitable is pure amylose as such, for example amylose obtained by enzymatic means, for example amylose obtained from sucrose. Also suitable are mixtures of amylose and starch, provided that the total amylose content is at least 30% by weight, based on the total weight of the mixture. It will be apparent that all figures in % by weight relating to amylose or amylose-containing substances here and hereinafter, in the case of mixtures of amylose and starch, are always based on the total weight of amylose+starch, unless explicitly stated otherwise.

Particularly suitable in accordance with the invention are amylose-containing substances, especially amylose and amylose-containing starches and amylose/starch mixtures, wherein the amylose content is at least 40% by weight and especially at least 45% by weight, based on the total weight of the substance. In general, the amylose content will not exceed 90% by weight and especially 80% by weight. Such substances are known and commercially available. For example, amylose-containing starches are sold by Cerestar under the Amylogel® brand name and National Starch under the HYLON® V and VII brand names.

To achieve the binding of the active(s) and the textile, the textile may be modified with the amylose-containing substance generally in an amount of at least 0.5% by weight, preferably at least 1% by weight and especially at least 2% by weight, based in each case on the weight of the textile. In general, the amylose-containing substance will be used in an amount of not more than 25% by weight, frequently not more than 20% by weight and especially not more than 15% by weight, based on the weight of the textile, in order not to adversely affect the tactile properties of the textile.

First of all, the textile material is modified with the amylose-containing substance as such and then the textile thus modified is treated with a suitable preparation of the active. In this way, the amylose-containing substance present on the textile material is laden with the active.

Alternatively, it is possible to use the amylose-containing substance together with an active to modify the textile. It is possible here to employ the active and the amylose-containing substance either as a mixture of separate components or in the already prefabricated form of the amylose/active complex.

In general, the active will be used in an amount sufficient for the desired effect. The upper limit is determined by the maximum absorption capacity of the amylose units of the amylose-containing substance used and will generally not exceed 20% by weight and frequently 10% by weight, based on the amylose content of the substance. If desired, the active is generally used in an amount of 0.00001% to 15% by weight, 0.0001% to 10% by weight, 0.001% to 5% by weight, 0.005% to 1% by weight or 0.1% to 10% by weight or 0.5% to 5% by weight, based on the amylose content of the amylose-containing substance.

Textile modification can also be accomplished using combinations of actives of the invention with other actives known per se that are suitable for textile modification.

Suitable further actives are in principle all organic compounds and mixtures of organic compounds that are known as actives and induce a physiological effect in lifeforms such as humans and animals, including microorganisms. These include those actives that are known to form inclusion compounds with cyclodextrins. Particularly suitable actives are those that have hydrocarbyl groups and especially aliphatic, cycloaliphatic and/or aromatic structures. The molecular weight of the actives is typically below 1000 daltons and frequently in the range from 100 to 600 daltons. Also suitable are inorganic compounds such as hydrogen peroxide which, as is well-known, can be bound within cyclodextrins (in this regard see F. Vögtle, Supramolecular Chemistry, 2nd edition, B. G. Teubner, Stuttgart 1992, cyclodextrins and literature cited therein).

The further actives especially include pharmaceutical actives and actives that promote the wellness of lifeforms, especially of humans, and which are commonly also referred to as "wellness additives". Unlike pharmaceutical actives, the wellness additives need not necessarily have a therapeutic effect. Instead, the wellness-promoting effect may be based on a multitude of factors such as care effects, inducing effects, cosmetic effects or other effects. Equally suitable are organic actives that act against parasitic organisms. These include, for example, actives that act against fungi and/or microorganisms, e.g. fungicides and bactericides, or that act against animal pests such as slugs, worms, mites, insects and/or rodents, e.g. nematicides, molluscicides, insecticides, acaricides, rodenticides and repellent actives, and also actives against weed grasses, i.e. herbicides, or fragrances.

Preferred pharmaceutical actives are those that are known to be absorbable through the skin. These include, for example, ibuprofen, flurbiprofen, acetylsalicylic acid, acetamidophen, apomorphin, butylated hydroxytoluene, chamazulene, guaiazulene, chlorthalidone, cholecalciferol, dicumarol, digoxin, diphenylhydantoin, furosemide, hydroflumethiazide, indomethacin, iproniazid phosphate, nitroglycerine, nicotine, nicotinamide, ouabain, oxprenolol, papaverine alkaloids such as papaverine, laudanosine, ethaverine and narcotine, and also berberine, and additionally retinol, trans-retinoic acid, pretinol, spironolactone, sulpiride, theophylline, theobromine, corticosteroids and derivatives such as testosterone, 17-methyltestosterone, cortisone, corticosterone, dexamethasone, triamcinolone, methylprednisolone, fludrocortisone, fluocortolone, prednisone, prednisolone, progesterone, inter alia, estrogens and gestagens such as estradiol, estriol, ethinylestradiol 3-methyl ether, norethisterone and ethisterone, and also phenethylamine and derivatives such as tyramine, adrenaline, noradrenaline and dopamine.

Examples of actives suitable in accordance with the invention that have an effect against parasitic organisms are the nematicides, bactericides, fungicides, insecticides, insect repellents, acaricides and molluscicides cited at www.reith-pfister.de/w.list.html and at www.hclrss.demon.co.uk/class_pesticides.html.

Examples of bactericidal and fungicidal substances include:

antibiotics, e.g. cycloheximide, griseofulvin, kasugamycin, natamycin, polyoxin, streptomycin, penicillin or gentamycin;

organic compounds and complexes of biocidal metals, e.g. complexes of silver, copper, tin and/or zinc, such as bis (tributyltin) oxide, copper, zinc and tin naphthenates, oxine-copper such as Cu-8, tris-N-(cyclohexyldiazeniumdioxy) aluminum, N-(cyclohexyldiazeniumdioxy)tributyltin, bis-N-(cyclohexyldiazeniumdioxy)copper;

quaternary ammonium salts, e.g. benzyl-$C_8$- to $C_{18}$-alkyldimethylammonium halides, especially chlorides (benzalkonium chlorides);

aliphatic nitrogen fungicides and bactericides such as cymoxanil, dodin, dodicin, guazidine, iminoctadin, dodemorph, fenpropimorph, fenpropidin, tridemorph;

substances having peroxide groups, such as hydrogen peroxide, and organic peroxides such as dibenzoyl peroxide;

organic chlorine compounds, for example chlorhexidine;

triazole fungicides such as azaconazole, cyproconazole, diclobutrazole, difenoconazole, diniconazole, epoxiconazole, fenbuconazole, fluquinconazole, flusilazole, flutriafol, hexaconazole, metconazole, propiconazole, tetraconazole, tebuconazole and triticonazole;

strobilurins such as dimoxystrobin, fluoxastrobin, kresoxim methyl, metominostrobin, orysastrobin, picoxystrobin, pyraclostrobin and trifloxystrobin;

sulfonamides such as tolylfluanide and diclofluanide;

iodine compounds such as diiodomethyl p-tolyl sulfone, napcocide, 3-iodo-2-propynyl alcohol, 4-chlorophenyl 3-iodopropargyl formal, 3-bromo-2,3-diiodo-3-propenyl ethylcarbonate, 2,3,3-triiodoallyl alcohol, 3-iodo-2-propynyl n-hexylcarbamate, 3-bromo-2,3-diiodo-2-propenyl alcohol, 3-iodo-2-propynyl phenylcarbamate, 3-iodo-2-propynyl n-butylcarbamate, O-1-(6-iodo-3-oxohex-5-ynyl) phenylcarbamate, O-1-(6-iodo-3-oxohex-5-ynyl) butylcarbamate; isothiazolinones such as N-methylisothiazolin-3-one, 5-chloro-N-methylisothiazolin-3-one, 4,5-dichloro-N-octyl-isothiazolin-3-one, 1,2-benzisothiazol-3(2H)one, 4,5-trimethylisothiazol-3-one and N-octylisothiazolin-3-one.

Examples of Insecticides and Acaricides are organophosphates such as acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, triazophos, trichlorfon;

especially pyrethroids such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, α-cypermethrin, β-cypermethrin, λ-cypermethrin, zeta-cypermethrin, cyphenothrin, deltamethrin, dimefluthrin, dimethrin, empenthrin, fenfluthrin, fenprithrin, fenpropathrin, fenvalerate, esfenvalerate, flucythrinate, fluvinate, tau-fluvinate, furethrin, permethrin, biopermethrin, trans-permethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute and silafulfen;

pyrrole and pyrazole insecticides such as acetoprole, ethiprole, fipronil, tebufenpyrad, tolfenpyrad, chlorfenapyr and vaniliprole.

Examples of repellent actives are especially anthraquinone, acridine bases, copper naphthenate, butopyronoxyl, dibutyl phthalate, dimethyl phthalate, dimethyl carbate, ethohexadiol, hexamide, methoquin-butyl, N-methylneodecanamide, camphor, bergamot oil, pyrethrum, clove oil, geranium oil, thyme oil and especially diethyl-m-toluamide and 2-(2-hydroxyethyl)-1-methylpropyl 1-piperidinecarboxylate (picaridin).

Examples of wellness additives are especially the substances and substance mixtures listed below, for example fats, preferably of plant origin, e.g. lecithins, vegetable oils such as jojoba oil, tea tree oil, clove oil, evening primrose oil, almond oil, coconut oil, avocado oil, soybean oil and the like, fatty acids, e.g. ω-6-fatty acids, linolenic acid, linoleic acid, waxes of animal or plant origin, such as beeswax, candelilla wax, shea butter, shorea butter, mango kernel butter, japan wax and the like, vitamins, especially fat-soluble vitamins, e.g. tocopherols, vitamin E, vitamin A and the like, corticosteroids such as cortisone, corticosterone, dexamethasone, triamcinolone, methylprednisolone, fludrocortisone, fluocortolone, prednisone, prednisolone, progesterone, amino acids, e.g. arginine, methionine, plant extracts such as algae extract, horse chestnut extract, mango extract and the like.

For improvement of the wash permanence of the modification of the invention, it has been found to be useful when the amylose-containing substance is fixed on the textile with a binder. Useful binders include firstly film-forming, water-insoluble polymers and secondly reactive substances of low molecular weight that polymerize when heated. In general, the binder will be used in such an amount that the weight ratio of amylose-containing substance to water-insoluble polymer is in the range from 1:1 to 100:1, preferably in the range from 1.5:1 to 50:1 and especially in the range from 2:1 to 20:1.

In general, the film-forming polymers are used in the form of an aqueous dispersion of finely divided polymer particles. Particle size is of minor importance for the success of the invention. However, it is generally below 5 μm (weight-average) and is generally 50 nm to 2 μm.

The film-forming polymer may especially have a glass transition temperature $T_G$ in the range from −40 to 100° C., preferably −30 to +60° C., especially −20 to +40° C. If the polymeric binder comprises multiple polymer components, at least the main constituent should have a glass transition temperature within this range. The glass transition temperature of the main constituent is especially in the range from −30° C. to +60° C. and more preferably in the range from −20° C. to +40° C. All polymeric constituents preferably have a glass transition temperature within these ranges. The glass transition temperatures reported relate to the midpoint temperature determined by means of DSC according to ASTM-D 3418-82. In the case of crosslinkable binders, the glass transition temperature relates to the uncrosslinked state.

Examples of suitable film-forming polymers are based on the following polymer classes:
(1) polyurethane resins;
(2) acrylate resins (straight acrylates: copolymers of alkyl acrylates and alkyl methacrylates);
(3) styrene acrylates (copolymers of styrene and alkyl acrylates);
(4) styrene/butadiene copolymers;
(5) polyvinyl esters, especially polyvinyl acetates and copolymers of vinyl acetate with vinyl propionate;
(6) vinyl ester-olefin copolymers, e.g. vinyl acetate/ethylene copolymers;
(7) vinyl ester-acrylate copolymers, e.g. vinyl acetate/alkyl acrylate copolymers and vinyl acetate/alkyl acrylate/ethylene terpolymers.

Such polymers are known and are commercially available, for example polymers of classes (2) to (7) in the form of aqueous dispersions under the following names: ACRONAL, STYROFAN, BUTOFAN (BASF AG), MOWILITH, MOWIPLUS, APPRETAN (Clariant), VINNAPAS, VINNOL (WACKER). Aqueous polyurethane dispersions (1) suitable for the process of the invention are especially those that are used for the coating of textiles (see, for example, J. Hemmrich, Int. Text. Bull. 39, 1993, No. 2, p. 53-56; "Wässrige Polyurethan-Beschichtungssysteme" [Aqueous Polyurethane Coating Systems] Chemiefasern/Textilind. 39 91 (1989) T149, T150; W. Schröer, Textilveredelung [Textile finishing] 22, 1987, p. 459-467). Aqueous polyurethane dispersions are commercially available, for example under the following trade names: Alberdingk® from Alberdingk, Impranil® from BAYER AG, Permutex® from Stahl, Waalwijk, the Netherlands, from BASF SE, or they can be prepared by known methods as described, for example, in "Herstellverfahren für Polyurethane" [Production methods for polyurethanes] in Houben-Weyl, "Methoden der organischen Chemie" [Methods of Organic Chemistry], volume E 20/Makromolekulare Stoffe [Macromolecular Substances], p. 1587, D. Dietrich et al., Angew. Chem. 82 (1970), p. 53 ff., Angew. Makrom. Chem. 76, 1972, 85 ff. and Angew. Makrom. Chem. 98, 1981, 133-165, Progress in Organic Coatings, 9, 1981, p. 281-240, or Römpp Chemielexikon [Römpp's Chemical Lexicon], 9th edition, volume 5, p. 3575.

The film-forming polymers may be self-crosslinking, meaning that the polymers have functional groups (crosslinkable groups) which, when the composition is dried, optionally with heating, react with one another, with the functional groups of the amylose or with a low molecular weight crosslinker to form bonds.

Examples of crosslinkable functional groups include aliphatically bonded OH groups, NH—CH$_2$—OH groups, carboxylate groups, anhydride groups, capped isocyanate groups and amino groups. A polymer still having free OH groups as reactive groups will frequently be used. In general, the proportion of the reactive functional groups is 0.1 to 3 mol/kg of polymer. The crosslinking can be brought about within the polymer by reaction of functional groups having complementary reactivity. Preferably, the crosslinking of the polymer is brought about by adding a crosslinker having reactive groups that are complementary with regard to their reactivity toward the functional groups of the crosslinker. Suitable pairs of functional groups having complementary reactivity are known to the person skilled in the art. Examples of such pairs are OH/COOH, OH/NCO, NH$_2$/COOH, NH$_2$/NCO and M$^{2+}$/COOH, where M$^{2+}$ is a divalent metal ion such as Zn$^{2+}$, Ca$^{2+}$, or Mg$^{2+}$. Examples of suitable crosslinkers are the di- or polyols mentioned below for the polyurethanes; primary or secondary diamines, preferably primary diamines, e.g. alkylenediamines such as hexamethylenediamine, diethylenetriamine, triethylenetetramine, tetraethylenepentamine, N,N-bis[(aminopropyl)amino]ethane, 3,6-dioxaoctanediamine, 3,7-dioxanonanediamine, 3,6,9-trioxaundecanediamine or Jeffamines, (4,4'-diaminodicyclohexyl)methane, (4,4'-diamino-3,3-dimethyldicyclohexyl)methane; amino alcohols such as ethanolamine, hydroxypropylamine; ethoxylated di- and oligoamines; dihydrazides of aliphatic or aromatic dicarboxylic acids such as adipic dihydrazide; dialdehydes such as glyoxal; partly or fully O-methylated melamines, and compounds or oligomers that have an average of two or more, preferably three or more, isocyanate groups or reversibly blocked, e.g. hydrogensulfite-blocked, isocyanate groups. In this case, the ratio of crosslinker to polymeric binder is such that the molar ratio of the reactive groups in the polymeric binder (total amount of the reactive groups in the polymers) to the reactive groups in the crosslinker is generally in the range from 1:10 to 10:1 and preferably in the range from 3:1 to 1:3. Typically, the weight ratio of polymeric binder (calculated as solids) to crosslinker is in the range from 100:1 to 1:1 and especially in the range from 50:1 to 5:1.

As an alternative to the fixing of the amylose-containing substance with water-insoluble polymers, the amylose or the amylose-containing substance can also be fixed on the textile material with reactive compounds having at least one group reactive toward the OH groups of the amylose and at least one further functional group reactive toward the functional groups on the fibers of the textile material, for example OH groups, NH$_2$ groups or COOH groups. The reactive compounds include the abovementioned crosslinkers and the substances proposed in DE-A 40 35 378 for the fixing of cyclodextrins, for example N-hydroxymethyl and N-alkoxymethyl derivatives of urea or urea-like compounds such as dimethylolurea (bis(hydroxymethyl)urea), di(methoxymethyl)urea, dimethylolalkanedioldiurethanes such as N,N-dimethylolethyleneurea (N,N-bis(hydroxymethyl)imidazolin-2-one), N,N-dimethyloldihydroxyethyleneurea (N,N-bis(hydroxymethyl)-4,5-dihydroxyimidazolin-2-one), dimethylolpropyleneurea and the like. Such materials are in the form of aqueous formulations for the commercial modification of textiles, for example under the Fixapret® and Fixapret®-eco trade names from BASF SE. The reactive materials that can be utilized for fixing of the amylose-containing substance on the textile material especially also include compounds having 2, 3, 4 or more (optionally reversibly blocked) isocyanate groups, specifically the polyisocyanate prepolymers that have been reversibly blocked with bisulfite or CH-acidic compounds or oximenes, e.g. butanone oxime, and are based on polyether- and polyesterurethanes, which are described in DE 2837851, DE 19919816 and prior European patent application 03015121. Such products are also commercially available, for example under the PROTOLAN®367 and PROTOLAN®357 trade names from Rotta GmbH, Mannheim.

The amylose-containing substance can also be fixed using the procedure known for the fixing of cyclodextrins in an analogous manner, in which the cyclodextrin or, in the present case, the amylose-containing substance is provided with reactive anchors, for example by reacting it in a manner known per se with dicarboxylic acids or dicarboxylic anhydrides such as maleic acid, fumaric acid, maleic anhydride, succinic acid, succinic anhydride or adipic acid, with isocyanates, e.g. toluene diisocyanate, isophorone diisocyanate, tetramethylene diisocyanate or hexamethylene diisocyanate, or with aminocarboxylic acids, in such a way that just one of the functionalities present in these compounds reacts with the OH groups of the amylose-containing substance and the other is conserved for binding to the reactive groups of the fiber material. Reactive anchors can also be generated on the amylose-containing substance by reaction with 1,3,5-trichlorotriazine, 2,3-dichloroquinoxaline-5,6-carbonyl chloride and with chlorodifluoropyrimidine.

In addition, fixing of the amylose can also be accomplished using alkoxysilanes, such as diethoxydimethylsilane, dimethoxydimethylsilane, triethoxyphenylsilane, tetraethoxysilane, and dimeric, trimeric and higher condensation products of these compounds.

In this way, it is possible in principle to modify all textile materials, i.e. unfinished material or finished material. Textile materials here and hereinafter include woven fabrics, loop-drawn knitted fabrics, loop-formed knitted fabrics and nonwoven fabrics. The textile materials may have been constructed from natural fiber yarns, synthetic fiber yarns and/or mixed yarns. Useful fiber materials in principle include all fiber materials used customarily for the production of textiles. These include cotton, wool, hemp fibers, sisal fibers, flax, ramie, polyacrylonitrile fibers, polyester fibers, polyamide fibers, viscose fibers, silk, acetate fibers, triacetate fibers, aramid fibers and the like, and mixtures of these fiber materials.

The modification or treatment of the textile materials with the amylose-containing substance can be effected in a manner known per se, for example by means of the methods described in DE-A 4035378 for the modification of textiles with cyclodextrins.

Mention should be made by way of example of methods in which the amylose-containing substance, optionally as a complex with the active, has already been spun into the fiber, the filament and/or the yarn from which the fabric has been produced.

Frequently, however, the textile material, before or after finishing, will be treated with the amylose-containing substance or a complex of amylose-containing substance and the active. In general, for this purpose, the textile will be treated with an aqueous liquor comprising the amylose-containing substance and optionally the active in a sufficient amount. According to the manner of application and the desired amount in which the amylose-containing substance is to be applied, the concentration of amylose-containing substance in the liquor is in the range from 1% to 40% by weight, particularly in the range from 2% to 20% by weight and especially in the range from 4% to 15% by weight.

The manner of treatment is of minor importance and can be effected, for example, in the form of a minimal application, for example by spray application, in the form of a normal application in a pad-mangle or as a high-moisture application. The textile material here is soaked with the aqueous liquor. Optionally, excess liquor can be removed thereafter, for example by squeezing it out to a liquor pickup of about 30% to 120%.

Another way of treating the textile with amylose-containing substance or complex of amylose-containing substance and active is that of making up a liquor with water in which the desired amount of amylose-containing substance and optionally active is present, e.g. 0.5% to 20% by weight (based on the mass of the textiles to be modified). The textile material is soaked with the treatment liquor in modification aggregates suitable for the purpose (e.g. winch beck; roller beck; paddle; etc.) over a certain time period, e.g. 10-60 min, and then is squeezed and/or spun out as specified above. The liquor ratio here is generally in the range from 1:2 to 1:50 and especially in the range from 1:3 to 1:20.

Such methods are known to the person skilled in the art, for example from H. K. Rouette, Lexikon der Textilveredlung [Lexicon of Textile Finishing], Laumann-Verlag, Dülmen 1995, p. 669 ff.

In general, the treatment with the liquor is followed by a drying operation. The temperatures here are generally in the range from 100 to 200° C. and preferably in the range from 120 to 180° C. The drying can be performed in the apparatuses customary for the purpose, in the case of finished material for example by tumble-drying at the above-specified temperatures. In the case of unfinished material, the application will generally be followed by guiding the textile material through one or more tenter frames.

If the amylose-containing substance is used together with a film-forming polymer, the drying leads to fixing of the amylose-containing substance on the textile fibers. In general, the drying temperature in that case will not be less than 100° C. and is preferably in the range from 120 to 200° C. and especially in the range from 140 to 180° C. In general, the drying is effected over a period 1 to 10 min, especially 1 to 2 min, although longer drying times are likewise suitable.

For the treatment with an aqueous liquor, it has been found to be advantageous when the aqueous liquor, as well as the amylose-containing substance and optionally the active, comprises at least one surface-active substance (or interface-active substance) suitable for dispersion of the amylose-containing substance and the active in the aqueous liquor. The surface-active substance is preferably an oligomeric or polymeric dispersant. The term "oligomeric or polymeric dispersant", by contrast with low molecular weight surface-active substances, embraces those dispersants having a number-average molecular weight of generally at least 2000 daltons, for example 2000 to about 100 000 daltons, and especially in the range from about 3000 to 70 000 daltons.

In general, the aqueous liquor comprises the polymeric or oligomeric dispersant in an amount of 0.5% to 20% by weight, preferably 1% to 18% by weight and especially 5% to 15% by weight, based on the amylose-containing substance.

Suitable oligomeric or polymeric dispersants are water-soluble and include both uncharged and amphoteric water-soluble polymers and cationic and anionic polymers, preference being given to the latter.

Examples of uncharged polymeric dispersants are polyethylene oxide, ethylene oxide/propylene oxide copolymers, preferably block copolymers, polyvinylpyrrolidone, and copolymers of vinyl acetate with vinylpyrrolidone.

It is a feature of the preferred anionic oligomeric or polymeric dispersants that they have carboxyl groups and/or sulfonic acid groups and are typically used as salts, for example as alkali metal salts or ammonium salts.

Preferred anionic dispersants are, for example, carboxylated derivatives of cellulose such as carboxymethyl cellulose, homopolymers of ethylenically unsaturated $C_3$- to $C_8$-mono- and $C_4$- to $C_8$-dicarboxylic acids, for example of acrylic acid, of methacrylic acid, of maleic acid, of itaconic acid, copolymers of at least two different ethylenically unsaturated $C_3$- to $C_8$-mono- and $C_4$- to $C_8$-dicarboxylic acids as specified above, and copolymers of at least one of the aforementioned ethylenically unsaturated $C_3$- to $C_8$-mono- or $C_4$- to $C_8$-dicarboxylic acids with at least one uncharged comonomer. Examples of uncharged comonomers are N-vinyllactams such as N-vinylpyrrolidone, vinyl esters of aliphatic $C_2$- to $C_{16}$-carboxylic acids, such as vinyl acetate, vinyl)propionate, amides of the aforementioned ethylenically unsaturated carboxylic acids, such as acrylamide, methacrylamide and the like, hydroxy-$C_1$- to $C_4$-alkyl (meth)acrylates such as hydroxyethyl acrylate and methacrylate, esters of ethylenically unsaturated $C_3$- to $C_8$-mono- or $C_4$- to $C_8$-dicarboxylic acids with polyethers, for example esters of acrylic acid or methacrylic acid with polyethylene oxides or ethylene oxide/propylene oxide block copolymers, vinylaromatics such as styrene and $C_2$- to $C_{16}$-olefins such as ethylene, propene, 1-hexene, 1-octene, 1-decene, 1-dodecene and the like. Preference is further given to homopolymers of ethylenically unsaturated sulfonic acids such as styrenesulfonic acid and acrylamidopropanesulfonic acid and copolymers thereof with the aforementioned comonomers. In the copolymers, the proportion of the ethylenically unsaturated acid will generally be at least 20% by weight and not exceed a value of 90% by weight and especially 80% by weight, based in each case on the total weight of all monomers that constitute the polymer.

Copolymers of at least one of the abovementioned acids and at least one comonomer are known for this purpose and are commercially available, for example the copolymers of acrylic acid and maleic acid as Sokalan brands from BASF SE.

Anionic dispersants that are likewise preferred are phenolsulfonic acid-formaldehyde condensates and naphthalenesulfonic acid-formaldehyde condensates (e.g. the Tamol and Setamol brands from BASF) and lignosulfonates.

Usable dispersants are also anionic, nonionic, cationic, ampholytic and zwitterionic surfactants of low molecular weight. Suitable surfactants are, for example, the alkali metal, ammonium or amine salts of $C_8$- to $C_{18}$-alkylsulfates, such as sodium lauryl sulfate; $C_8$- to $C_{18}$-alkylsulfonates, such as dodecylsulfonate; $C_8$- to $C_{18}$-alkyl ether sulfates; and $C_8$- to $C_{18}$-alkyl ethoxylates; polyoxyethylenesorbitan esters; $C_8$- to $C_{18}$-alkylglycinates; $C_8$- to $C_{18}$-alkyldimethylamine oxides; betaines etc. Preference is given to the alkylsulfates and alkylsulfonates.

If the amylose-containing substance is not used together with a film-forming, water-insoluble polymer, the textile can be treated with the polymer in a separate step. More particularly, treatment is effected together with the amylose-containing substance. Accordingly, a particular embodiment relates to a method in which the aqueous liquor additionally comprises a dispersed, film-forming, water-insoluble polymer of the type described above. The amount of film-forming polymer is chosen here such that the weight ratio of amylose-containing substance to water-insoluble polymer is in the range from 1:1 to 100:1, preferably in the range from 1.5:1 to 50:1 and especially in the range from 2:1 to 20:1.

The textile can be modified with the active in a separate operation or in an operation together with the modification with the amylose-containing substance.

If the textile is modified with the active in a separate operation, the textile will appropriately likewise be treated with an aqueous liquor of the active. For this purpose, the active, which is typically water-insoluble, will generally be emulsified or dispersed in water, optionally with use of suitable surface-active substances. Suitable surface-active substances are especially the aforementioned low molecular weight surfactants, and among these preferably the nonionic surfactants, especially polyoxyethylenesorbitan esters, esters of mono- or oligosaccharides with $C_6$ to $C_{18}$ fatty acids and more preferably $C_8$- to $C_{18}$-alkyl ethoxylates, especially those with an ethoxylation level in the range from 6 to 50. In general, the aqueous liquor comprises the active in an amount of 0.1% to 10% by weight and especially in an amount of 0.2% to 5% by weight. The amount of surface-active substance is generally in the range from 0.5% to 50% by weight and especially in the range from 3% to 30% by weight, based on the active. The active can be applied from aqueous liquor by the methods customary for the purpose, for example by means of a pad-mangle.

Alternatively, it is possible to perform the modification with active and amylose-containing substance in one operation. The procedure here may in principle be as described for the modification with the amylose-containing substance, wherein the aqueous liquor of the amylose-containing substance now additionally comprises the at least one active. The active may be added to the liquor separately or in the form of an inclusion compound, i.e. in the form of a host-guest complex with the amylose-containing substance.

The present invention may be utilized for modification of any textiles, including woven fabrics, knitted fabrics, nonwoven fabrics and the like. The type of textile material is guided primarily by the desired end use.

The textiles to be modified may be ready-finished products such as clothing, including underwear and outerwear, for example shirts, trousers, jackets, outdoor, trekking and military apparel, roofs, tents, meshes, for example insect protection meshes, and curtains, hand and bath towels, bed linen and the like.

In the same way, the modification may be effected on the raw material in bale or roll form.

The textiles that have been modified with actives against parasitic organisms such as insects and acarids are suitable not only for the protection of man but also particularly in animal protection for protection against ticks, mites, fleas and the like.

The textile materials may have been constructed from natural fiber yarns, synthetic fiber yarns and/or mixed yarns, where the fabrics typically have a basis weight in the range from 10 to 500 g/m², preferably 20 to 250 g/m². Useful fiber materials in principle include all fiber materials used customarily for the production of textiles. These include cotton, wool, hemp fibers, sisal fibers, flax, ramie, polyacrylonitrile fibers, polyester fibers, polyamide fibers, viscose fibers, silk, acetate fibers, triacetate fibers, aramid fibers and the like, and mixtures of these fiber materials. Also suitable are glass fibers and mixtures of the aforementioned fiber materials with glass fibers, e.g. glass fiber/Kevlar mixtures.

With an above-described amylose-based active modification, the actives remain in the textiles modified therewith even after several washes. In addition, the textiles thus modified feature a pleasant hand, which is advantageous especially for the wear comfort of clothing manufactured from these textiles.

Cooling Tobacco Products:

In principle, the active ingredient content may vary over a wide range, for example 0.05 ppm to 10% by weight, preferably 0.1 ppm to 10% by weight.

The actives of the invention may also be used advantageously for production of tobacco products. Examples of such tobacco products include cigars, cigarettes, pipe tobacco, chewing tobacco and snuff.

The production of tobacco products supplemented with cooling additions is known per se and is described, for example, in U.S. Pat. Nos. 3,111,127, 5,752,529 and US 2005/0000529, which are explicitly incorporated by reference.

Cooling Packing Materials:

The actives of the invention are also advantageously suitable for production of packing materials.

They are likewise produced in a manner known per se. The actives may be incorporated here into the packing material, in free or, for example, encapsulated form, or applied to the packing material, in free or encapsulated form.

For instance, correspondingly modified plastic packing materials are producible in accordance with the details in the literature relating to the production of polymer films (e.g. Ullmann, 6th edn, 2003. Vol. 36, p. 567). The production of papers coated in a suitable manner is likewise known and is described, for example, in Ullmann, Vol. 25, p. 106 if, 6th edn, 2003.

Further aspects of the present invention will be apparent from the examples that follow, and the appended claims.

EXAMPLES

The examples serve to illustrate the invention without restricting it thereby. Unless stated otherwise, all figures are based on weight.

Active Production:

The actives of structure type 1 used in accordance with the invention are either compounds known per se or can be prepared by the person skilled in the art in the field of organic synthesis on the basis of known synthesis methods.

Cloning of Human TRPM8:

The starting point for the cloning of the human TRPM8 receptor is an LnCaP cDNA bank. This is, for example, commercially available (for example from BioChain, Hayward, USA) or can be produced from the androgen-sensitive human prostate adenocarcinoma cell line (e.g. ATCC, CRL1740 or ECACC, 89110211) using standard kits.

The encoding TRPM8 sequence (see, for example, http://www.ncbi.nlm.nih.gov/entrez/viewer.fcgi?db=nuccore&id=09689694) can be PCR-amplified and cloned using standard methods. The human TRPM8 gene thus isolated was used for production of the plasmid plnd_M8.

Alternatively, the TRPM8 gene can also be produced synthetically.

Generation of the HEK293 Test Cells:

The test cell system produced, with human TRPM8 DNA, was a stably transfected HEK293 cell line. Preference is given here to HEK293 which, via the plasmid introduced, offers the option of induction of TRPM8 expression by means of tetracycline.

Methods of production of suitable test cell systems are known to the person skilled in the art. For instance, the production of the cells used can be inferred from the details in Behrendt H. J. et al., Br. J. Pharmacol. 141, 2004, 737-745 or the thesis by Behrendt "Vergleichende funktionale Untersuchungen des Hitze-Capsaicin-Rezeptors (TRPV1) und des Kälte-Menthol-Rezeptors (TRPM8) in rekombinanten und nativen Zellssystemen" [Comparative Functional Studies of the Heat Capsaicin Receptor (TRPV1) and the Cold Menthol Receptor (TRPM8) in Recombinant and Native Cell Systems], available for example at http://www-brs.ub.ruhr-uni-bochum.de/netahtml/HSS/Diss/BehrendtHansJoerg/diss.pdf. The disclosure of these publications is explicitly incorporated by reference.

Assay for TRPM8 Modulators:

A test comparable with the test already described in the literature by Behrendt H. J. et al., Br. J. Pharmacol. 141, 2004, 737-745, is conducted. The agonism or antagonism of the receptor can be quantified by means of a $Ca^{2+}$-sensitive dye (e.g. FURA, Fluo-4 etc.). Agonists on their own result in an increase in the $Ca^{2+}$ signal; antagonists in the presence of menthol, for example, result in a reduction in the $Ca^{2+}$ signal (in each case detected by means of the Fluo-4 dye which is caused to have different fluorescence properties by $Ca^{2+}$).

First of all, in a manner known per se, a fresh culture of transformed HEK cells is produced in cell culture bottles. The HEK293-TRPM8 test cells are detached from the cell culture bottles by means of trypsin and 40 000 cells/well are sown with 100 µl of medium in 96-hole plates (Greiner #655948 poly-D-lysine-coated). For induction of the TRPM8 receptor, tetracycline is added to the growth medium (DMEM/HG, 10% FCS tetracycline-free, 4 mM L-glutamine, 15 µg/mL blasticidin, 100 µg/mL hygromycin B, 1 µg/mL tetracycline). The next day, the cells are laden with Fluo-4AM dye and the test is conducted. The procedure for this purpose is as follows:

Adding to each well 100 µl/well $C_8$-4 Kit staining solution (RB 141, Molecular Devices) for each 100 µl of medium (DMEM/HG, 10% FCS tetracycline-free, 4 mM L-glutamine, 15 µg/mL blasticidin, 100 µg/mL hygromycin B, 1 µg/mL tetracycline)

Incubation in an incubator, 30 minutes/37° C./5% $CO_2$, 30 minutes/RT

Preparation of the test substances (different concentrations in 200 µl of HBSS buffer), and positive controls (different concentrations of menthol, icilin and ionomycin in 200 µl of HBSS buffer) and negative controls (200 µl of HBSS buffer only)

Addition of the test substances in amounts of 50 µl/well and measurement of the change in fluorescence (for example in the FLIPR assay instrument, Molecular Devices, or NovoStar, BMG) at excitation 485 nm, emission 520 nm, and evaluation of the intensity of action of the different substances/concentrations and determination of the EC50 values.

The test substances are used in the assay in triplicates in concentrations of 0.1-200 µM. Normally, the compounds are kept in DMSO solutions and diluted down for the assay to a maximum DMSO concentration of 2%.

In-house evaluations in the case of performance of the assay described showed, surprisingly, that the compounds to be used in accordance with the invention (as described herein) are particularly suitable as agonists of TRPM8.

The EC50 values ascertained for modulators of the invention selected by way of example are shown in the table below.

| Structure | Name | Activity In vitro assay (EC50) |
|---|---|---|
| | (E)-3-(1,3-benzodioxol-5-yl)-N-phenyl-N-tetrahydrofuran-3-yl-prop-2-enamide | 25 μM |
| | (E)-3-(4-methoxyphenyl)-N-phenyl-N-tetrahydrofuran-3-yl-prop-2-enamide | 12.5 μm |
| 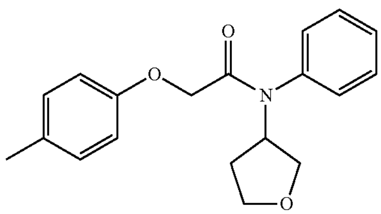 [SMILES: Cc1ccc(OCC(=O)N(c2ccccc2)C2CCOC2)cc1] | 2-(4-methylphenoxy)-N-phenyl-N-tetrahydrofuran-3-yl-acetamide | 25 μm |
| | 2-(4-methylphenoxy)-N-phenyl-N-tetrahydrothiophen-3-yl-acetamide | 12.5 μm |
| 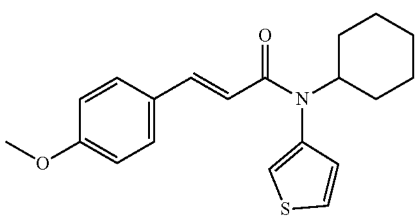 [SMILES: COc1ccc(/C=C/C(=O)N(c2ccsc2)C2CCCCC2)cc1] | (E)-N-cyclohexyl-3-(4-methoxyphenyl)-N-(3-thienyl)prop-2-enamide | 25 μm |
| 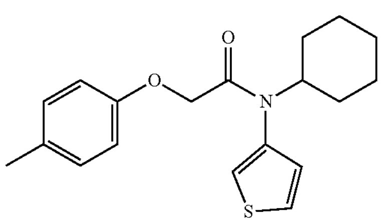 [SMILES: Cc1ccc(OCC(=O)N(c2ccsc2)C2CCCCC2)cc1] | N-cyclohexyl-2-(4-methylphenoxy)-N-(3-thienyl)acetamide | 30 μm |
| 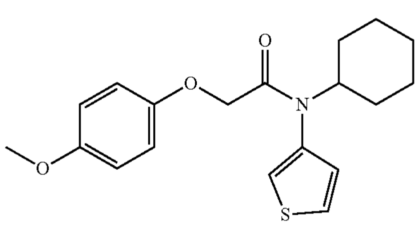 [SMILES: COc1ccc(OCC(=O)N(c2ccsc2)C2CCCCC2)cc1] | N-cyclohexyl-2-(4-methoxyphenoxy)-N-(3-thienyl)acetamide | 50 μm |

-continued

| Structure | Name | Activity In vitro assay (EC50) |
|---|---|---|
| 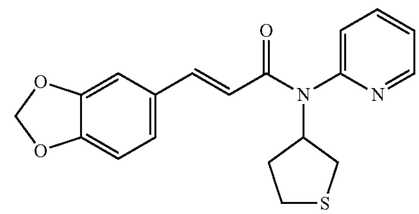 [SMILES: O=C(/C=C/c1ccc2c(c1)OCO2)N(c1ccccn1)C1CCSC1] | (E)-3-(1,3-benzodioxol-5-yl)-N-(2-pyridyl)-N-tetrahydrothiophen-3-yl-prop-2-enamide | 6 μm |
| 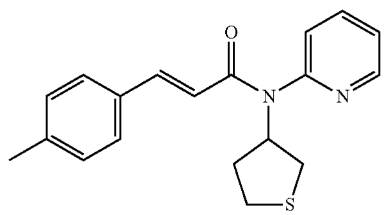 | (E)-3-(p-tolyl)-N-(2-pyridyl)-N-tetrahydrothiophen-3-yl-prop-2-enamide | 25 μm |
| 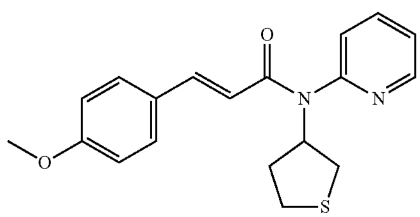 [SMILES: COc1ccc(/C=C/C(=O)N(c2ccccn2)C2CCSC2)cc1] | (E)-3-(4-methoxyphenyl)-N-(2-pyridyl)-N-tetrahydrothiophen-3-yl-prop-2-enamide | 25 μm |
| 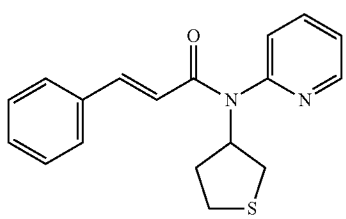 [SMILES: O=C(/C=C/c1ccccc1)N(c1ccccn1)C1CCSC1] | (E)-3-phenyl-N-(2-pyridyl)-N-tetrahydrothiophen-3-yl-prop-2-enamide | 30 μm |
| 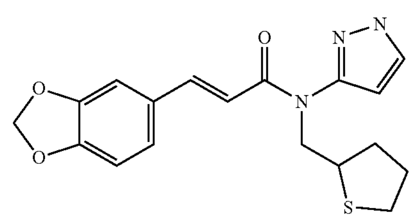 [SMILES: O=C(/C=C/c1ccc2c(c1)OCO2)N(CC1CCCS1)c1cc[nH]n1] | (E)-3-(1,3-benzodioxol-5-yl)-N-(1H-pyrazol-3-yl)-N-(tetrahydrothiophen-2-ylmethyl)prop-2-enamide | 5 μm |
| 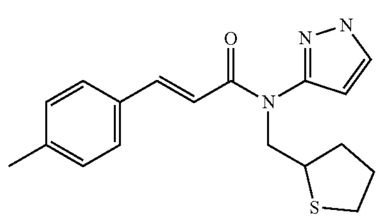 [SMILES: Cc1ccc(/C=C/C(=O)N(CC2CCCS2)c2cc[nH]n2)cc1] | (E)-3-(p-tolyl)-N-(1H-pyrazol-3-yl)-N-(tetrahydrothiophen-2-ylmethyl)prop-2-enamide | 50 μm |
| 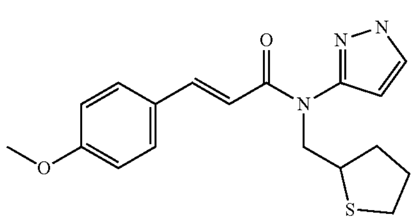 [SMILES: COc1ccc(/C=C/C(=O)N(CC2CCCS2)c2cc[nH]n2)cc1] | (E)-3-(4-methoxyphenyl)-N-(1H-pyrazol-3-yl)-N-(tetrahydrothiophen-2-ylmethyl)prop-2-enamide | 50 μm |

-continued

| Structure | Name | Activity In vitro assay (EC50) |
|---|---|---|
| 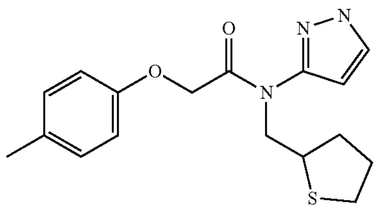 [SMILES: Cc1ccc(OCC(=O)N(CC2CCCS2)c2cc[nH]n2)cc1] | 2-(4-methylphenoxy)-N-(1H-pyrazol-3-yl)-N-(tetra-hydrothiophen-2-yl-methyl)acetamide | 50 μm |
| 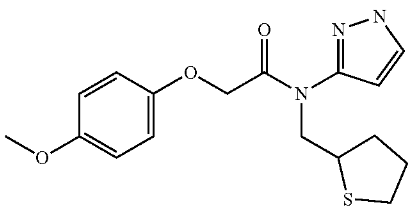 [SMILES: COc1ccc(OCC(=O)N(CC2CCCS2)c2cc[nH]n2)cc1] | 2-(4-methoxyphenoxy)-N-(1H-pyrazol-3-yl)-N-(tetra-hydrothiophen-2-yl-methyl)acetamide | 50 μm |
| 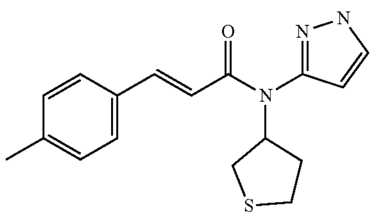 [SMILES: Cc1ccc(/C=C/C(=O)N(c2cc[nH]n2)C2CCSC2)cc1] | (E)-3-(p-tolyl)-N-(1H-pyrazol-3-yl)-N-tetrahydrothio-phen-3-yl-prop-2-enamide | 50 μm |
| 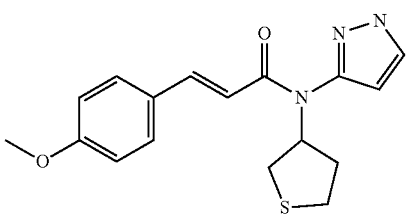 [SMILES: COc1ccc(/C=C/C(=O)N(c2cc[nH]n2)C2CCSC2)cc1] | (E)-3-(4-methoxyphenyl)-N-(1H-pyrazol-3-yl)-N-tetrahydrothiophen-3-yl-prop-2-enamide | 50 μm |
| 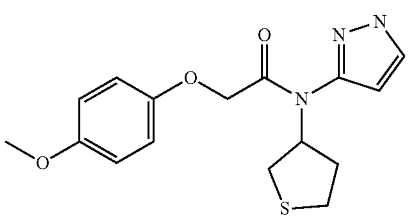 [SMILES: COc1ccc(OCC(=O)N(c2cc[nH]n2)C2CCSC2)cc1] | 2-(4-methoxyphenoxy)-N-(1H-pyrazol-3-yl)-N-tetra-hydrothiophen-3-yl-acetamide | 10 μm |
| 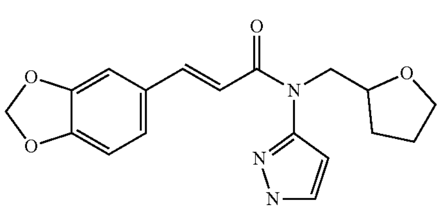 [SMILES: O=C(/C=C/c1ccc2c(c1)OCO2)N(CC1CCCO1)c1cc[nH]n1] | (E)-3-(1,3-benzodioxol-5-yl)-N-(1H-pyrazol-3-yl)-N-(tetrahydrofuran-2-yl-methyl)prop-2-enamide | 15 μm |
| 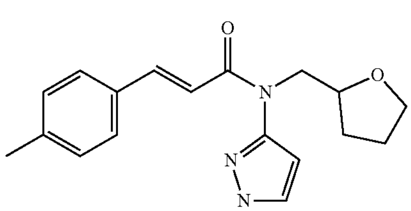 [SMILES: Cc1ccc(/C=C/C(=O)N(CC2CCCO2)c2cc[nH]n2)cc1] | (E)-3-(p-tolyl)-N-(1H-pyrazol-3-yl)-N-(tetrahydrofuran-2-ylmethyl)prop-2-enamide | 10 μm |

-continued

| Structure | Name | Activity In vitro assay (EC50) |
|---|---|---|
| 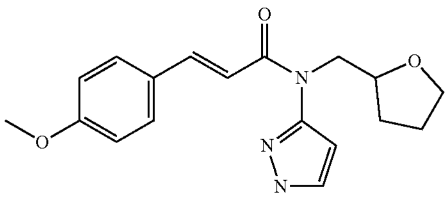 [SMILES: COc1ccc(/C=C/C(=O)N(CC2CCCO2)c2cc[nH]n2)cc1] | (E)-3-(4-methoxyphenyl)-N-(1H-pyrazol-3-yl)-N-(tetrahydrofuran-2-yl-methyl)prop-2-enamide | 25 μm |
| 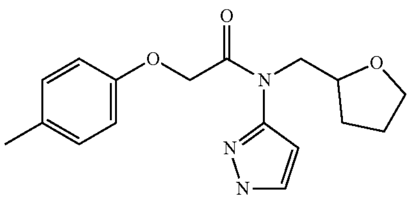 [SMILES: Cc1ccc(OCC(=O)N(CC2CCCO2)c2cc[nH]n2)cc1] | 2-(4-methylphenoxy)-N-(1H-pyrazol-3-yl)-N-(tetra-hydrofuran-2-ylmethyl)acetamide | 10 μm |
| 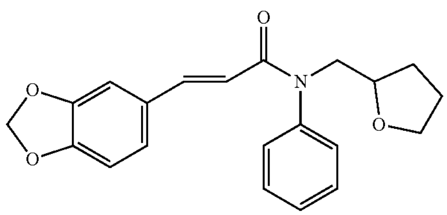 [SMILES: O=C(/C=C/c1ccc2c(c1)OCO2)N(CC1CCCO1)c1ccccc1] | (E)-3-(1,3-benzodioxol-5-yl)-N-phenyl-N-(tetra-hydrofuran-2-ylmethyl)prop-2-enamide | 5 μm |
| 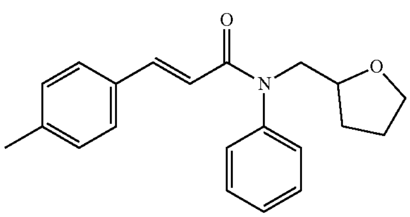 [SMILES: Cc1ccc(/C=C/C(=O)N(CC2CCCO2)c2ccccc2)cc1] | (E)-N-phenyl-3-(p-tolyl)-N-(tetrahydrofuran-2-yl-methyl)prop-2-enamide | 5 μm |
| 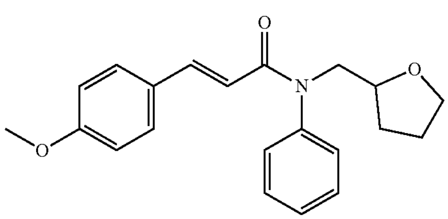 [SMILES: COc1ccc(/C=C/C(=O)N(CC2CCCO2)c2ccccc2)cc1] | (E)-3-(4-methoxyphenyl)-N-phenyl-N-(tetrahydro-furan-2-ylmethyl)prop-2-enamide | 25 μm |
| 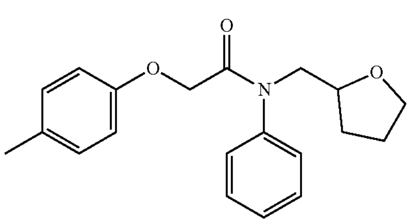 [SMILES: Cc1ccc(OCC(=O)N(CC2CCCO2)c2ccccc2)cc1] | 2-(4-methylphenoxy)-N-phenyl-N-(tetrahydro-furan-2-ylmethyl)acetamide | 50 μm |
| 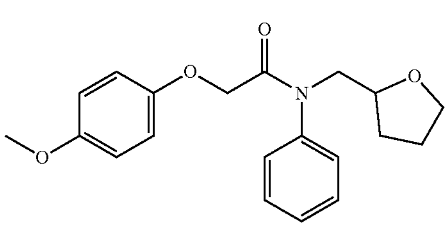 [SMILES: COc1ccc(OCC(=O)N(CC2CCCO2)c2ccccc2)cc1] | 2-(4-methoxyphenoxy)-N-phenyl-N-(tetrahydro-furan-2-ylmethyl)acetamide | 50 μm |

-continued

| Structure | Name | Activity In vitro assay (EC50) |
|---|---|---|
| 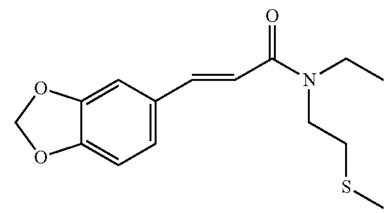 [SMILES: CCN(CCSC)C(=O)/C=C/c1ccc2c(c1)OCO2] | (E)-3-(1,3-benzodioxol-5-yl)-N-ethyl-N-(2-methyl-sulfanylethyl)prop-2-enamide | 15 μm |
| 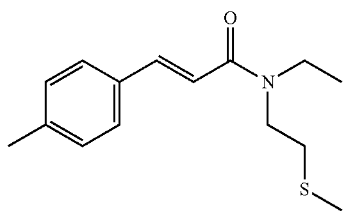 | (E)-N-ethyl-N-(2-methyl-sulfanylethyl)-3-(p-tolyl)prop-2-enamide | 10 μm |
| 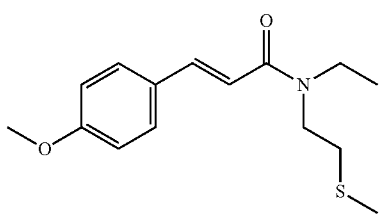 | (E)-N-ethyl-3-(4-methoxy-phenyl)-N-(2-methyl-sulfanylethyl)prop-2-enamide | 50 μm |
| 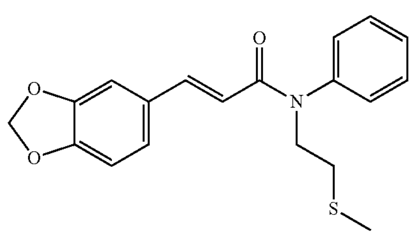 [SMILES: CSCCN(C(=O)/C=C/c1ccc2c(c1)OCO2)c1ccccc1] | (E)-3-(1,3-benzodioxol-5-yl)-N-(2-methyl-sulfanylethyl)-N-phenyl-prop-2-enamide | 50 μm |
| 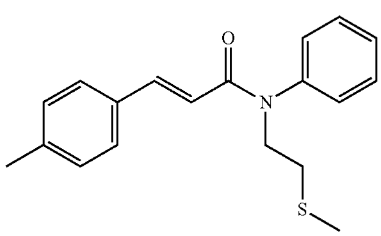 [SMILES: CSCCN(C(=O)/C=C/c1ccc(C)cc1)c1ccccc1] | (E)-N-(2-methyl-sulfanylethyl)-N-phenyl-3-(p-tolyl)prop-2-enamide | 50 μm |
| 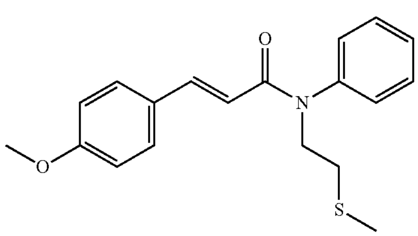 [SMILES: COc1ccc(/C=C/C(=O)N(CCSC)c2ccccc2)cc1] | (E)-3-(4-methoxyphenyl)-N-(2-methylsulfanylethyl)-N-phenyl-prop-2-enamide | 25 μm |

| Structure | Name | Activity In vitro assay (EC50) |
|---|---|---|
| 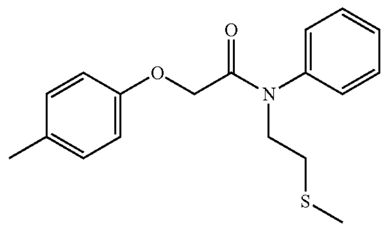 [SMILES: CSCCN(C(=O)COc1ccc(C)cc1)c1ccccc1] | 2-(4-methylphenoxy)-N-(2-methylsulfanylethyl)-N-phenyl-acetamide | 25 μm |
| 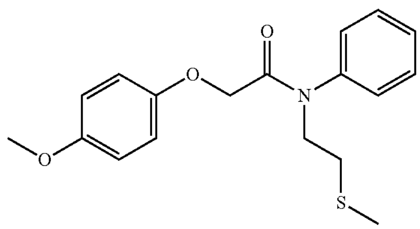 [SMILES: COc1ccc(OCC(=O)N(CCSC)c2ccccc2)cc1] | 2-(4-methoxyphenoxy)-N-(2-methylsulfanylethyl)-N-phenyl-acetamide | 30 μm |
| | (E)-3-(1,3-benzodioxol-5-yl)-N-ethyl-N-(3-methylsulfanylpropyl)prop-2-enamide | 30 μm |

Synthesis Examples

1) Preparation of N-ethyl-2-methylsulfanylethanamine

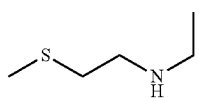

1,1-Dimethoxy-2-(methylthio)ethane (21.5 mL, 161.07 mmol, 1.0 eq) is dissolved in HCl solution (0.5 M, 323 mL, 1.0 eq) and stirred at 50° C. for 1 h. The reaction mixture is cooled down to RT and extracted with $CH_2Cl_2$ (500 mL). The combined organic phases are dried over $Na_2SO_4$. The aldehyde solution is diluted with THF (500 mL), cooled to 0° C. and then admixed with ethylamine (70% solution in water, 15.57 mL, 241.61 mmol, 1.5 eq), acetic acid (9.1 mL, 161.07 mmol, 1.0 eq) and $Na_2SO_4$ (250 g). After 16 h, the reaction mixture is filtered through $Na_2SO_4$ and admixed with sodium triacetoxyborohydride (37.6 g, 177.17 mmol, 1.1 eq). The reaction mixture is stirred at RT for 16 h. The solids are filtered through kieselguhr and the solution is concentrated under reduced pressure. The crude product is distilled under reduced pressure (7 mbar, 60° C.). The compound is used without further analyses.

Yield: 23%.

2) Preparation of N-ethyl 3-methylsulfanylpropan-1-amine

Methional (25.0 g, 240.0 mmol, 1.0 eq) is dissolved in THF (1000 mL), cooled to 0° C. and then admixed with ethylamine (70% solution in water, 23.2 mL, 360.0 mmol, 1.5 eq), acetic acid (13.6 mL, 240.0 mmol, 1.0 eq) and $Na_2SO_4$ (250 g). After 16 h, the reaction mixture is filtered through $Na_2SO_4$ and admixed with sodium triacetoxyborohydride (55.95 g, 264.0 mmol, 1.1 eq). The reaction mixture is stirred at RT for 16 h. The solids are filtered through kieselguhr and the solution is concentrated under reduced pressure. The crude product is distilled under reduced pressure (7 mbar, 60° C.). The compound is used without further analyses.

Yield: 31%.

3) Preparation of N-pyridine-, N-phenyl- and N-1H-pyrazoleamines 1,1-Dimethoxy-2-(methylthio)ethane (1.0 eq) is dissolved in HCl solution (0.5 M, 1.0 eq) and stirred at 50° C. for 1 h. The reaction mixture is cooled down to RT and extracted with $CH_2Cl_2$ (3 mL/mmol in total). The combined organic phases are dried over $Na_2SO_4$. The aldehyde solution is cooled to 0° C. and then admixed with amine (1.0 eq), sodium triacetoxyborohydride (1.5 eq) and acetic acid (1.0 eq). The reaction mixture is stirred at RT for 16 h. The reaction is ended by the addition of NaHCO₃ solution. The aqueous phase is extracted three times with CH₂Cl₂, and the combined organic phases are dried over Na₂SO₄ and concentrated under reduced pressure. The crude product is purified by flash chromatography (hexane:EtOAc=19:1).

N-(2-methylsulfanylethyl)pyridine-2-amine

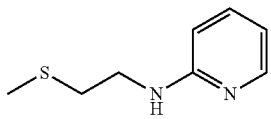

84% yield
The compound is used without further analyses.

N-(2-methylsulfanylethyl)aniline

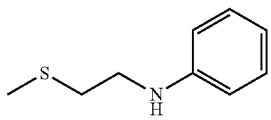

Yield: 85%
The compound is used without further analyses.

N-(2-methylsulfanylethyl)-1H-pyrazole-5-amine

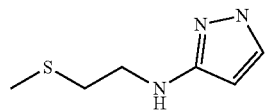

Yield: 84%
The compound is used without further analyses.

4) Preparation of N-(2-methoxyethyl)aniline

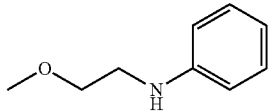

1,1-Dimethoxy-2-(methyloxy)ethane (10 g, 83.23 mmol, 1.0 eq) is dissolved in HCl solution (0.5 M, 1.0 eq) and stirred at 50° C. for 1 h. The reaction mixture is cooled down to RT and extracted with CH₂Cl₂ (3 mL/mmol in total). The combined organic phases are dried over Na₂SO₄. The aldehyde solution is cooled to 0° C. and then admixed with aniline (7.75 g, 83.23 mmol, 1.0 eq), sodium cyanoborohydride (5.75 g, 91.55 mmol, 1.1 eq) and acetic acid (4.7 mL, 83.23 mmol, 1.0 eq). The reaction mixture is stirred at RT for 16 h. The reaction is ended by the addition of NaHCO₃ solution. The aqueous phase is extracted three times with CH₂Cl₂, and the combined organic phases are dried over Na₂SO₄ and concentrated under reduced pressure. The crude product is purified by flash chromatography (hexane:EtOAc=19:1).

Yield: 19%
The compound is used without further analyses.

5) Preparation of Cinnamides or Phenoxyacetamides of the Invention

Method A

Cinnamic acid or phenoxyacetic acid (1.5 eq) and N-methylformanilide (MFA) (1 drop) are dissolved in CH₂Cl₂ (5 mL/mmol), cooled to 0° C. and admixed with oxalyl chloride (3.0 eq). The reaction mixture is stirred at RT for 2 h and at 40° C. for 1 h and concentrated under reduced pressure. Triethylamine (4.0 eq) and the respective amine (1.0 eq) are dissolved in CH₂Cl₂ (4 ml/mmol) and cooled to 0° C. The crude product is dissolved in CH₂Cl₂ (1 mL/mmol) and slowly added dropwise. The reaction mixture is stirred at RT for 16 h. The reaction is ended by the addition of NaHCO₃ solution. The aqueous phase is extracted with CH₂Cl₂ (3×), and the combined organic phase is dried over Na₂SO₄ and concentrated under reduced pressure. The crude product is purified by flash chromatography.

Method B:

Cinnamic acid or phenoxyacetic acid (2.0 eq) and MFA (1 drop) are dissolved in CH₂Cl₂ (5 mL/mmol), cooled to 0° C. and admixed with oxalyl chloride (4.2 eq). The reaction mixture is stirred at RT for 2 h and at 40° C. for 1 h and concentrated under reduced pressure. Pyridine (2.0 eq) and the respective amine (1.0 eq) are dissolved in CH₂Cl₂ (4 mL/mmol) and cooled to 0° C. The crude product is dissolved in CH₂Cl₂ (1 mL/mmol) and slowly added dropwise. The reaction mixture is stirred at RT for 16 h. The reaction is ended by the addition of NaHCO₃ solution. The aqueous phase is extracted with CH₂Cl₂ (3×), and the combined organic phase is dried over Na₂SO₄ and concentrated under reduced pressure. The crude product is dissolved in ethanol (15 mL/mmol) and admixed with NaOH (5.0 eq). After 15 min, the solvent is removed under reduced pressure and the crude product is admixed with water and extracted three times with CH₂Cl₂. The combined organic phases are dried over Na₂SO₄ and concentrated under reduced pressure. The product is purified by flash chromatography (EtOAc:hexane=25:75→45:55).

6) Preparation of (E)-3-(1,3-benzodioxol-5-yl)-N-(2-methylsulfanylethyl)-N-phenylprop-2-enamide

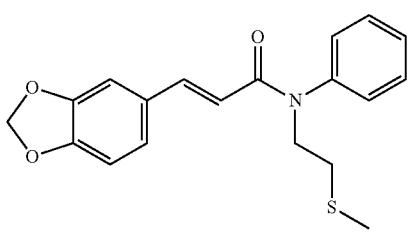

Method A: 71% yield
¹H NMR (400 MHz, chloroform-d) δ 7.59 (d, J=15.5 Hz, 1H), 7.49-7.41 (m, 2H), 7.41-7.35 (m, 1H), 7.28-7.22 (m, 2H), 6.85 (dd, J=8.1, 1.7 Hz, 1H), 6.73 (d, J=8.1 Hz, 1H), 6.73 (d, J=1.7 Hz, 1H), 6.10 (d, J=15.4 Hz, 1H), 5.93 (s, 2H), 4.06-3.99 (m, 2H), 2.74-2.68 (m, 2H), 2.16 (s, 3H).

7) Preparation of 2-(4-methylphenoxy)-N-(2-methylsulfanylethyl)-N-phenylacetamide

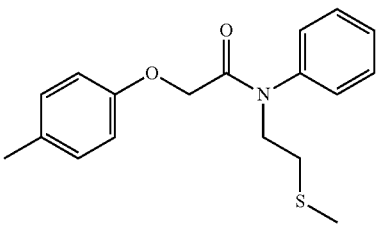

Method A: 87% yield
$^1$H NMR (400 MHz, chloroform-d) δ 7.46 (dd, J=8.3, 6.4 Hz, 2H), 7.43-7.37 (m, 1H), 7.30-7.23 (m, 2H), 7.01 (d, J=8.4 Hz, 2H), 6.67 (d, J=8.6 Hz, 2H), 4.34 (s, 2H), 3.98-3.90 (m, 2H), 2.70-2.61 (m, 2H), 2.25 (s, 3H), 2.13 (s, 3H).

8) Preparation of (E)-3-(1,3-benzodioxol-5-yl)-N-ethyl-N-(2-methylsulfanylethyl)prop-2-enamide

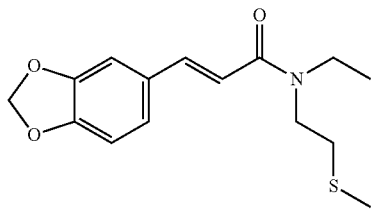 [SMILES: CCN(CCSC)C(=O)/C=C/c1ccc2c(c1)OCO2]

Method A: 31% yield
$^1$H NMR (400 MHz, chloroform-d) δ 7.63 (d, J=15.2 Hz, 2H), 7.06-6.96 (m, 4H), 6.81 (d, J=8.0 Hz, 2H), 6.66 (dd, J=15.0, 6.4 Hz, 2H), 6.00 (s, 4H), 3.62 (dd, J=8.6, 6.4 Hz, 4H), 3.52 (q, J=7.2 Hz, 4H), 2.78-2.68 (m, 4H), 2.19 (s, 6H), 1.26 (t, J=7.2 HZ, 3H), 1.19 (t, J=7.3 Hz, 3H).

9) Preparation of (E)-3-(1,3-benzodioxol-5-yl)-N-(2-methylsulfanylethyl)-N-(2-pyridyl)prop-2-enamide

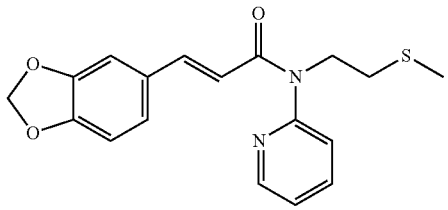 [SMILES: CSCCN(C(=O)/C=C/c1ccc2c(c1)OCO2)c1ccccn1]

Method A: 5% yield
$^1$H NMR (400 MHz, chloroform-d) δ 8.55 (ddd, J=4.9, 2.0, 0.9 Hz, 1H), 7.75 (td, J=7.7, 2.0 Hz, 1H), 7.64 (d, J=15.4 Hz, 1H), 7.23 (ddd, J=7.4, 2.7, 1.0 Hz, 2H), 6.90 (dd, J=8.2, 1.7 Hz, 1H), 6.81 (d, J=1.7 Hz, 1H), 6.76 (d, J=8.0 Hz, 1H), 6.26 (d, J=15.4 Hz, 1H), 5.96 (s, 2H), 4.26-4.16 (m, 2H), 2.89-2.75 (m, 2H), 2.15 (s, 3H).

10) Preparation of (E)-N-(2-methylsulfanylethyl)-3-(p-tolyl)-N-(2-pyridyl)prop-2-enamide

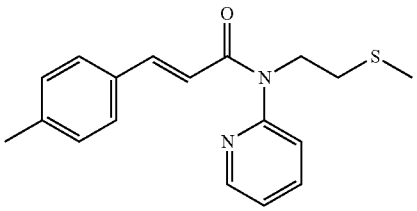

Method A: 10% yield
$^1$H NMR (400 MHz, chloroform-d) δ 8.55 (dd, J=5.4, 2.0 Hz, 1H), 7.75 (td, J=7.8, 2.0 Hz, 1H), 7.71 (d, J=15.4 Hz, 1H), 7.29-7.21 (m, 4H), 7.12 (d, J=7.9 Hz, 2H), 6.40 (d, J=15.5 Hz, 1H), 4.30-4.16 (m, 2H), 2.87-2.74 (m, 2H), 2.33 (s, 3H), 2.15 (s, 3H).

11) Preparation of (E)-3-(1,3-benzodioxol-5-yl)-N-(2-methylsulfanylethyl)-N-(1H-pyrazol-3-yl)prop-2-enamide

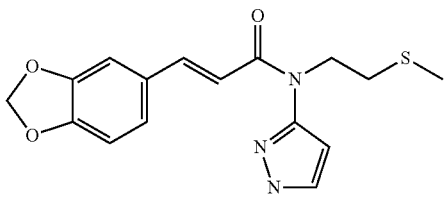 [SMILES: CSCCN(C(=O)/C=C/c1ccc2c(c1)OCO2)c1cc[nH]n1]

Method B: 10% yield
$^1$H NMR (400 MHz, chloroform-d) δ 7.63 (d, J=15.2 Hz, 1H), 7.61 (d, J=2.4 Hz, 1H), 6.90 (d, J=7.9 Hz, 1H), 6.83 (s, 1H), 6.74 (d, J=8.0 Hz, 1H), 6.35 (d, J=14.7 Hz, 1H), 6.25 (s, 1H), 5.95 (s, 2H), 4.03 (t, J=7.3 Hz, 2H), 2.78 (t, J=7.6 Hz, 2H), 2.16 (s, 3H).

12) Preparation of (E)-N-ethyl-N-(2-methylsulfanylethyl)-3-(p-tolyl)prop-2-enamide

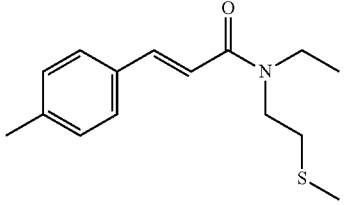

Method A: 41% yield
Two rotamers at the nitrogen are apparent in the spectrum.
$^1$H NMR (400 MHz, chloroform-d) δ 7.69 (d, J=15.3 Hz, 2H), 7.42 (d, J=7.8 Hz, 4H), 7.18 (d, J=7.9 Hz, 4H), 6.79 (dd, J=15.4, 5.7 Hz, 2H), 3.67-3.57 (m, 4H), 3.53 (q, J=7.1 Hz, 4H), 2.78-2.68 (m, 4H), 2.37 (s, 6H), 2.19 (s, 6H), 1.27 (t, J=7.1 Hz, 3H), 1.20 (t, J=7.1 Hz, 3H).

13) Preparation of (E)-N-ethyl-3-(4-methoxyphenyl)-N-(2-methylsulfanylethyl)prop-2-enamide

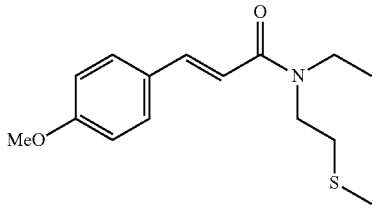 [SMILES: CCN(CCSC)C(=O)/C=C/c1ccc(OC)cc1]

Method A: 12% yield

¹H NMR (400 MHz, chloroform-d) δ 7.69 (d, J=15.3 Hz, 1H), 7.53-7.44 (m, 2H), 6.96-6.83 (m, 2H), 6.70 (d, J=15.3 Hz, 1H), 3.83 (s, 3H), 3.62 (dd, J=8.5, 6.6 Hz, 2H), 3.53 (q, J=7.1 Hz, 2H), 2.78-2.69 (m, 2H), 2.19 (s, 3H), 1.27-1.19 (m, 3H).

14) Preparation of (E)-N-(2-methylsulfanylethyl)-N-phenyl-3-(p-tolyl)prop-2-enamide

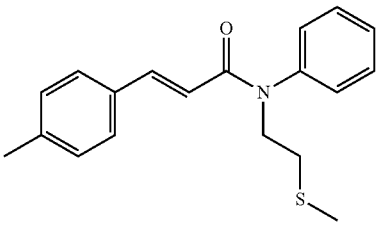 [SMILES: CSCCN(C(=O)/C=C/c1ccc(C)cc1)c1ccccc1]

Method A: 79% yield

¹H NMR (400 MHz, chloroform-d) δ 7.65 (d, J=15.5 Hz, 1H), 7.48-7.41 (m, 2H), 7.41-7.35 (m, 1H), 7.29-7.23 (m, 2H), 7.19 (d, J=8.1 Hz, 2H), 7.08 (d, J=8.0 Hz, 2H), 6.23 (d, J=15.5 Hz, 1H), 4.07-3.99 (m, 2H), 2.75-2.67 (m, 2H), 2.31 (s, 3H), 2.16 (s, 3H).

15) Preparation of (E)-3-(4-methoxyphenyl)-N-(2-methylsulfanylethyl)-N-phenylprop-2-enamide

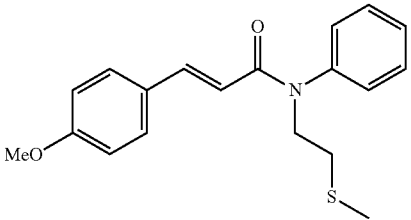 [SMILES: COc1ccc(/C=C/C(=O)N(CCSC)c2ccccc2)cc1]

Method A: 85% yield

¹H NMR (400 MHz, chloroform-d) δ 7.64 (d, J=15.5 Hz, 1H), 7.48-7.41 (m, 2H), 7.42-7.34 (m, 1H), 7.28-7.21 (m, 4H), 6.82-6.78 (m, 2H), 6.15 (d, J=15.5 Hz, 1H), 4.06-4.00 (m, 2H), 3.78 (s, 3H), 2.75-2.67 (m, 2H), 2.16 (s, 3H).

16) Preparation of 2-(4-methoxyphenoxy)-N-(2-methylsulfanylethyl)-N-phenylacetamide

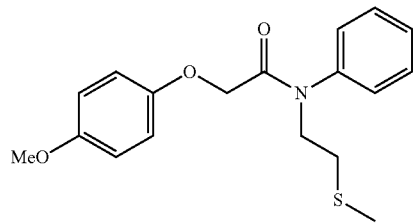 [SMILES: COc1ccc(OCC(=O)N(CCSC)c2ccccc2)cc1]

Method A: 89% yield

¹H NMR (400 MHz, chloroform-d) δ 7.50-7.41 (m, 2H), 7.40 (s, 1H), 7.29-7.22 (m, 2H), 6.76 (t, J=9.1 Hz, 2H), 6.71 (s, 2H), 4.32 (s, 2H), 3.99-3.88 (m, 2H), 3.73 (s, 3H), 2.72-2.59 (m, 2H), 2.13 (s, 3H).

17) Preparation of (E)-N-ethyl-N-(3-methylsulfanylpropyl)-3-(p-tolyl)prop-2-enamide

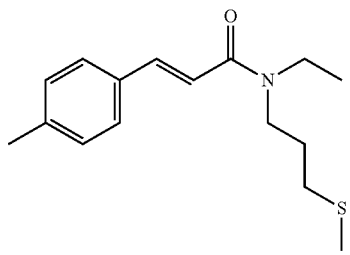

Method A: 50% yield

Two rotamers at the nitrogen are apparent in the spectrum.

¹H NMR (400 MHz, chloroform-d) δ 7.69 (d, J=15.3 Hz, 2H), 7.47-7.39 (m, 4H), 7.18 (d, J=7.9 Hz, 4H), 6.93 (d, J=15.4 Hz, 1H), 6.79 (d, J=15.4 Hz, 1H), 3.51 (dt, J=14.2, 7.8 Hz, 8H), 2.55 (t, J=7.0 Hz, 4H), 2.37 (s, 6H), 2.11 (s, 6H), 1.99-1.87 (m, 4H), 1.39-1.08 (m, 6H).

18) Preparation of (E)-3-(1,3-benzodioxol-5-yl)-N-ethyl-N-(3-methylsulfanylpropyl)prop-2-enamide

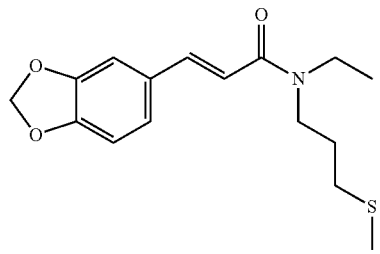 [SMILES: CCN(CCCSC)C(=O)/C=C/c1ccc2c(c1)OCO2]

Method A: 66% yield

Two rotamers at the nitrogen are apparent in the spectrum.

¹H NMR (400 MHz, chloroform-d) δ 7.62 (d, J=15.3 Hz, 2H), 7.11-6.97 (m, 4H), 6.87-6.76 (m, 2H), 6.66 (d, J=15.3 Hz, 2H), 5.99 (s, 4H), 3.59-3.43 (m, 8H), 2.62-2.49 (m, 4H), 2.12 (s, 6H), 1.99-1.90 (m, 4H), 1.26 (t, J=7.1 Hz, 3H), 1.19 (t, J=7.1 Hz, 3H).

19) Preparation of (E)-3-(1,3-benzodioxol-5-yl)-N-(3-methylsulfanylpropyl)-N-phenylprop-2-enamide

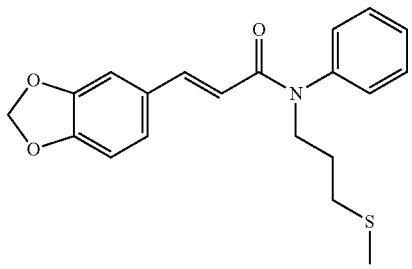 [SMILES: CSCCCN(C(=O)/C=C/c1ccc2c(c1)OCO2)c1ccccc1]

Method A: 98% yield

¹H NMR (400 MHz, chloroform-d) δ 7.57 (d, J=15.4 Hz, 1H), 7.48-7.42 (m, 2H), 7.41-7.34 (m, 1H), 7.23-7.18 (m, 2H), 6.85 (dd, J=8.1, 1.7 Hz, 1H), 6.73-6.72 (m, 2H), 6.72 (d, J=8.0 Hz, 1H), 6.10 (d, J=15.4 Hz, 1H), 5.93 (s, 2H), 3.95-3.89 (m, 2H), 2.56-2.49 (m, 2H), 2.06 (s, 3H), 1.94-1.84 (m, 2H).

20) Preparation of (E)-3-(1,3-benzodioxol-5-yl)-N-(2-methoxyethyl)-N-phenylprop-2-enamide

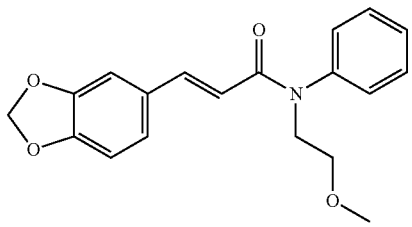 [SMILES: COCCN(C(=O)/C=C/c1ccc2c(c1)OCO2)c1ccccc1]

Method A: 61% yield

¹H NMR (400 MHz, chloroform-d) δ 7.58 (d, J=15.5 Hz, 1H), 7.46-7.40 (m, 2H), 7.40-7.33 (m, 1H), 7.29-7.24 (m, 2H), 6.85 (dd, J=8.1, 1.6 Hz, 1H), 6.73 (d, J=1.8 Hz, 1H), 6.73 (d, J=8.0 Hz, 1H), 6.12 (d, J=15.4 Hz, 1H), 5.93 (s, 2H), 4.00 (t, J=5.8 Hz, 2H), 3.60 (t, J=5.8 Hz, 2H), 3.33 (s, 3H).

21) Preparation of (E)-3-(4-methoxyphenyl)-N-(2-methylsulfanylethyl)-N-(2-pyridyl)prop-2-enamide

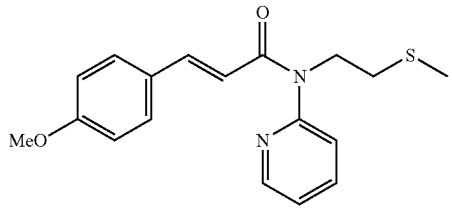 [SMILES: COc1ccc(/C=C/C(=O)N(CCSC)c2ccccn2)cc1]

Method A: 10% yield

¹H NMR (400 MHz, chloroform-d) δ 8.55 (d, J=5.7 Hz, 1H), 7.75 (td, J=7.7, 2.0 Hz, 1H), 7.69 (d, J=15.5 Hz, 1H), 7.35-7.28 (m, 2H), 7.23 (dd, J=7.5, 4.5 Hz, 2H), 6.94-6.73 (m, 2H), 6.31 (d, J=15.4 Hz, 1H), 4.26-4.18 (m, 2H), 3.80 (s, 3H), 2.85-2.76 (m, 2H), 2.15 (s, 3H).

22) Preparation of 2-(4-methylphenoxy)-N-(2-methylsulfanylethyl)-N-(2-pyridyl)acetamide

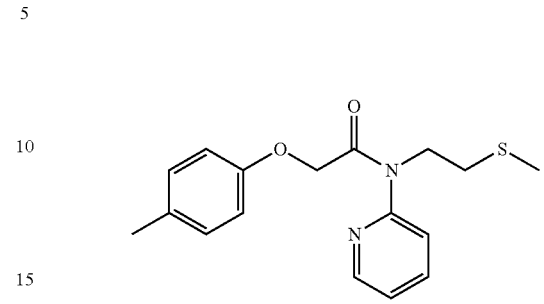

Method A: 19% yield

¹H NMR (400 MHz, chloroform-d) δ 8.50-8.44 (m, 1H), 7.77 (td, J=7.8, 2.0 Hz, 1H), 7.30-7.25 (m, 1H), 7.23 (ddd, J=7.3, 5.0, 0.7 Hz, 1H), 7.01 (d, J=8.3 Hz, 2H), 6.64 (d, J=8.5 Hz, 2H), 4.68 (s, 2H), 4.10-4.00 (m, 2H), 2.77-2.69 (m, 2H), 2.25 (s, 3H), 2.12 (s, 3H).

23) Preparation of (E)-N-(2-methylsulfanylethyl)-3-(p-tolyl)-N-(1H-pyrazol-3-yl)prop-2-enamide

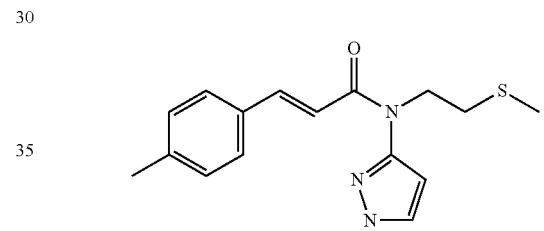

Method B: 50% yield

¹H NMR (600 MHz, chloroform-d) δ 10.91 (s, 1H), 7.69 (d, J=15.5 Hz, 1H), 7.60 (d, J=1.6 Hz, 1H), 7.26 (d, J=5.5 Hz, 2H), 7.10 (d, J=7.5 Hz, 2H), 6.46 (d, J=14.6 Hz, 1H), 6.24 (s, 1H), 4.04 (t, J=13.1, 6.2 Hz, 2H), 2.78 (t, J=7.4 Hz, 2H), 2.32 (s, 3H), 2.16 (s, 3H).

24) Preparation of 2-(4-methylphenoxy)-N-(2-methylsulfanylethyl)-N-(1H-pyrazol-3-yl)acetamide

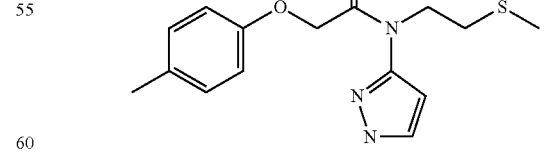

Method B: 64% yield

¹H NMR (400 MHz, chloroform-d) δ 7.57 (d, J=2.5 Hz, 1H), 7.00 (d, J=8.2 Hz, 2H), 6.71 (d, J=8.4 Hz, 2H), 6.23 (d, J=2.4 Hz, 1H), 4.53 (s, 2H), 4.01-3.83 (m, 2H), 2.77-2.62 (m, 2H), 2.23 (s, 3H), 2.11 (s, 3H).

25) Preparation of 2-(4-methoxyphenoxy)-N-(2-methylsulfanylethyl)-N-(1H-pyrazol-3-yl)acetamide

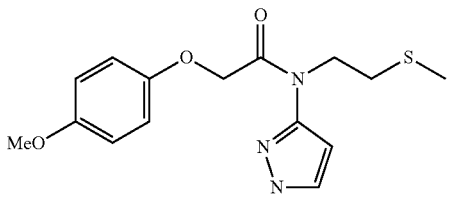 [SMILES: COc1ccc(OCC(=O)N(CCSC)c2cc[nH]n2)cc1]

Method B: 53% yield
$^1$H NMR (400 MHz, chloroform-d) δ 10.72 (s, 1H), 7.58 (d, J=2.4 Hz, 1H), 6.77 (s, 4H), 6.24 (d, J=2.4 Hz, 1H), 4.54 (s, 2H), 3.93 (dd, J=8.5, 6.3 Hz, 2H), 3.73 (s, 3H), 2.72 (dd, J=8.6, 6.2 Hz, 2H), 2.13 (s, 3H).

26) Preparation of (E)-3-(1,3-benzodioxol-5-yl)prop-2-enoyl Chloride

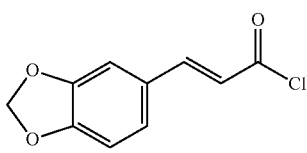 [SMILES: O=C(Cl)/C=C/c1ccc2c(c1)OCO2]

An initial charge of 52.7 g (274.2 mmol) of 3,4-dioxymethylenecinnamic acid, 529 mL of toluene and 1.60 g of DMF is heated to 57° C. Within 30 min, 44.1 g (371 mmol) of thionyl chloride is added dropwise at 57 to 60° C. The solution is stirred at 60 to 65° C. for a further 1 h and then concentrated to a volume of about 300 mL. 3×289 mL of toluene is added, and each portion is distilled off again under standard pressure.

27) Preparation of (E)-3-(1,3-benzodioxol-5-yl)-N-phenyl-N-tetrahydrofuran-3-ylprop-2-enamide

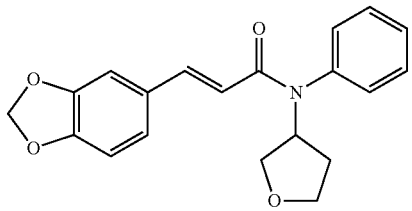 [SMILES: O=C(/C=C/c1ccc2c(c1)OCO2)N(c1ccccc1)C1CCOC1]

To 0.72 g (3.4 mmol) of 3,4-methylenedioxycinnamoyl chloride in 7.5 g of toluene are added, at 50° C., 0.52 g (5.14 mmol) of triethylamine and then 0.52 g (3.19 mmol) of N-phenyloxolane-3-amine in 4 mL of toluene. The mixture is stirred at 60° C. for 8 h and cooled down to RT. The organic phase is washed with water, 1 N hydrochloric acid, water, saturated NaHCO$_3$ solution and water again, dried over Na$_2$SO$_4$, filtered and concentrated.
Yield: 39%
$^1$H NMR (500 MHz, CDCl$_3$) δ 7.56 (d, J=15.4 Hz, 1H); 7.50-7.38 (m, 3H); 7.22-7.12 (m, 2H); 6.81 (dd, J=8.2, 1.6 Hz, 1H); 6.71 (d, J=8.0 Hz, 1H); 6.67 (d, J=1.6 Hz, 1H); 5.96-5.85 (m, 3H); 5.29 (dq, J=8.3, 5.5 Hz, 2H); 4.04 (dd, J=9.3, 6.7 Hz, 1H); 3.79 (dd, J=9.3, 5.1 Hz, 1H); 3.74-3.53 (m, 1H); 2.20-2.12 (m, 1H); 1.96-1.77 (m, 1H).

28) Preparation of (E)-N-phenyl-3-(p-tolyl)-N-tetrahydrofuran-3-ylprop-2-enamide

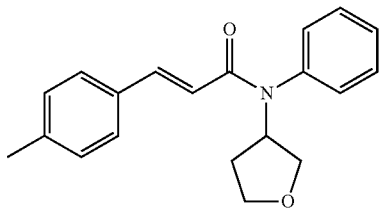

To a solution of 0.56 g (3.0 mmol) of 4-methylcinnamoyl chloride in 7.5 mL of toluene is added dropwise 0.46 g (4.5 mmol) of triethylamine. Subsequently, within 2 min, a suspension of 0.46 g (2.8 mmol) of N-phenyltetrahydrofuran-3-amine in 4 mL of toluene is metered in. The mixture is stirred at RT for 46 h and at 50° C. for 11 h. 20 mL of water is added for workup, and the organic phase is removed and concentrated on a rotary evaporator. The residue is recrystallized from ethyl acetate/heptane.
Yield: 0.32 g of product
$^1$H NMR (500 MHz, CDCl$_3$) δ 7.63 (d, 1H), 7.50-7.40 (m, 3H), 7.22 (d, 2H), 7.14 (d, 2H), 7.07 (d, 2H), 6.06 (d, 1H), 5.34-5.26 (m, 1H), 4.05 (t, 1H), 3.83-3.78 (m, 1H), 3.71 (dd, 1H), 3.61 (dd, 1H), 2.30 (s, 3H); 2.25-2.14 (m, 1H); 1.90-1.81 (m, 1H).

29) Preparation of N-phenyltetrahydrothiophene-3-amine

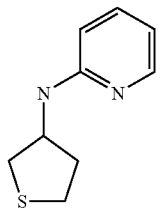 [SMILES: c1ccc(NC2CCSC2)nc1]

A reactor is initially charged with 91.1 g (0.968 mol) of 2-aminopyridine, 1591 mL of toluene, 98.4 g (0.963 mol) of tetrahydrothiophene-3-one and 81.6 g of acetic acid. At room temperature, 288 g (1.36 mol) of sodium triacetoxyborohydride is added in portions within 30 min. The residue is rinsed in with 115 mL of toluene and the mixture is stirred at room temperature for 21 h. Subsequently, the mixture is metered into 4.85 L of aqueous 10% Na$_2$CO$_3$ solution at 15° C. and admixed with a further 500 mL of toluene. Stirring is continued at 15-20° C. for about 20 minutes, and the aqueous phase is removed and extracted once again with 500 mL of toluene. The organic phases are combined and admixed with 2 L of water and 280 g of 10% HCl. The mixture is stirred for a further 10 min and the organic phase is removed and discarded. The aqueous phase is washed 2× with 500 mL each time of toluene, which are likewise discarded. Subsequently, the aqueous phase is admixed with 2 L of water and 1 L of toluene, and adjusted to pH 10.3 with 274 mL of 10% NaOH. The mixture is stirred for a further 10 min, the organic phase is removed and the aqueous phase is re-extracted once more with 250 mL of toluene. The combined organic phases are washed 1× with 200 mL of water, dried over Na₂SO₄ and concentrated.

Residue: 45.3 g (28%)

30) Preparation of (E)-3-(1,3-benzodioxol-5-yl)-N-(2-pyridyl)-N-tetrahydrothiophen-3-ylprop-2-enamide

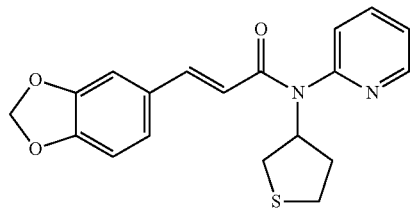

To a solution of about 57.7 g (274 mmol) of 3,4-methylenedioxycinnamoyl chloride in about 235 mL of toluene are added, at about 50° C., 41.6 g (0.411 mol) of triethylamine and 46.5 g (258 mmol) of N-phenyltetrahydrothiophene-3-amine in 264 mL of toluene. The mixture is stirred at 55° C. for 1 h and then at RT overnight. The suspension is cooled down to 0° C. and filtered. The filter residue is taken up in 2 L of ethyl acetate and, at 40° C., washed 3× with 500 mL of water each time. The mixture is concentrated to a volume level of about 600 mL at standard pressure, cooled down to about 0° C. within 3 h and stirred for a further 1 h. This is followed by filtering and washing of the filtercake with 80 mL of ice-cold ethyl acetate. The filtercake is dried, taken up in 1670 mL of isopropanol and heated to reflux (solution). The mixture is concentrated to a volume level of 670 mL, cooled down to 20° C. and filtered. The residue is washed with 50 mL of ice-cold i-PrOH and dried.

Residue: 59.8 g (yield: 62%)

¹H NMR (500 MHz, CDCl₃) δ 8.63 (d, 1H); 7.84 (td, J=7.7, 2.0 Hz, 1H); 7.60 (d, J=15.3 Hz, 1H); 7.39 (ddd, J=7.5, 4.9, 0.9 Hz, 1H); 7.22 (d, J=7.8 Hz, 1H); 6.82 (d, 1H); 6.72 (d, J=8.0 Hz, 1H); 6.68 (d, J=1.6 Hz, 1H); 5.94 (s, 2H); 5.80 (d, J=15.3 Hz, 1H); 5.32-5.15 (m, 1H); 3.12 (dd, J=10.1, 6.9 Hz, 1H); 2.94-2.81 (m, 2H); 2.72 (ddd, J=10.3, 7.8, 2.4 Hz, 1H); 2.35-2.25 (m, 1H); 1.90-1.79 (m, 1H).

31) Preparation of (E)-3-(p-tolyl)-N-(2-pyridyl)-N-tetrahydrothiophen-3-ylprop-2-enamide

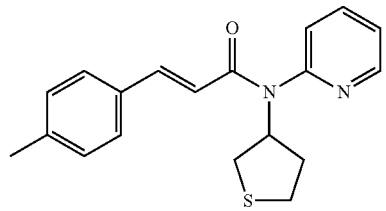

To an initial charge of 0.74 g (4.1 mmol) of 4-methylcinnamoyl chloride in 10 mL of toluene is added 0.52 g (5.1 mmol) of triethylamine. Subsequently, 0.65 g 3.4 mmol) of N-tetrahydrothiophen-3-ylpyridine-2-amine in 4.8 mL of toluene is metered in and the mixture is stirred at 50° C. for 1 h. The mixture is quenched at RT with 20 mL of water. The precipitated solids are filtered off, washed with water and a little MTBE, and dried.

Yield: 57%

¹H NMR (500 MHz, CDCl₃) δ 8.64 (br s, 1H); 7.83 (td, J=7.7, 2.0 Hz, 1H); 7.67 (d, J=15.4 Hz, 1H); 7.39 (dd, J=7.5, 4.9 Hz, 1H); 7.22 (d, J=7.8 Hz, 1H); 7.16 (d, J=8.1 Hz, 2H); 7.07 (d, J=8.0 Hz, 2H); 5.94 (d, J=15.4 Hz, 1H); 5.32-5.20 (m, 1H); 3.13 (dd, J=10.2, 6.9 Hz, 1H); 2.96-2.80 (m, 2H); 2.78-2.66 (m, 1H); 2.40-2.23 (m, 4H); 1.94-1.78 (m, 1H).

32) Preparation of (E)-3-(4-methoxyphenyl)-N-(2-pyridyl)-N-tetrahydrothiophen-3-ylprop-2-enamide

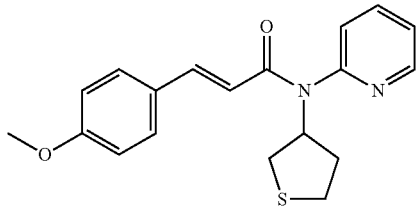 [SMILES: COc1ccc(/C=C/C(=O)N(c2ccccn2)C2CCSC2)cc1]

To an initial charge of 0.81 g (4.1 mmol) of 4-methoxycinnamoyl chloride in 11 mL of toluene is added 0.52 g (5.1 mmol) of triethylamine. Subsequently, 0.65 g (3.4 mmol) of N-tetrahydrothiophen-3-ylpyridine-2-amine in 4.8 mL of toluene is metered in and the mixture is stirred at 50 to 60° C. for 1 h. The mixture is quenched at RT with 20 mL of water. The precipitated solids are filtered off, washed with water and a little MTBE, and dried.

Yield: 69%

¹H NMR (500 MHz, CDCl₃) δ 8.65 (d, 1H); 7.83 (td, J=7.7, 1.8 Hz, 1H); 7.65 (d, J=15.4 Hz, 1H); 7.39 (dd, J=7.3, 5.0 Hz, 1H); 7.22 (d, J=8.6 Hz, 3H); 6.80 (d, J=8.7 Hz, 2H); 5.85 (d, J=15.4 Hz, 1H); 5.32-5.20 (m. 1H), 3.78 (s, 3H); 3.13 (dd, J=10.1, 6.9 Hz, 1H); 2.97-2.80 (m, 2H); 2.75-2.69 (m, 1H); 2.35-2.25 (m, 1H); 1.94-1.74 (m, 1H).

33) Preparation of (E)-3-phenyl-N-(2-pyridyl)-N-tetrahydrothiophen-3-ylprop-2-enamide

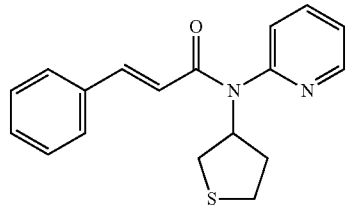 [SMILES: O=C(/C=C/c1ccccc1)N(c1ccccn1)C1CCSC1]

To an initial charge of 0.68 g (4.1 mmol) of cinnamoyl chloride in 9 mL of toluene is added 0.52 g (5.1 mmol) of triethylamine. Subsequently, 0.65 g (3.4 mmol) of N-tetrahydrothiophen-3-ylpyridine-2-amine in 4.8 mL of toluene is metered in and the mixture is stirred at 50 to 60° C. for 1 h. The mixture is quenched at RT with 20 mL of water and the organic phase is washed once again with 20 mL of water. The organic phase is dried over Na₂SO₄, filtered and concentrated by rotary evaporation. This is followed by recrystallization from n-heptane/EtOAc.

Yield: 50%

¹H NMR (500 MHz, CDCl₃) δ 8.65 (dd, J=4.8, 1.8 Hz, 1H); 7.84 (td, J=7.7, 2.0 Hz, 1H); 7.70 (d, J=15.4 Hz, 1H); 7.42-7.35 (m, 1H); 7.32-7.12 (m, 6H); 5.99 (d, J=15.4 Hz, 1H); 5.35-5.13 (m, 1H); 3.14 (dd, J=10.2, 6.9 Hz, 1H); 2.97-2.81 (m, 2H); 2.72 (m, 1H); 2.31 (m, Hz, 1H); 1.99-1.70 (m, 1H).

34) Preparation of N-(tetrahydrofuran-2-ylmethyl)aniline

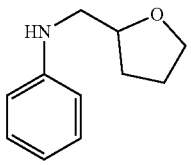 [SMILES: c1ccc(NCC2CCCO2)cc1]

96.1 g (1.0 mol) of furfural is initially charged in 400 g of methylene chloride. Subsequently, 111.8 g (1.2 mol) of aniline is added dropwise at 40° C. The mixture is cooled to 0° C., and 400 g of methanol and 56.7 g (1.5 mol) of sodium boronate are added cautiously, and the mixture is stirred at 0 to 5° C. for 1 h. The mixture is quenched with water, and methanol is distilled out. Thereafter, the mixture is neutralized with 450 g of HCl (10%) and extracted with MTBE. The organic phase is dried and condensed, and the product is distilled and used without further purification.

100 g of furfurylphenylamine is initially charged in 250 mL of ethanol, and 4 g of Pd/C is added. The reactor is supplied with hydrogen (10 bar) and the mixture is stirred at 50° C. for 18 h. The mixture is filtered at RT and distilled directly.

Yield: 58%

Preparation of (E)-3-81,3-benzodioxo-5-yl)-N-phenyl-N-(tetrahydrofuran-2-ylmethyl)prop-2-enamide

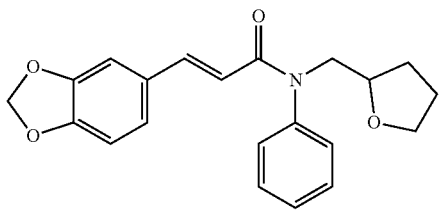 [SMILES: O=C(/C=C/c1ccc2c(c1)OCO2)N(CC1CCCO1)c1ccccc1]

1.14 g (11.3 mmol) of triethylamine and 1.95 g (11 mmol) of 2-tetrahydrofurfurylphenylamine are initially charged in 30 g of toluene. Subsequently, 4.52 g (21.5 mmol) of 3,4-methylenedioxycinnamoyl chloride is metered in and the mixture is stirred at 100° C. for a further 2 h. The mixture is poured onto 50 g of water at RT and the solids are filtered off with suction. After phase separation, the organic phase is dried, filtered and concentrated by rotary evaporation. This is followed by passage through a silica gel column (AcOEt).

Yield: 76%

¹H NMR (400 MHz, chloroform-d) δ 7.58 (d, J=15.5 Hz, 1H), 7.47-7.39 (m, 2H), 7.39-7.33 (m, 2H), 7.33-7.28 (m, 1H), 6.84 (dd, J=8.1, 1.7 Hz, 1H), 6.72 (d, J=1.6 Hz, 1H), 6.70 (d, J=7.9 Hz, 1H), 6.13 (d, J=15.5 Hz, 1H), 5.92 (s, 2H), 4.21-4.08 (m, 1H), 4.00 (dd, J=13.7, 4.8 Hz, 1H), 3.89-3.81 (m, 1H), 3.84-3.75 (m, 1H), 3.77-3.68 (m, 1H), 1.98 (ddd, J=6.9, 4.2, 1.9 Hz, 1H), 1.96-1.79 (m, 2H), 1.68-1.54 (m, 1H).

35) The Following Compounds can Also be Prepared Analogously to the Methods Described Above (E)-3-(4-Methoxyphenyl)-N-phenyl-N-tetrahydrofuran-3-ylprop-2-enamide

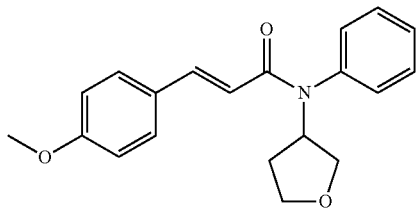 [SMILES: COc1ccc(/C=C/C(=O)N(c2ccccc2)C2CCOC2)cc1]

¹H NMR (500 MHz, CD₂Cl₂) δ 7.52 (d, 1H); 7.48-7.35 (m, 3H); 7.27-7.11 (m, 4H); 6.77 (d, 2H); 5.97 (d, 1H); 5.29-5.13 (m, 1H); 3.95 (dd, 1H); 3.74 (s, 3H); 3.70 (dd, 1H); 3.63 (q, 1H); 3.54 (td, 1H); 2.21-2.05 (m, 1H); 1.74-1.36 (m, 1H).

2-(4-Methylphenoxy)-N-phenyl-N-tetrahydrofuran-3-ylacetamide

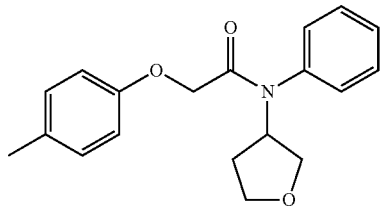

¹H NMR (500 MHz, CDCl₃) δ 7.56-7.36 (m, 3H); 7.30-7.16 (m, 2H); 7.02 (d, 2H); 6.66 (d, 2H); 5.25-5.09 (m, 1H); 4.25 (d, 1H); 4.21 (d, 1H); 3.98 (dd, 1H); 3.78 (dd, 1H); 3.67 (td, 1H); 3.60-2.48 (m, 1H); 2.25 (s, 3H); 2.23-2.07 (m, 1H); 1.85-1.75 (m, 1H).

2-(4-Methylphenoxy)-N-phenyl-N-tetrahydrothiophen-3-ylacetamide

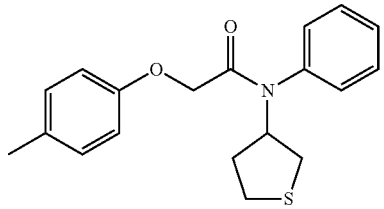

¹H NMR (500 MHz, CDCl₃) δ 7.55-7.35 (m, 3H); 7.24-7.15 (m, 2H); 7.02 (d, 2H); 6.66 (d, 2H); 5.34-4.97 (m, 1H); 4.22 (s, 2H); 3.04 (dd, 1H); 2.84 (td, 1H); 2.74-2.50 (m, 2H); 2.37-2.10 (m, 4H); 1.65 (qd, 1H).

133

(E)-N-Cyclohexyl-3-(4-methoxyphenyl)-N-(3-thienyl)prop-2-enamide

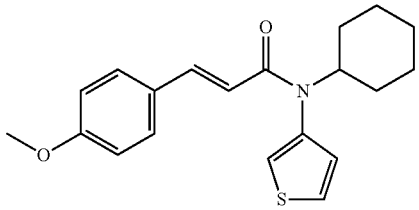 [SMILES: COc1ccc(/C=C/C(=O)N(c2ccsc2)C2CCCCC2)cc1]

¹H NMR (500 MHz, CDCl₃) δ 7.60 (d, 1H); 7.37 (dd, 1H); 7.25 (d, 2H); 7.08 (dd, 1H); 6.88 (dd, 1H); 6.81 (d, 2H); 6.05 (d, 1H); 4.71-4.61 (m, 1H); 3.79 (s, 3H); 1.86 (d, 2H); 1.76 (d, 2H); 1.61 (d, 1H); 1.44 (qt, 2H); 1.13 (qd, 2H); 1.03-0.90 (m, 1H).

N-Cyclohexyl-2-(4-methylphenoxy)-N-(3-thienyl)acetamide

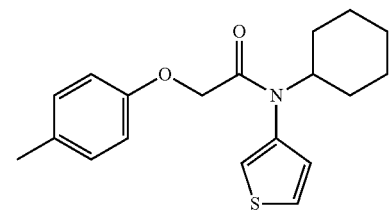 [SMILES: Cc1ccc(OCC(=O)N(c2ccsc2)C2CCCCC2)cc1]

¹H NMR (500 MHz, CDCl₃) δ 7.45-7.30 (m, 1H); 7.16-7.08 (m, 1H); 7.02 (d, 2H); 6.87 (dd, 1H); 6.69 (d, 2H); 4.61-4.49 (m, 1H); 4.28 (s, 2H); 2.25 (s, 3H); 1.83 (m, 2H); 1.74 (d, 2H); 1.59 (d, 1H); 1.39 (q, 2H); 1.09 (qd, 2H); 0.94 (qt, 1H).

N-Cyclohexyl-2-(4-methoxyphenoxy)-N-(3-thienyl)acetamide

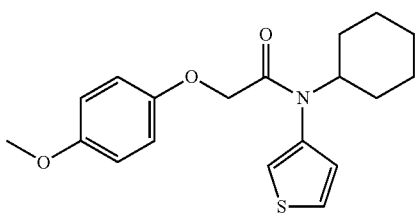 [SMILES: COc1ccc(OCC(=O)N(c2ccsc2)C2CCCCC2)cc1]

¹H NMR (500 MHz, CDCl₃) δ 7.38 (dd, 1H); 7.11 (dd, 1H); 6.87 (dd, 1H); 6.82-6.62 (m, 4H); 4.62-4.48 (m, 1H); 4.26 (s, 2H); 3.74 (s, 3H); 1.82 (d, 2H); 1.73 (d, 2H); 1.59 (d, 1H); 1.39 (qt, 2H); 1.09 (qd, 2H); 0.94 (qt, 1H).

134

(E)-3-(1,3-benzodioxol-5-yl)-N-(1H-pyrazol-3-yl)-N-(tetrahydrothiophen-2-ylmethyl)prop-2-enamide

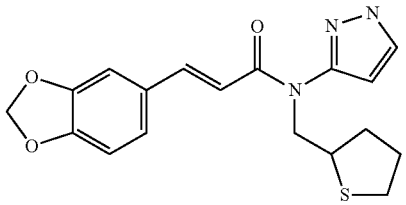 [SMILES: O=C(/C=C/c1ccc2c(c1)OCO2)N(CC1CCCS1)c1cc[nH]n1]

¹H NMR (500 MHz, CDCl₃) δ 7.68-7.54 (m, 2H); 6.89 (d, 1H); 6.81 (s, 1H); 6.74 (d, 1H); 6.31 (d, 1H); 6.24 (s, 1H); 5.96 (s, 2H); 4.29-4.17 (m, 1H); 3.67 (br s, 2H); 2.92 (dt, 1H); 2.81 (dt, 1H); 2.18-1.81 (m, 4H).

(E)-3-(p-Tolyl)-N-(1H-pyrazol-3-yl)-N-(tetrahydrothiophen-2-ylmethyl)prop-2-enamide The preparation is effected using N-(tetrahydrothiophen-2-ylmethyl)-1-(2-trimethylsilylethoxymethyl)pyrazole-3-amine and final deprotection with tetrabutylammonium fluoride in THF.

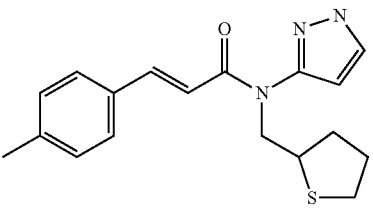 [SMILES: Cc1ccc(/C=C/C(=O)N(CC2CCCS2)c2cc[nH]n2)cc1]

¹H NMR (500 MHz, CDCl₃) δ 7.75-7.55 (m, 2H); 7.32-7.20 (m, 2H); 7.09 (d, 2H); 6.43 (d, 1H); 6.22 (s, 1H); 4.30-4.18 (m, 1H); 3.75-3.62 (m, 2H); 2.96-2.86 (m, 1H); 2.85-2.74 (m, 1H); 2.31 (s, 3H); 2.13-1.77 (m, 4H).

(E)-3-(4-methoxyphenyl)-N-(1H-pyrazol-3-yl)-N-(tetrahydrothiophen-2-ylmethyl)prop-2-enamide The preparation is effected using N-(tetrahydrothiophen-2-ylmethyl)-1-(2-trimethylsilylethoxymethyl)pyrazole-3-amine and final deprotection with tetrabutylammonium fluoride in THF.

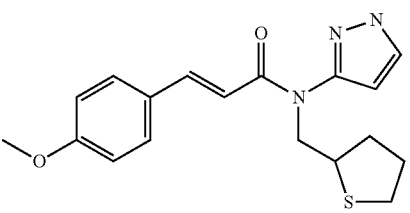 [SMILES: COc1ccc(/C=C/C(=O)N(CC2CCCS2)c2cc[nH]n2)cc1]

¹H NMR (500 MHz, CDCl₃) δ 7.73 (d, 1H); 7.65 (s, 1H); 7.32 (d, 2H); 6.84 (d, 2H); 6.38 (d 11H); 6.26 (s, 1H); 4.37-4.21 (m, 1H); 3.79 (s, 3H); 3.75-3.61 (m, 2H); 3.00-2.89 (m, 1H); 2.89-2.79 (m, 1H); 2.18-1.83 (m, 4H).

135

2-(4-Methylphenoxy)-N-(1H-pyrazol-3-yl)-N-(tetrahydrothiophen-2-ylmethyl)acetamide

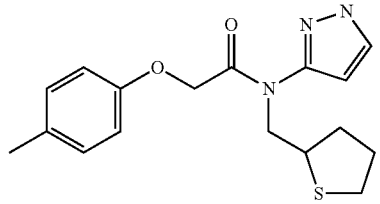 [SMILES: Cc1ccc(OCC(=O)N(CC2CCCS2)c2cc[nH]n2)cc1]

$^1$H NMR (500 MHz, CDCl$_3$) δ 7.57 (d, 1H); 7.00 (d, 2H); 6.71 (d, 2H); 6.24 (d, 1H); 4.55 (q, 2H); 4.18-4.04 (m, 1H); 3.68-3.50 (m, 2H); 2.93-2.67 (m, 2H); 2.23 (s, 3H); 2.08-1.80 (m, 4H).

2-(4-Methoxyphenoxy)-N-(1H-pyrazol-3-yl)-N-(tetrahydrothiophen-2-ylmethyl)acetamide

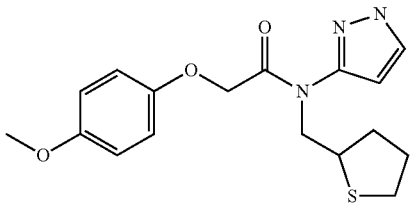 [SMILES: COc1ccc(OCC(=O)N(CC2CCCS2)c2cc[nH]n2)cc1]

$^1$H NMR (500 MHz, CDCl$_3$) δ 7.58 (d, 1H); 6.76 (s, 4H), 6.24 (d, 1H); 4.53 (q, 2H); 4.13 (q, 1H); 3.72 (s, 3H); 3.65-3.46 (m, 2H); 2.94-2.84 (m, 1H); 2.84-2.74 (m, 1H); 2.09-1.73 (m, 4H).

(E)-3-(p-Tolyl)-N-(1H-pyrazol-3-yl)-N-tetrahydrothiophen-3-ylprop-2-enamide

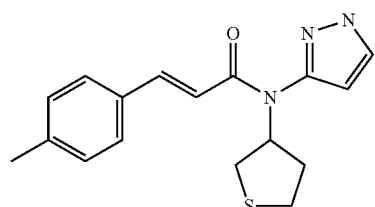

$^1$H NMR (500 MHz, CDCl$_3$) δ 7.76-7.56 (m, 2H); 7.21 (d, 2H); 7.07 (d, 2H); 6.24 (d, 1H); 6.17 (d, 1H); 5.37-5.22 (m, 1H); 3.10 (dd, 1H); 2.92-2.80 (m, 1H); 2.76 (t, 1H); 2.69 (ddd, 1H); 2.36-2.22 (m, 4H); 1.78 (qd, 1H).

136

(E)-3-(4-Methoxyphenyl)-N-(1H-pyrazol-3-yl)-N-tetrahydrothiophen-3-yl)prop-2-enamide

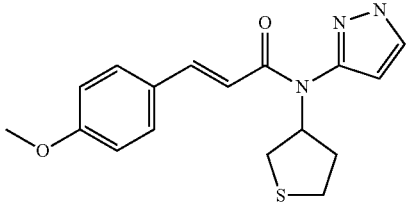 [SMILES: COc1ccc(/C=C/C(=O)N(c2cc[nH]n2)C2CCSC2)cc1]

$^1$H NMR (500 MHz, CDCl$_3$) δ 7.77-7.53 (m, 2H); 7.25 (d, 2H); 6.79 (d, 2H); 6.24 (d, 1H); 6.09 (d, 1H); 5.40-5.16 (m, 1H); 3.79 (s, 3H); 3.10 (dd, 1H); 2.92-2.82 (m, 1H); 2.76 (t, 1H); 2.75-2.65 (m, 1H); 2.31-2.22 (m, 1H); 1.85-1.70 (m, 1H).

2-(4-Methoxyphenoxy)-N-(1H-pyrazol-3-yl)-N-tetrahydrothiophen-3-ylacetamide

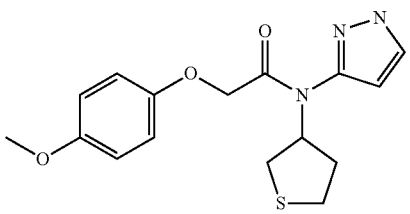 [SMILES: COc1ccc(OCC(=O)N(c2cc[nH]n2)C2CCSC2)cc1]

$^1$H NMR (500 MHz, CDCl$_3$) δ 7.62 (d, 1H); 6.76 (s, 4H); 6.23 (d, 1H); 5.25-5.14 (m, 1H); 4.35 (s, 2H); 3.73 (s, 3H); 3.07 (dd, 1H); 2.84 (dd, 1H); 2.78-2.59 (m, 2H); 2.34-2.15 (m, 1H); 1.84-1.70 (m, 1H).

(E)-3-(1,3-Benzodioxol-5-yl)-N,N-bis(2-pyridyl)prop-2-enamide

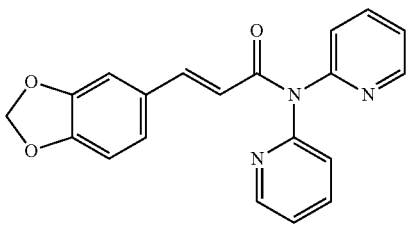 [SMILES: O=C(/C=C/c1ccc2c(c1)OCO2)N(c1ccccn1)c1ccccn1]

7.25-7.16 (m, 2H); 6.92 (d, 1H); 6.80 (s, 1H); 6.77 (d, 1H); 6.19 (d, 1H); 5.97 (s, 2H).

(E)-3-(1,3-benzodioxol-5-yl)-N-(1H-pyrazol-3-yl)-N-(tetrahydrofuran-2-ylmethyl)prop-2-enamide

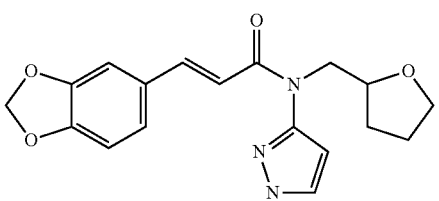 [SMILES: O=C(/C=C/c1ccc2c(c1)OCO2)N(CC1CCCO1)c1cc[nH]n1]

¹H NMR (400 MHz, chloroform-d) δ 7.61 (d, J=15.5 Hz, 1H), 7.57 (d, J=2.1 Hz, 1H), 6.90 (d, J=7.7 Hz, 1H), 6.83 (s, 1H), 6.74 (d, J=8.0 Hz, 1H), 6.42 (d, J=15.2 Hz, 1H), 6.21 (s, 1H), 5.95 (s, 2H), 4.22 (qd, J=7.2, 4.2 Hz, 1H), 4.13 (dd, J=13.8, 4.1 Hz, 1H), 3.95-3.84 (m, 1H), 3.78 (td, J=7.9, 6.2 Hz, 1H), 3.68-3.60 (m, 1H), 2.10-1.96 (m, 1H), 1.99-1.82 (m, 2H), 1.62 (ddt, J=15.6, 12.0, 8.1 Hz, 1H).

(E)-3-(p-tolyl)-N-(1H-pyrazol-3-yl)-N-(tetrahydrofuran-2-ylmethyl)prop-2-enamide

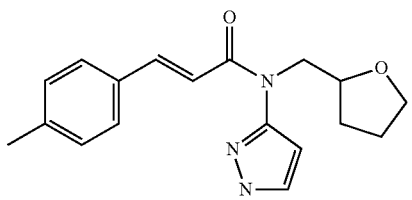 [SMILES: Cc1ccc(/C=C/C(=O)N(CC2CCCO2)c2cc[nH]n2)cc1]

¹H NMR (400 MHz, chloroform-d) δ 11.26 (s, 1H), 7.68 (d, J=15.5 Hz, 1H), 7.56 (d, J=2.2 Hz, 1H), 7.27 (d, J=8.0 Hz, 2H), 7.10 (d, J=7.8 Hz, 2H), 6.55 (d, J=15.6 Hz, 1H), 6.21 (s, 1H), 4.22 (qd, J=7.1, 4.1 Hz, 1H), 4.18-4.10 (m, 1H), 3.90 (dt, J=8.3, 6.8 Hz, 1H), 3.78 (td, J=7.9, 6.1 Hz, 1H), 3.73-3.57 (m, 1H), 2.32 (s, 3H), 2.12-1.96 (m, 1H), 1.98-1.80 (m, 2H), 1.61 (ddt, J=12.0, 8.4, 7.2 Hz, 1H).

(E)-3-(4-methoxyphenyl)-N-(1H-pyrazol-3-yl)-N-(tetrahydrofuran-2-ylmethyl)prop-2-enamide

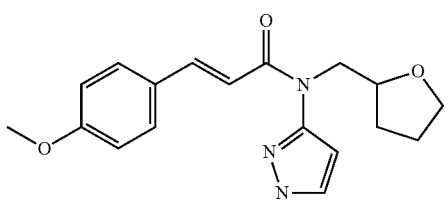 [SMILES: COc1ccc(/C=C/C(=O)N(CC2CCCO2)c2cc[nH]n2)cc1]

¹H NMR (600 MHz, chloroform-d) δ 8.15 (d, J=3.0 Hz, 1H), 7.90 (d, J=15.8 Hz, 1H), 7.63-7.61 (m, 2H), 7.62 (d, J=15.9 Hz, 1H), 6.93 (d, J=8.7 Hz, 2H), 5.92 (d, J=3.0 Hz, 1H), 4.14 (qd, J=7.1, 3.6 Hz, 1H), 3.97-3.87 (m, 1H), 3.85 (s, 3H), 3.83-3.73 (m, 1H), 3.57-3.47 (m, 1H), 3.32-3.25 (m, 1H), 2.04 (dddt, J=9.5, 8.4, 6.9, 4.9 Hz, 1H), 1.98-1.88 (m, 2H), 1.69 (ddt, J=12.1, 8.6, 7.1 Hz, 1H).

2-(4-methylphenoxy)-N-(1H-pyrazol-3-yl)-N-(tetrahydrofuran-2-ylmethyl)acetamide

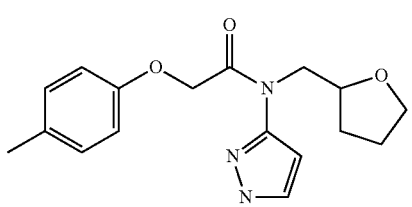 [SMILES: Cc1ccc(OCC(=O)N(CC2CCCO2)c2cc[nH]n2)cc1]

¹H NMR (400 MHz, chloroform-d) δ 7.54 (d, J=2.4 Hz, 1H), 7.01 (d, J=8.1 Hz, 2H), 6.72 (d, J=8.0 Hz, 2H), 6.28 (s, 1H), 4.66-4.48 (m, 2H), 4.2-4.1 (m, 1H), 4.0-3.9 (m, 1H), 3.9-3.8 (m, 1H), 3.8-3.7 (m, 1H), 3.64 (dd, J=13.6, 7.7 Hz, 1H), 2.24 (s, 3H), 2.03-1.78 (m, 3H), 1.66-1.52 (m, 1H).

(E)-3-(1,3-benzodioxol-5-yl)-N-(2-pyridyl)-N-(tetrahydrofuran-2-ylmethyl)prop-2-enamide

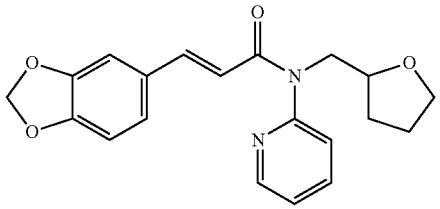 [SMILES: O=C(/C=C/c1ccc2c(c1)OCO2)N(CC1CCCO1)c1ccccn1]

¹H NMR (600 MHz, chloroform-d) δ 8.53 (ddd, J=4.9, 2.0, 0.8 Hz, 1H), 7.75 (ddd, J=8.1, 7.4, 2.0 Hz, 1H), 7.63 (d, J=15.3 Hz, 1H), 7.33 (dt, J=8.1, 1.0 Hz, 1H), 7.22 (ddd, J=7.4, 4.9, 1.0 Hz, 1H), 6.89 (dd, J=8.1, 1.6 Hz, 1H), 6.80 (d, J=1.7 Hz, 1H), 6.75 (d, J=8.0 Hz, 1H), 6.27 (d, J=15.3 Hz, 1H), 5.95 (s, 2H), 4.24-4.18 (m, 2H), 4.04-3.98 (m, 1H), 3.73 (ddd, J=8.3, 7.2, 6.5 Hz, 1H), 3.67 (td, J=8.0, 5.9 Hz, 1H), 1.99 (dddd, J=11.9, 8.6, 6.5, 5.2 Hz, 1H), 1.94-1.87 (m, 1H), 1.87-1.79 (m, 1H), 1.63 (ddt, J=12.2, 8.6, 6.9 Hz, 1H).

(E)-3-(p-tolyl)-N-(2-pyridyl)-N-(tetrahydrofuran-2-ylmethyl)prop-2-enamide

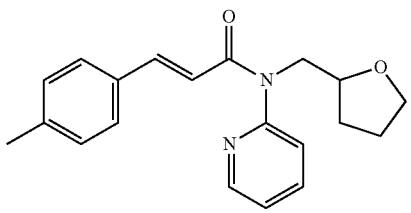 [SMILES: Cc1ccc(/C=C/C(=O)N(CC2CCCO2)c2ccccn2)cc1]

¹H NMR (600 MHz, chloroform-d) δ 8.53 (dt, J=4.8, 1.9, 0.7 Hz, 1H), 7.74 (td, J=7.7, 2.0 Hz, 1H), 7.69 (d, J=15.5 Hz, 1H), 7.32 (d, J=8.0 Hz, 1H), 7.25 (s, 2H), 7.22 (ddd, J=7.4, 4.9, 0.9 Hz, 1H), 7.11 (d, J=8.0 Hz, 2H), 6.40 (d, J=15.4 Hz, 1H), 4.25-4.21 (m, 2H), 4.05-3.99 (m, 1H), 3.77-3.70 (m, 1H), 3.67 (td, J=8.0, 6.0 Hz, 1H), 2.33 (s, 3H), 2.04-1.96 (m, 1H), 1.96-1.87 (m, 1H), 1.87-1.78 (m, 1H), 1.64 (ddt, J=12.3, 8.5, 7.0 Hz, 1H).

(E)-3-(4-methoxyphenyl)-N-(2-pyridyl)-N-(tetrahydrofuran-2-ylmethyl)prop-2-enamide

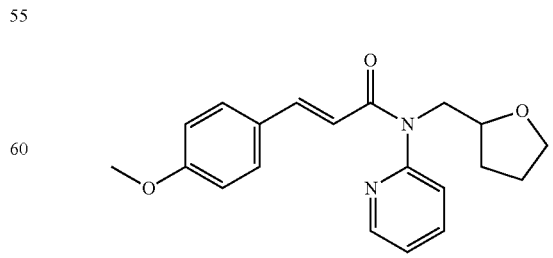

¹H NMR (400 MHz, chloroform-d) δ 8.53 (ddd, J=5.0, 2.0, 0.8 Hz, 1H), 7.74 (td, J=7.7, 2.0 Hz, 1H), 7.68 (d, J=15.4

Hz, 1H), 7.34 (dd, J=7.5, 1.0 Hz, 1H), 7.32-7.28 (m, 2H), 7.21 (ddd, J=7.4, 4.9, 1.0 Hz, 1H), 6.85-6.78 (m, 2H), 6.33 (d, J=15.4 Hz, 1H), 4.27-4.17 (m, 2H), 4.07-3.96 (m, 1H), 3.80 (s, 3H), 3.93-3.62 (m, 2H), 2.09-1.75 (m, 3H), 1.64 (ddt, J=11.6, 8.2, 6.7 Hz, 1H).

(E)-3-(1,3-benzodioxol-5-yl)-N-ethyl-N-(tetrahydrofuran-2-ylmethyl)prop-2-enamide

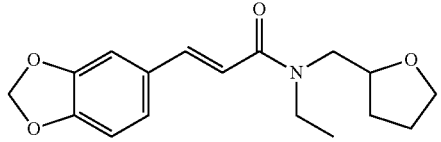 [SMILES: CCN(CC1CCCO1)C(=O)/C=C/c1ccc2c(c1)OCO2]

Two rotamers at the nitrogen are apparent in the spectrum. $^1$H NMR (400 MHz, chloroform-d) δ 7.66-7.55 (m, 2H), 7.06-6.95 (m, 4H), 6.81-6.74 (m, 3H), 6.70 (d, J=15.3 Hz, 1H), 5.98 (s, 4H), 4.17-4.02 (m, 2H), 3.93-3.82 (m, 3H), 3.82-3.69 (m, 2H), 3.69-3.56 (m, 4H), 3.56-3.42 (m, 2H), 3.20 (dd, J=13.8, 7.3 Hz, 1H), 2.08-1.97 (m, 2H), 1.97-1.79 (m, 3H), 1.63-1.52 (m, 3H), 1.23 (t, J=7.0 Hz, 3H), 1.18 (t, J=7.1 Hz, 3H).

N-ethyl-2-(4-methoxyphenoxy)-N-(tetrahydrofuran-2-ylmethyl)acetamide

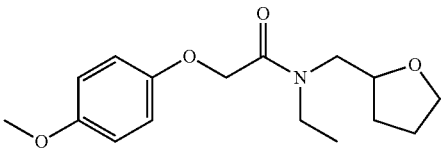 [SMILES: CCN(CC1CCCO1)C(=O)COc1ccc(OC)cc1]

Two rotamers at the nitrogen are apparent in the spectrum, $^1$H NMR (400 MHz, chloroform-d) δ 6.93-6.86 (m, 4H), 6.82 (dd, J=9.2, 1.7 Hz, 4H), 4.71 (dd, J=14.6, 1.3 Hz, 2H), 4.66 (dd, J=14.1, 1.0 Hz, 2H), 4.15-4.06 (m, 1H), 4.06-3.99 (m, 1H), 3.90-3.80 (m, 2H), 3.76 (s, 6H), 3.79-3.69 (m, 2H), 3.66-3.57 (m, 1H), 3.54 (q, J=7.1 Hz, 2H), 3.47-3.31 (m, 3H), 3.13 (dd, J=13.9, 7.5 Hz, 2H), 2.07-1.94 (m, 2H), 1.94-1.78 (m, 4H), 1.58-1.44 (m, 2H), 1.21 (t, J=7.1 Hz, 3H), 1.13 (t, J=7.1 Hz, 3H).

(E)-N-phenyl-3-(p-tolyl)-N-(tetrahydrofuran-2-ylmethyl)prop-2-enamide

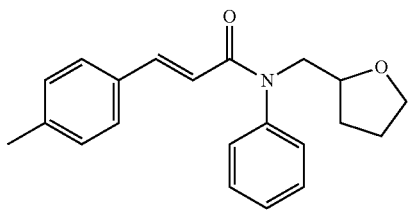 [SMILES: Cc1ccc(/C=C/C(=O)N(CC2CCCO2)c2ccccc2)cc1]

$^1$H NMR (400 MHz, chloroform-d) δ 7.65 (d, J=15.5 Hz, 1H), 7.45-7.38 (m, 2H), 7.38-7.33 (m, 1H), 7.33-7.28 (m, 2H), 7.18 (d, J=8.1 Hz, 2H), 7.06 (d, J=8.0 Hz, 2H), 6.26 (d, J=15.5 Hz, 1H), 4.21-4.14 (m, 1H), 4.01 (dd, J=13.7, 4.8 Hz, 1H), 3.88-3.69 (m, 3H), 2.30 (s, 3H), 2.02-1.78 (m, 3H), 1.67-1.56 (m, 1H).

(E)-3-(4-methoxyphenyl)-N-phenyl-N-(tetrahydrofuran-2-ylmethyl)prop-2-enamide

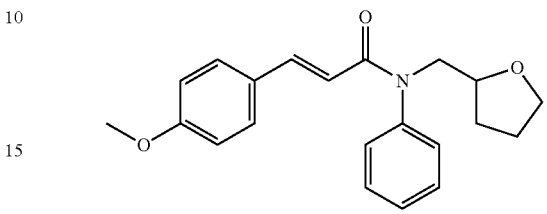

$^1$H NMR (400 MHz, chloroform-d) δ 7.63 (d, J=15.5 Hz, 1H), 7.46-7.39 (m, 2H), 7.38-7.32 (m, 1H), 7.32-7.28 (m, 2H), 7.27-7.21 (m, 2H), 6.79 (d, J=8.8 Hz, 2H), 6.17 (d, J=15.5 Hz, 1H), 4.17 (qd, J=6.8, 4.9 Hz, 1H), 4.02 (dd, J=13.6, 4.9 Hz, 1H), 3.88-3.80 (m, 1H), 3.82-3.75 (m, 1H), 3.78 (s, 3H), 3.73 (ddd, J=8.3, 7.4, 5.8 Hz, 1H), 2.06-1.94 (m, 1H), 2.03-1.78 (m, 2H), 1.68-1.56 (m, 1H).

2-(4-methylphenoxy)-N-phenyl-N-(tetrahydrofuran-2-ylmethyl)acetamide

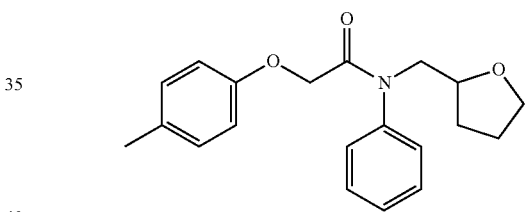

$^1$H NMR (400 MHz, chloroform-d) δ 7.43 (dd, J=8.2, 6.4 Hz, 2H), 7.41-7.35 (m, 1H), 7.34-7.29 (m, 2H), 7.01 (d, J=8.3 Hz, 2H), 6.72-6.64 (m, 2H), 4.36 (d, J=14.6 Hz, 1H), 4.31 (d, J=14.7 Hz, 1H), 4.12 (qd, J=6.6, 4.6 Hz, 1H), 3.89-3.78 (m, 2H), 3.72 (td, J=7.8, 5.9 Hz, 2H), 2.24 (s, 3H), 2.04-1.78 (m, 3H), 1.62-1.53 (m, 1H).

2-(4-methoxyphenoxy)-N-phenyl-N-(tetrahydrofuran-2-ylmethyl)acetamide

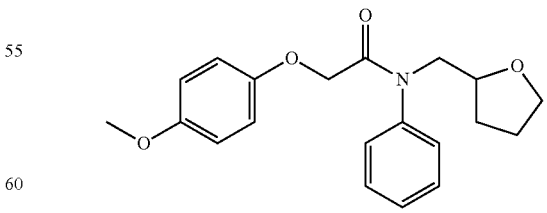

$^1$H NMR (400 MHz, chloroform-d) δ 7.47-7.40 (m, 2H), 7.40-7.34 (m, 1H), 7.34-7.28 (m, 2H), 6.77 (d, J=9.3 Hz, 2H), 6.72 (d, J=9.4 Hz, 2H), 4.38-4.24 (m, 2H), 4.17-4.06 (m, 1H), 3.88-3.78 (m, 2H), 3.78-3.69 (m, 2H), 3.73 (s, 3H), 2.05-1.77 (m, 3H), 1.64-1.53 (m, 1H).

(E)-3-(1,3-benzodioxol-5-yl)-N-ethyl-N-[2-(2-thienyl)ethyl]prop-2-enamide

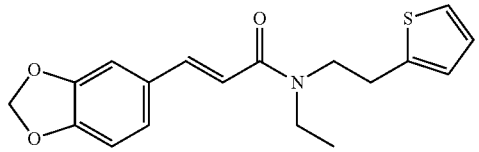 [SMILES: CCN(CCc1cccs1)C(=O)/C=C/c1ccc2c(c1)OCO2]

$^{1}$H NMR (400 MHz, chloroform-d) δ 7.65 (d, J=15.2 Hz, 1H), 7.54 (d, J=15.2 Hz, 1H), 7.18-7.10 (m, 2H), 7.06-6.98 (m, 2H), 6.97-6.89 (m, 4H), 6.88-6.83 (m, 2H), 6.79 (t, J=8.2 Hz, 2H), 6.66 (d, J=15.3 Hz, 1H), 6.44 (d, J=15.3 Hz, 1H), 5.98 (s, 4H), 3.66 (t, J=7.5 Hz, 4H), 3.50 (q, J=7.1 Hz, 2H), 3.37 (q, J=7.2 Hz, 2H), 3.19-3.09 (m, 4H), 1.19 (t, J=7.1 Hz, 6H).

Sensory Assessment:

Cooling Intensity of Inventive Amides Compared to FEMA 4809:

Test solutions with 2 or 20 ppm of the inventive amides in a 5% sugar solution were sensorily assessed by trained panelists (n=10 to 11) and compared with a solution containing 2 ppm of the comparative compound FEMA 4809. What were assessed here were initial cooling intensity, overall cooling intensity and long-lasting action on a scale from 1 (very weak) to 9 (very strong).

| # | Dosage ppm | Initial cooling effect | Overall cooling intensity | Long-lasting action |
|---|---|---|---|---|
| FEMA 4809 | 2 | 3.9 | 7.3 | 7.5 |
| (E)-3-(1,3-benzodioxol-5-yl)-N-phenyl-N-tetrahydrofuran-3-yl-prop-2-enamide | 20 | 5.8 | 7.8 | 7.9 |
| (E)-3-(1,3-benzodioxol-5-yl)-N-phenyl-N-tetrahydrofuran-3-yl-prop-2-enamide | 2 | 4.1 | 6.1 | 6.9 |
| (E)-N-phenyl-3-(p-tolyl)-N-tetrahydrofuran-3-yl-prop-2-enamide | 20 | 4.3 | 5.7 | 6.1 |
| (E)-3-(1,3-benzodioxol-5-yl)-N-(2-pyridyl)-N-tetrahydrothiophen-3-yl-prop-2-enamide | 20 | 6.6 | 8.3 | 7.9 |
| (E)-3-(p-tolyl)-N-(2-pyridyl)-N-tetrahydrothiophen-3-yl-prop-2-enamide | 20 | 5.3 | 7.0 | 7.4 |
| (E)-3-(4-methoxyphenyl)-N-(2-pyridyl)-N-tetrahydrothiophen-3-yl-prop-2-enamide | 20 | 4.1 | 5.6 | 5.9 |
| (E)-3-phenyl-N-(2-pyridyl)-N-tetrahydrothiophen-3-yl-prop-2-enamide | 20 | 5.3 | 7.8 | 7.8 |
| (E)-3-(1,3-benzodioxol-5-yl)-N-phenyl-N-(tetrahydrofuran-2-ylmethyl)prop-2-enamide | 20 | 3.1 | 5.0 | 5.3 |
| (E)-3-(1,3-benzodioxol-5-yl)-N-(2-methylsulfanylethyl)-N-phenyl-prop-2-enamide | 20 | 2.7 | 4.7 | 4.7 |
| 2-(4-methylphenoxy)-N-(2-methylsulfanylethyl)-N-phenyl-acetamide | 20 | 2.2 | 2.8 | 2.8 |
| (E)-3-(1,3-benzodioxol-5-yl)-N-ethyl-N-(2-methylsulfanylethyl)prop-2-enamide | 20 | 3.8 | 5 | 4.7 |
| (E)-3-(1,3-benzodioxol-5-yl)-N-(2-methylsulfanylethyl)-N-(2-pyridyl)prop-2-enamide | 20 | 6.2 | 7.8 | 7.5 |
| (E)-3-(1,3-benzodioxol-5-yl)-N-(2-methylsulfanylethyl)-N-(2-pyridyl)prop-2-enamide | 2 | 3.4 | 4.6 | 4.3 |
| (E)-N-(2-methylsulfanylethyl)-3-(p-tolyl)-N-(2-pyridyl)prop-2-enamide | 20 | 4 | 5.7 | 5.3 |
| (E)-3-(1,3-benzodioxol-5-yl)-N-(2-methylsulfanylethyl)-N-(1H-pyrazol-3-yl)prop-2-enamide | 20 | 3.7 | 6.6 | 6.6 |
| (E)-3-(1,3-benzodioxol-5-yl)-N-(2-methylsulfanylethyl)-N-(1H-pyrazol-3-yl)prop-2-enamide | 5 | 3.1 | 4.8 | 4.6 |

N.B.: The compounds were predissolved as a 1% ethanol solution.

What are clearly apparent are the faster onset of the cooling effect, a clear cooling profile comparable to or better than the reference, and the distinctly long-lasting cooling effect for inventive amides.

Time-Intensity Profile of Inventive Amides Compared to Reference Compounds (FEMA 4809, 4496) and WS3:

To establish a time-intensity profile, the oral cavity of trained panelists (n=8 to 11) was rinsed for 40 seconds with a mouthful of a sample solution (2 ppm of FEMA 4809 or 50 ppm of FEMA 4496 or 50 ppm of 1) to 5)). Subsequently, the cooling intensity perceived was assessed at defined time intervals using a scale.

| | Cooling intensity Time (sec.) | | | | | | | | | | | | | | |
|---|---|---|---|---|---|---|---|---|---|---|---|---|---|---|---|
| # | 0 | 40 | 70 | 100 | 130 | 160 | 190 | 220 | 250 | 280 | 310 | 340 | 640 | 940 | 1240 |
| FEMA 4809 | 0 | 2.7 | 2.8 | 2.5 | 2.6 | 2.6 | 2.7 | 2.8 | 2.7 | 2.8 | 2.9 | 2.8 | 2.6 | 2.6 | 2.1 |
| WS3 | 0 | 4.3 | 4.3 | 4.1 | 3.7 | 3.4 | 3.1 | 2.9 | 2.8 | 2.4 | 2.3 | 2.1 | 1.2 | 0.5 | 0.3 |
| FEMA 4496 | 0 | 1.9 | 2.3 | 2.4 | 2.3 | 2.3 | 2.3 | 2.2 | 2.2 | 2.2 | 2.1 | 2.1 | 2.0 | 1.5 | 1.2 |

-continued

| # | Cooling intensity Time (sec.) | | | | | | | | | | | | | | |
|---|---|---|---|---|---|---|---|---|---|---|---|---|---|---|---|
|   | 0 | 40 | 70 | 100 | 130 | 160 | 190 | 220 | 250 | 280 | 310 | 340 | 640 | 940 | 1240 |
| 1) | 0 | 6.1 | 6.4 | 6.4 | 6.2 | 6.0 | 6.0 | 5.8 | 5.7 | 5.5 | 5.4 | 5.3 | 4.8 | 3.9 | 2.9 |
| 2) | 0.0 | 4.2 | 4.5 | 4.5 | 4.5 | 4.4 | 4.3 | 4.2 | 4.1 | 4.1 | 3.9 | 3.8 | 3.1 | 2.1 | 1.1 |
| 3) | 0.0 | 4.0 | 4.0 | 4.0 | 3.9 | 3.7 | 3.7 | 3.5 | 3.4 | 3.3 | 3.2 | 3.2 | 2.2 | 1.3 | 0.7 |
| 4) | 0.0 | 4.7 | 4.6 | 4.5 | 4.3 | 4.2 | 3.9 | 3.7 | 3.5 | 3.3 | 3.2 | 2.9 | 2.0 | 1.3 | 1.1 |
| 5) | 0.0 | 5.7 | 6.2 | 6.0 | 5.6 | 5.6 | 5.2 | 5.0 | 4.9 | 4.6 | 4.5 | 4.3 | 3.1 | 1.9 | 1.1 |

1) (E)-3-(1,3-benzodioxol-5-yl)-N-phenyl-N-tetrahydrofuran-3-ylprop-2-enamide
2) (E)-3-(1,3-benzodioxol-5-yl)-N-(2-pyridyl)-N-tetrahydrothiophen-3-ylprop-2-enamide
3) (E)-3-(p-tolyl)-N-(2-pyridyl)-N-tetrahydrothiophen-3-ylprop-2-enamide
4) (E)-3-phenyl-N-(2-pyridyl)-N-tetrahydrothiophen-3-ylprop-2-enamide
5) (E)-3-(1,3-benzodioxol-5-yl)-N-(2-methylsulfanylethyl)-N-(2-pyridyl)prop-2-enamide For the inventive amides, distinctly more rapid or at least comparably rapid onset of cooling activity was found with respect to WS3. In addition, the cooling effect lasted for longer than for WS3 and for a comparatively long period to that for reference compounds (FEMA 4809, FEMA 4496), but these showed a distinctly retarded onset of the cooling action.

Use Examples

Toothpaste

Suitable toothpastes can be produced according to the following base formulation:

| % by weight | Ingredient type | Ingredient examples |
|---|---|---|
| 0.05-0.2% | Fluorides | sodium fluoride, tin(II) fluoride, sodium monofluorophosphate |
| 10-55% | Humectants | glycerol, sorbitol, propylene glycol, polyalkylene glycol |
| 0-50% | Polymer | polyoxyalkylene block copolymers Mw 5000-30 000 |
| 10-50% | Water | |
| 10-55% | Abrasives | calcium pyrophosphate, dicalcium phosphate, silicon oxide hydrate |
| 2-10% | Binder | karaya gum, tragacanth USP, sodium alginate, Irish moss, methyl cellulose |
| 2-8% | Surfactant | sodium lauryl sulfate, sodium-N-laurylsarcosinate, dioctylsodium sulfosuccinate, sodium lauryl sulfoacetate |
| 0-10% | Peroxygen compound | hydrogen peroxide, inorganic peroxides |
| 0.001-10% | TRPM8 agonist | |
| 0-10% s.o. | Further additives | |

Evaluation of the Progression of the Cooling Intensities of Compounds for Use in Accordance with the Invention Over Time in Illustrative Toothpaste:

The cooling substances for use in accordance with the invention were incorporated into toothpaste as follows:

| Deionized water | 27.52 |
|---|---|
| Sorbitol 700/0 | 45 |
| Solbrol M Na salt | 0.15 |
| Trisodium phosphate | 0.1 |
| Saccharin | 0.2 |
| Sodium monofluorophosphate | 1.12 |
| PEG 1500 | 5 |
| Sident 9 (abrasive silica) | 10 |
| Sident 22 S (thickening silica) | 8 |

-continued

| Sodium carboxymethyl cellulose | 0.9 |
|---|---|
| Titanium (IV) oxide | 0.5 |
| Sodium lauryl sulfate (SLS) | 1.5 |
| Respective cooling substance | 0.01 |
| Total | 100 |

All Figures in % by Weight

The sensory properties of the resulting toothpaste were evaluated by a trained panel (of 6 persons). For this purpose, the teeth were first cleaned with the toothpaste comprising the compounds of the invention for 30 seconds, then the toothpaste foam was spat out and the mouth was rinsed once with water. The testers assessed the intensity of the cold sensation on a scale from 0 (no cold sensation) to 9 (extremely strong cold sensation). The cold sensation was assessed after 30 seconds and after 1, 5, 10, 20, 30, 45 and 60 minutes.

Compounds of the invention tested by way of example were the compounds (E)-N-phenyl-3-(p-tolyl)-N-tetrahydrofuran-3-ylprop-2-enamide, (E)-3-(4-methoxyphenyl)-N-(2-pyridyl)-N-tetrahydrothiophen-3-ylprop-2-enamide, (E)-3-(1,3-benzodioxol-5-yl)-N-phenyl-N-(tetrahydrofuran-2-ylmethyl)prop-2-enamide, (E)-3-(1,3-benzodioxol-5-yl)-N-(2-methylsulfanylethyl)-N-phenylprop-2-enamide, 2-(4-methylphenoxy)-N-(2-methylsulfanylethyl)-N-phenylacetamide, (E)-3-(1,3-benzodioxol-5-yl)-N-ethyl-N-(2-methylsulfanylethyl)prop-2-enamide and (E)-N-(2-methylsulfanylethyl)-3-(p-tolyl)-N-(2-pyridyl)prop-2-enamide, but especially the compounds (E)-3-(1,3-benzodioxol-5-yl)-N-(2-pyridyl)-N-tetrahydrothiophen-3-ylprop-2-enamide, (E)-3-(1,3-benzodioxol-5-yl)-N-(2-methylsulfanylethyl)-N-(2-pyridyl)prop-2-enamide, (E)-3-(p-tolyl)-N-(2-pyridyl)-N-tetrahydrothiophen-3-ylprop-2-enamide, (E)-3-phenyl-N-(2-pyridyl)-N-tetrahydrothiophen-3-ylprop-2-enamide, (E)-3-(1,3-benzodioxol-5-yl)-N-phenyl-N-tetrahydrofuran-3-ylprop-2-enamide and (E)-3-(1,3-benzodioxol-5-yl)-N-(2-methylsulfanylethyl)-N-(1H-pyrazol-3-yl)prop-2-enamide.

By way of comparison, toothpastes with the same composition but comprising N-ethylmenthane-3-carboxamide ("WS 3", see also U.S. Pat. No. 4,150,052) as conventional cooling substance were tested.

The result showed that the cooling substances of the invention are distinctly superior to those used conventionally both in terms of rapidly perceptible intensity and in terms of duration of the perception of coolness. Thus, the cooling substances of the invention, even after 1 hour after the cleaning of the teeth, impart a very distinctly perceptible cold sensation, whereas this has already disappeared entirely after this time in the case of the conventional comparative compounds.

Chewing Gum

Suitable chewing gums can be produced according to the following base formulation:

| % by weight | Ingredient |
|---|---|
| 15-25% | Chewing gum base |
| 20-30% | Glucose syrup |
| 50-60% | Icing sugar |
| 0.001-10% | TRPM8 agonist |
| 1-2% | Softener (e.g. glycerol) |
| 3-6% | Water |

For "sugar-free formulations", it is also possible to replace the glucose syrup and the icing sugar with the sugar alcohols mannitol, xylitol and sorbitol, "Palatinit" and other synthetic sweeteners such as saccharin, cyclamate, acesulfame-K and aspartame.

Cosmetic Sunscreen Formulation

The formulations that follow describe a cosmetic sunscreen formulation comprising a combination of at least inorganic pigment and organic UV filter.

The formulations specified hereinafter are produced in a customary manner known to the person skilled in the art.

| | | |
|---|---|---|
| A | 7.50 Uvinul MC 80 | ethylhexyl cinnamate |
| | 2.00 Uvinul M 40 | benzophenone-3 |
| | 0.80 Rylo PG 11 | polyglyceryl dimer soyate |
| | 1.00 Span 60 | sorbitan stearate |
| | 0.50 Vitamin E acetate | tocopheryl acetate |
| | 3.00 Dracorin 100 SE | glyceryl stearate, PEG-100 stearate |
| | 1.00 Cremophor CO 410 | PEG-40-hydrogenated castor oil |
| B | 3.00 T-Lite SF | titanium dioxide, aluminum oxide hydrate, dimethicone/methicone copolymer |
| | 1.00 Cetiol SB 45 | *Butyrospermum parkii* (shea butter) |
| | 6.50 Finsolv TN | $C_{12-15}$-alkyl benzoate |
| C | 5.00 butylene glycol | butylene glycol |
| | 0.30 Keltrol | xanthan gum |
| | 0.10 Edeta BD | disodium EDTA |
| | 0.10 allantoin | allantoin |
| | 66.20 water dem, | aqua dem. |
| D | 1.00 Sepigel 305 | polyacrylamide, $C_{13-14}$ isoparaffin, Laureth-7 |
| | 0.001-10% TRPM8 agonist | |
| | q.s. | preservative |

Blancmange

Recipe (for 100 ml)

| Ingredient | Amount |
|---|---|
| Fat-free powdered milk | 10.715 g |
| Sucrose | 5 g |
| Novelose starch, National Starch | 7 g |
| Vegetable oil mixture | 2.2 g |
| Carrageenan | 0.016 g |
| Vanilla flavoring | 0.5 g |
| Sodium stearoyl-2-lactylate | 0.095 g |
| Yellow dye | 0.189 g |
| Magnesium phosphate | 0.165 g |
| Vitamin premix | 1.84 g |
| Trace element premix | 0.015 g |
| Active ingredient | 0.5 g |
| Water | 81.94 g |

Preparation:

Heat nine tenths of the water to 43.3° C. Dissolve skimmed milk powder in water. Heat oil to 60° C. and add carrageenan and oil-soluble vitamins to the oil. Mix oil into the product. Add the other constituents except for the modified starch, vanilla flavoring and vitamin premix. Homogenize the mixture. Add starch gradually. Add active ingredient, vitamins and flavoring. Standardize solids content. Heat in sterile units and pack in doses.

Textile Modification with Actives of the Invention

First of all, an aqueous slurry of amylose-containing starch is prepared by admixing 570 g of deionized water with 10 g of a standard commercial preservative. 20 g of carboxymethyl cellulose was dissolved therein, then 400 g of an amylose-containing starch having an amylose content of 50% by weight was added, and a slurry was produced while stirring.

This was followed by the production of aqueous liquors with amylose-containing starch by one of the following two methods:

Method 1: The respective slurry is adjusted to a starch content of 5% or 15% by weight by diluting with water.

Method 2: The respective slurry is first diluted with water to a starch content of 5% or 15% by weight and then admixed with 30 g/L of a 30% by weight aqueous polyurethane dispersion (nonionogenic).

This is followed by the modification of a woven fabric with amylose-containing starch and active of the invention.

Specimen woven cotton fabric with a basis weight of 124 g/m$^2$ is treated with one of the above-prepared liquors by means of a pad-mangle up to a liquor pickup of 80% by weight, based on the weight of the fabric. This is followed by drying at 120° C. for 2 min.

Subsequently, the fabric specimens thus modified are treated with an aqueous active formulation by applying an aqueous emulsion/suspension of an active of the invention having an active content of 1% to 7% by weight to the fabric specimen by means of a pad-mangle up to a liquor pickup of 79-80% by weight. Subsequently, the fabric specimens thus treated are dried in a domestic drier down to a residual moisture content of 15%.

The active-laden fabrics thus produced can then be examined further, for example for their cooling effect on contact with skin or the repellent effect thereof on insects.

Mouthwash Flavorings

Production of mouthwash flavorings with cooling action using the cooling substances of the invention:

The following were mixed (all figures, unless stated otherwise, in % by weight):

| | Batch | | |
|---|---|---|---|
| Component | a | b | c |
| Anethole | 30 | 30 | 30 |
| Eucalyptol | 25 | 25 | 25 |
| L-Menthol | 44.4 | 44.2 | 44.9 |
| (E)-3-(1,3-benzodioxol-5-yl)-N-phenyl-N-tetrahydrofuran-3-ylprop-2-enamide | 0.6 | | |
| (E)-N-phenyl-3-(p-tolyl)-N-tetrahydrofuran-3-ylprop-2-enamide | | 0.8 | |
| (E)-3-(1,3-benzodioxol-5-yl)-N-(2-pyridyl)-N-tetrahydrothiophen-3-yl-prop-2-enamide | | | 0.1 |
| Total | 100 | 100 | 100 |

The flavorings were each incorporated into a ready-to-use mouthwash at a concentration of 0.15% by weight, or into a mouthwash concentrate at a concentration of 3% by weight. Sensory assessment by a trained panel of experts showed that the flavorings led to rapid onset of a very long-lasting fresh effect that lasted over a period of almost 1 h after use of the mouthwashes.

Chewable Sweets

Production of a chewable sweet with cooling raspberry flavor using the cooling substances of the invention.

All figures, unless stated otherwise, in % by weight:

| Constituents | 1 | 2 | 3 | 4 | 5 | 6 |
|---|---|---|---|---|---|---|
| Water | 7.8 | 7.79 | 7.805 | 7.8 | 7.815 | 7.81 |
| C4 refined sugar | 42.1 | 42.1 | 42.1 | 42.1 | 42.1 | 42.1 |
| Dextrose 40 glucose syrup | 37.3 | 37.3 | 37.3 | 37.3 | 37.3 | 37.3 |
| Hydrogenated vegetable fat, melting point 32-36° C. | 6.6 | 6.6 | 6.6 | 6.6 | 6.6 | 6.6 |
| Lecithin emulsifier (soya lecithin) | 0.3 | 0.3 | 0.3 | 0.3 | 0.3 | 0.3 |
| Gelatin (pork gelatin) | 0.8 | 0.8 | 0.8 | 0.8 | 0.8 | 0.8 |
| Fondant type S30 | 4.8 | 4.8 | 4.8 | 4.8 | 4.8 | 4.8 |
| Raspberry flavoring | 0.22 | 0.22 | 0.22 | 0.22 | 0.22 | 0.22 |
| Menthyl lactate | 0.06 | 0.06 | 0.06 | 0.06 | 0.06 | 0.06 |
| (E)-3-(p-tolyl)-N-(2-pyridyl)-N-tetrahydrothiophen-3-ylprop-2-enamide | 0.02 | | | | | |
| (E)-3-(4-methoxyphenyl)-N-(2-pyridyl)-N-tetrahydrothiophen-3-yl-prop-2-enamide | | 0.03 | | | | |
| (E)-3-phenyl-N-(2-pyridyl)-N-tetrahydrothiophen-3-ylprop-2-enamide | | | 0.015 | | | |
| (E)-3-(1,3-benzodioxol-5-yl)-N-phenyl-N-(tetrahydrofuran-2-ylmethyl)prop-2-enamide | | | | 0.02 | | |
| (E)-3-(1,3-benzodioxol-5-yl)-N-(2-methylsulfanylethyl)-N-phenyl-prop-2-enamide | | | | | 0.005 | |
| 2-(4-methylphenoxy)-N-(2-methylsulfanylethyl)-N-phenyl-acetamide | | | | | | 0.01 |

Production Instructions:

a) allow gelatin to swell with water (1.8 times the amount of the gelatin) at 70° C. for 2 hours;

b) boil sugar, syrup, water, fat and lecithin at 123° C.;

c) mix gelatin solution gradually with the boiled mixture;

d) mix raspberry flavoring, menthyl lactate and the cooling substances of the invention and optionally stir in coloring;

e) bring the resulting mass to about 70° C. on a refrigerated table, then add fondant and aerate on a pulling machine for about 3 minutes;

f) then cut up the chewable sweet mixture and pack.

On consumption of the chewable sweets, a fresh, cooling raspberry flavor is perceived while chewing.

Fruit Gums

Production of fruit gums with a long-lasting fresh cooling taste using the cooling substances of the invention.

All figures, unless stated otherwise, in % by weight:

| Component | 1 | 2 | 3 | 4 | 5 | 6 |
|---|---|---|---|---|---|---|
| Water | 23.6 | 23.6 | 23.6 | 23.6 | 23.6 | 23.6 |
| Sucrose | 34.5 | 34.5 | 34.5 | 34.5 | 34.5 | 34.5 |
| Glucose syrup, DE 40 | 31.89 | 31.89 | 31.89 | 31.89 | 31.89 | 31.89 |
| Iso Syrup C* Tru Sweet 01750 (Cerestar GmbH) | 1.5 | 1.5 | 1.5 | 1.5 | 1.5 | 1.5 |
| Gelatin 240 Bloom | 8.2 | 8.2 | 8.2 | 8.2 | 8.2 | 8.2 |
| Yellow and red dye | 0.01 | 0.01 | 0.01 | 0.01 | 0.01 | 0.01 |
| Citric acid | 0.2 | 0.2 | 0.2 | 0.2 | 0.2 | 0.2 |
| (E)-3-phenyl-N-(2-pyridyl)-N-tetrahydrothiophen-3-ylprop-2-enamide | 0.1 | | | | | |
| (E)-3-(1,3-benzodioxol-5-yl)-N-phenyl-N-(tetrahydrofuran-2-ylmethyl)prop-2-enamide | | 0.1 | | | | |
| (E)-3-(1,3-benzodioxol-5-yl)-N-(2-methylsulfanylethyl)-N-phenyl-prop-2-enamide | | | 0.1 | | | |
| 2-(4-methylphenoxy)-N-(2-methylsulfanylethyl)-N-phenyl-acetamide | | | | 0.1 | | |
| (E)-3-(1,3-benzodioxol-5-yl)-N-phenyl-N-tetrahydrofuran-3-yl-prop-2-enamide | | | | | 0.1 | |
| (E)-N-phenyl-3-(p-tolyl)-N-tetrahydrofuran-3-ylprop-2-enamide | | | | | | 0.1 |

The above use examples can be applied to other products from the respective product group—if appropriate via modifications that the person skilled in the art will not find it difficult to undertake. It is not difficult for the person skilled in the art to see on the basis of the present description that the compounds of the invention—possibly with minor modifications—are mutually interchangeable without any great complexity. The concentration of the compound or mixture of the invention used is also variable as readily apparent to the person skilled in the art. Moreover, the product-specific further constituents in the respective use example, in a manner readily appreciable to the person skilled in the art, are likewise exchangeable for other product-typical constituents or can be supplemented thereby. A multitude of such product-specific constituents is disclosed in the description above.

The invention claimed is:

1. A compound selected from the group consisting of the following compounds:

| Structure | Name |
|---|---|
| 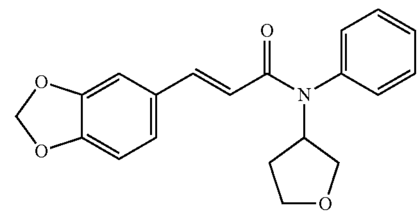 [SMILES: O=C(/C=C/c1ccc2c(c1)OCO2)N(c1ccccc1)C1CCOC1] | €-3-(1,3-benzodioxol-5-yl)-N-phenyl-N-tetrahydrofuran-3-yl-prop-2-enamide |
| 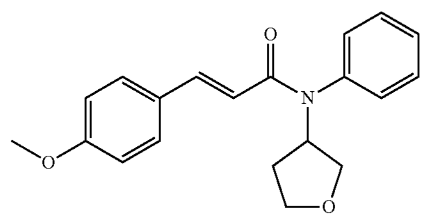 [SMILES: COc1ccc(/C=C/C(=O)N(c2ccccc2)C2CCOC2)cc1] | €-3-(4-methoxyphenyl)-N-phenyl-N-tetrahydrofuran-3-yl-prop-2-enamide |
| 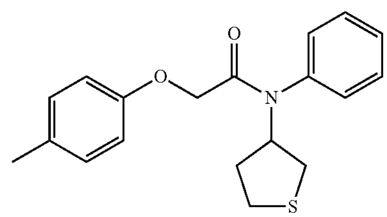 | 2-(4-methylphenoxy)-N-phenyl-N-tetrahydrothiophen-3-ylacetamide |
| 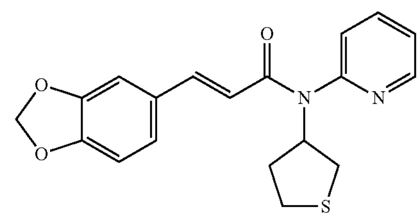 [SMILES: O=C(/C=C/c1ccc2c(c1)OCO2)N(c1ccccn1)C1CCSC1] | €-3-(1,3-benzodioxol-5-yl)-N-(2-pyridyl)-N-tetrahydrothiophen-3-yl-prop-2-enamide |
| 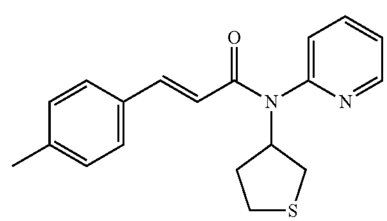 | €-3-(p-tolyl)-N-(2-pyridyl)-N-tetrahydrothiophen-3-ylprop-2-enamide |
| 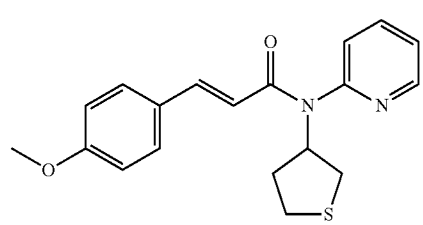 [SMILES: COc1ccc(/C=C/C(=O)N(c2ccccn2)C2CCSC2)cc1] | €-3-(4-methoxyphenyl)-N-(2-pyridyl)-N-tetrahydrothiophen-3-yl-prop-2-enamide |

| Structure | Name |
|---|---|
| 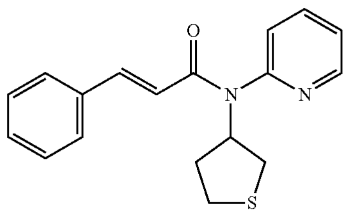 [SMILES: O=C(/C=C/c1ccccc1)N(c1ccccn1)C1CCSC1] | €-3-phenyl-N-(2-pyridyl)-N-tetrahydrothiophen-3-ylprop-2-enamide |
| 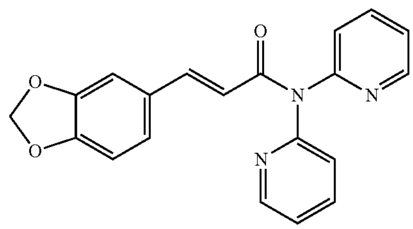 [SMILES: O=C(/C=C/c1ccc2c(c1)OCO2)N(c1ccccn1)c1ccccn1] | €-3-(1,3-benzodioxol-5-yl)-N,N-bis(2-pyridyl)prop-2-enamide |
| 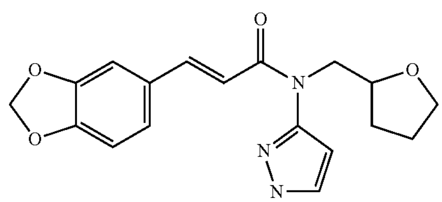 [SMILES: O=C(/C=C/c1ccc2c(c1)OCO2)N(CC1CCCO1)c1cc[nH]n1] | €-3-(1,3-benzodioxol-5-yl)-N-(1H-pyrazol-3-yl)-N-(tetrahydrofuran-2-ylmethyl)prop-2-enamide |
| 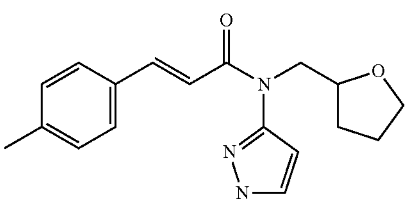 [SMILES: Cc1ccc(/C=C/C(=O)N(CC2CCCO2)c2cc[nH]n2)cc1] | €-3-(p-tolyl)-N-(1H-pyrazol-3-yl)-N-(tetrahydrofuran-2-ylmethyl)prop-2-enamide |
| 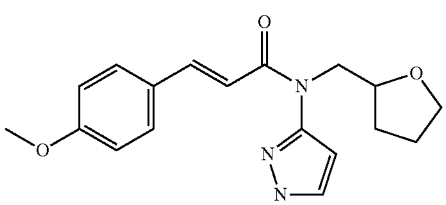 [SMILES: COc1ccc(/C=C/C(=O)N(CC2CCCO2)c2cc[nH]n2)cc1] | €-3-(4-methoxyphenyl)-N-(1H-pyrazol-3-yl)-N-(tetrahydrofuran-2-ylmethyl)prop-2-enamide |
| 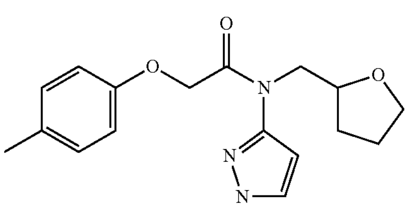 [SMILES: Cc1ccc(OCC(=O)N(CC2CCCO2)c2cc[nH]n2)cc1] | 2-(4-methylphenoxy)-N-(1H-pyrazol-3-yl)-N-(tetrahydrofuran-2-ylmethyl)acetamide |
| 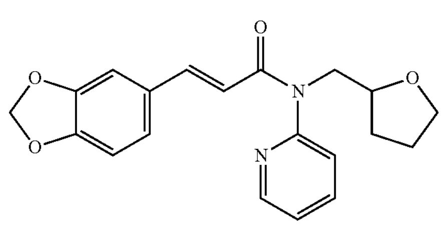 [SMILES: O=C(/C=C/c1ccc2c(c1)OCO2)N(CC1CCCO1)c1ccccn1] | €-3-(1,3-benzodioxol-5-yl)-N-(2-pyridyl)-N-(tetrahydrofuran-2-ylmethyl)prop-2-enamide |

| Structure | Name |
|---|---|
| 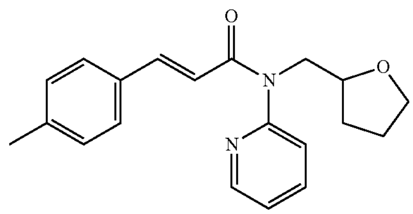 [SMILES: Cc1ccc(/C=C/C(=O)N(CC2CCCO2)c2ccccn2)cc1] | €-3-(p-tolyl)-N-(2-pyridyl)-N-(tetrahydrofuran-2-ylmethyl)prop-2-enamide |
| 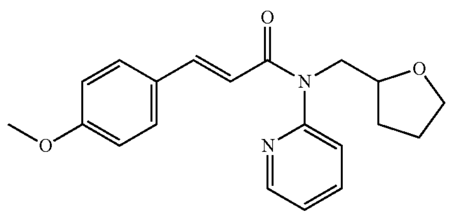 [SMILES: COc1ccc(/C=C/C(=O)N(CC2CCCO2)c2ccccn2)cc1] | €-3-(4-methoxyphenyl)-N-(2-pyridyl)-N-(tetrahydrofuran-2-ylmethyl)prop-2-enamide |
| 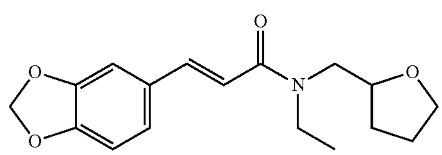 [SMILES: CCN(CC1CCCO1)C(=O)/C=C/c1ccc2c(c1)OCO2] | €-3-(1,3-benzodioxol-5-yl)-N-ethyl-N-(tetrahydrofuran-2-ylmethyl)prop-2-enamide |
| 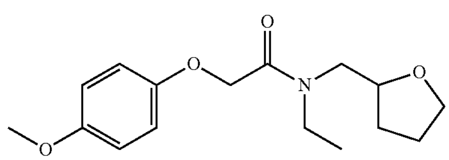 [SMILES: CCN(CC1CCCO1)C(=O)COc1ccc(OC)cc1] | N-ethyl-2-(4-methoxyphenoxy)-N-(tetrahydrofuran-2-ylmethyl)acetamide |
| 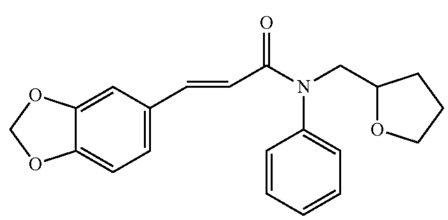 [SMILES: O=C(/C=C/c1ccc2c(c1)OCO2)N(CC1CCCO1)c1ccccc1] | €-3-(1,3-benzodioxol-5-yl)-N-phenyl-N-(tetrahydrofuran-2-ylmethyl)prop-2-enamide |
| 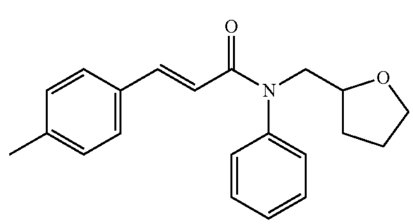 [SMILES: Cc1ccc(/C=C/C(=O)N(CC2CCCO2)c2ccccc2)cc1] | €-N-phenyl-3-(p-tolyl)-N-(tetrahydrofuran-2-ylmethyl)prop-2-enamide |
| 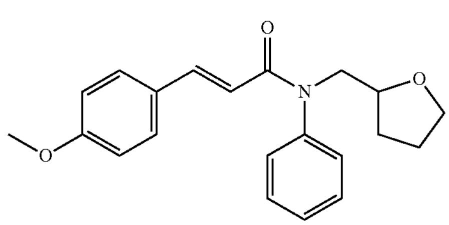 | €-3-(4-methoxyphenyl)-N-phenyl-N-(tetrahydrofuran-2-ylmethyl)prop-2-enamide |

-continued

| Structure | Name |
|---|---|
| 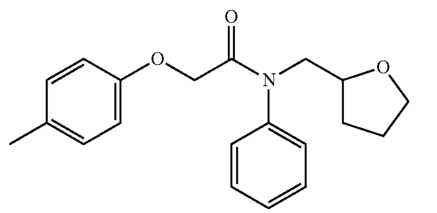 [SMILES: Cc1ccc(OCC(=O)N(CC2CCCO2)c2ccccc2)cc1] | 2-(4-methylphenoxy)-N-phenyl-N-(tetrahydrofuran-2-ylmethyl)acetamide |
| 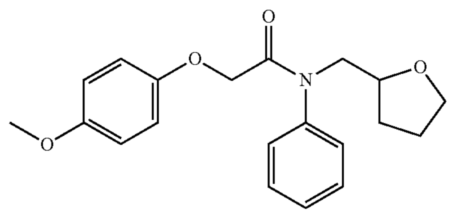 [SMILES: COc1ccc(OCC(=O)N(CC2CCCO2)c2ccccc2)cc1] | 2-(4-methoxyphenoxy)-N-phenyl-N-(tetrahydrofuran-2-ylmethyl)acetamide |
| 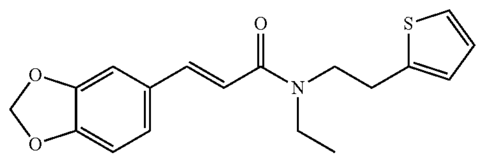 [SMILES: CCN(CCc1cccs1)C(=O)/C=C/c1ccc2c(c1)OCO2] | €-3-(1,3-benzodioxol-5-yl)-N-ethyl-N-[2-(2-thienyl)ethyl]prop-2-enamide |
| 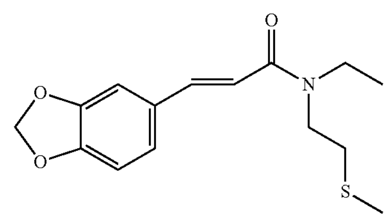 [SMILES: CCN(CCSC)C(=O)/C=C/c1ccc2c(c1)OCO2] | €-3-(1,3-benzodioxol-5-yl)-N-ethyl-N-(2-methylsulfanylethyl)prop-2-enamide |
| 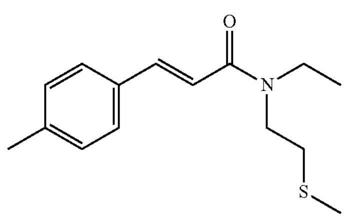 | €-N-ethyl-N-(2-methylsulfanylethyl)-3-(p-tolyl)prop-2-enamide |
| 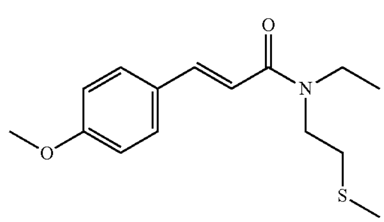 | €-N-ethyl-3-(4-methoxyphenyl)-N-(2-methylsulfanylethyl)prop-2-enamide |
| 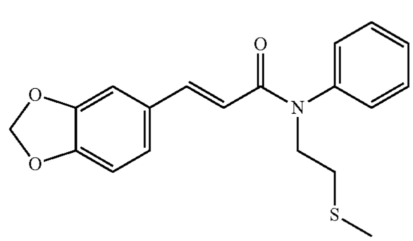 | €-3-(1,3-benzodioxol-5-yl)-N-(2-methylsulfanylethyl)-N-phenyl-prop-2-enamide |

-continued

| Structure | Name |
|---|---|
| 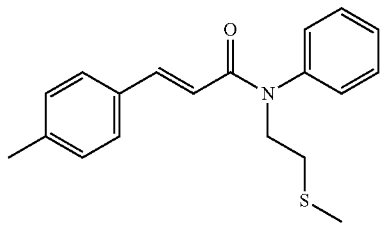 [SMILES: CSCCN(C(=O)/C=C/c1ccc(C)cc1)c1ccccc1] | €-N-(2-methylsulfanylethyl)-N-phenyl-3-(p-tolyl)prop-2-enamide |
| 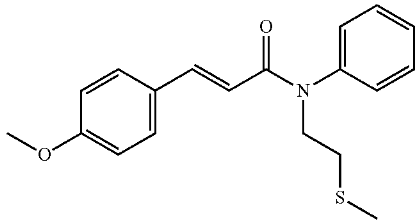 [SMILES: COc1ccc(/C=C/C(=O)N(CCSC)c2ccccc2)cc1] | €-3-(4-methoxyphenyl)-N-(2-methylsulfanylethyl)-N-phenyl-prop-2-enamide |
| 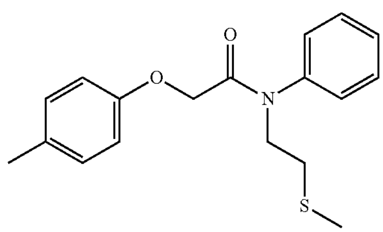 [SMILES: CSCCN(C(=O)COc1ccc(C)cc1)c1ccccc1] | 2-(4-methylphenoxy)-N-(2-methylsulfanylethyl)-N-phenyl-acetamide |
| 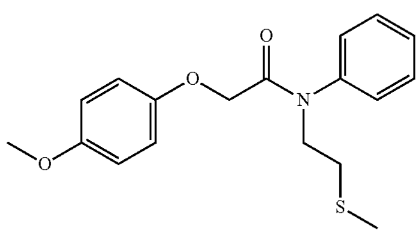 [SMILES: COc1ccc(OCC(=O)N(CCSC)c2ccccc2)cc1] | 2-(4-methoxyphenoxy)-N-(2-methylsulfanylethyl)-N-phenyl-acetamide |
| 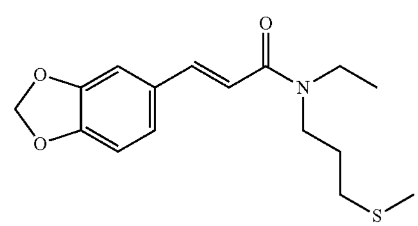 [SMILES: CCN(CCCSC)C(=O)/C=C/c1ccc2c(c1)OCO2] | €-3-(1,3-benzodioxol-5-yl)-N-ethyl-N-(3-methylsulfanylpropyl)prop-2-enamide |
| 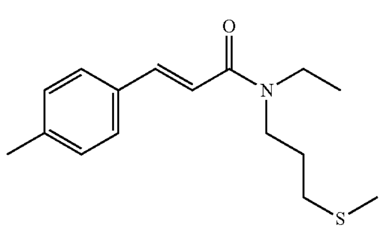 | €-N-ethyl-N-(3-methylsulfanylpropyl)-3-(p-tolyl)prop-2-enamide |

-continued

| Structure | Name |
|---|---|
| | E-3-(1,3-benzodioxol-5-yl)-N-(3-methylsulfanylpropyl)-N-phenyl-prop-2-enamide |
| | E-3-(1,3-benzodioxol-5-yl)-N-(2-methoxyethyl)-N-phenyl-prop-2-enamide |
| | E-3-(1,3-benzodioxol-5-yl)-N-(2-methylsulfanylethyl)-N-(2-pyridyl)prop-2-enamide |
| | E-N-(2-methylsulfanylethyl)-3-(p-tolyl)-N-(2-pyridyl)prop-2-enamide |
| | E-3-(4-methoxyphenyl)-N-(2-methylsulfanylethyl)-N-(2-pyridyl)prop-2-enamide |
| | 2-(4-methylphenoxy)-N-(2-methylsulfanylethyl)-N-(2-pyridyl)acetamide |

| Structure | Name |
|---|---|
| | E-3-(1,3-benzodioxol-5-yl)-N-(2-methylsulfanylethyl)-N-(1H-pyrazol-3-yl)prop-2-enamide |
| | E-N-(2-methylsulfanylethyl)-3-(p-tolyl)-N-(1H-pyrazol-3-yl)prop-2-enamide |
| 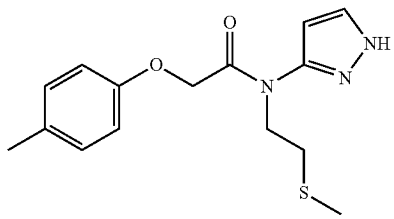 [SMILES: CSCCN(C(=O)COc1ccc(C)cc1)c1cc[nH]n1] | 2-(4-methylphenoxy)-N-(2-methylsulfanylethyl)-N-(1H-pyrazol-3-yl)acetamide or |
| 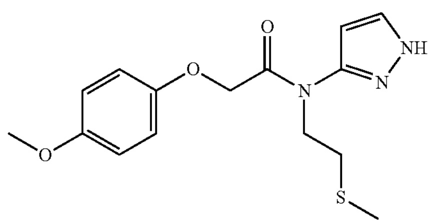 [SMILES: COc1ccc(OCC(=O)N(CCSC)c2cc[nH]n2)cc1] | 2-(4-methoxyphenoxy)-N-(2-methylsulfanylethyl)-N-(1H-pyrazol-3-yl)acetamide. |

2. A composition comprising the compound according to claim 1.

3. The composition according to claim 2, wherein the composition is selected from the group consisting of
   a) foods,
   b) oral care products,
   c) personal care products and
   d) foams and gels.

4. The composition according to claim 2, wherein the composition is selected from the group consisting of
   a) foods selected from the group consisting of ice cream, mousse, cream, drinks and confectionery,
   b) oral care products selected from the group consisting of toothpaste, mouthwash and chewing gum, and
   c) personal care products selected from the group consisting of skincare or haircare products.

5. The composition according to claim 2, wherein the composition is selected from the group consisting of aroma mixtures and formulations for nutrition, oral hygiene or cosmetic formulations, comprising one, two, three or more of the modulators wherein said modulator(s) is/are present in a (total) amount of 0.05 ppm to 10% by weight, based on the total weight of the aroma mixture or formulation.

6. The composition according to claim 2, wherein the composition additionally comprises:
   (1) one or more further substances having physiological cooling action, wherein the further substance or one, more than one or all of the further substances (i) cause(s) a flavoring effect or (ii) do(es) not cause a flavoring effect,
   and/or
   (2) one or more aromas with no physiological cooling effect, and/or
   (3) one or more substances having a trigeminal or mouthwatering effect with no physiological cooling effect,
   and/or
   (4) (iii) one compound or (iv) two or more compounds which, independently or collectively in case (iv), additionally cause(s) a flavor-modulating effect and/or a trigeminal and/or mouthwatering stimulus.

7. A composition comprising at least one compound as defined in claim 1 for use as a modulator of the TRPM8 receptor.

8. A non-therapeutic method of modulation of the cold menthol receptor TRPM8, which comprises contacting the receptor with at least one modulator selected from the group consisting of the compounds recited in claim 1,
   including salts of these compounds,
   and optionally the compounds in stereoisomerically pure form or mixtures of stereoisomers thereof.

9. The method according to claim 8, wherein the modulation is in vitro and/or in vivo modulation.

10. The method according to claim 8, wherein the receptor is contacted with at least one modulator which, in a cellular activity test using cells that recombinantly express the human TRPM8 receptor, modulates the permeability of these cells for $Ca^{2+}$ ions.

11. The method according to claim 8, wherein the modulator has an agonistic or antagonistic effect on cellular $Ca^{2+}$ ion permeability.

12. The method according to claim 8, wherein the modulator is a TRPM8 receptor agonist.

13. A process for non-therapeutic induction of a cold sensation in man and/or animals which comprises a modulator has an agonistic or antagonistic effect on cellular $Ca^{2+}$ ion permeability, wherein the modulator is selected from the compounds recited in claim 1.

14. The process according to claim 13 for non-therapeutic induction of a cold sensation by means of a packing or textile comprising the modulator.

15. The process according to claim 13, wherein a composition comprising at least one, two, three or more of the modulators in a (total) amount of 0.1 ppm to 10% by weight, based on the total weight of the composition, is used to achieve a cooling effect on the skin or mucosa that has been prolonged compared to the cooling effect of a composition of the same constitution in which the modulator(s) has/have merely been exchanged for N-ethylmenthanecarboxamide in the same concentration, by at least 10 minutes, and/or a cooling effect that sets in earlier compared to the cooling effect of a composition of the same constitution in which the modulator(s) has/have merely been exchanged for FEMA 4809 or FEMA 4496 in the same concentration.

16. A process for non-therapeutic induction of a cold sensation in man and/or animals for achieving a physiological cooling effect on the skin and/or mucosa that has been prolonged by at least 10 minutes compared to the cooling effect of a composition of the same constitution in which the modulator(s) has/have merely been exchanged for N-ethylmenthanecarboxamide in the same concentration, and/or a cooling effect that sets in earlier compared to the cooling effect of a composition of the same constitution in which the modulator(s) has/have merely been exchanged for FEMA 4809 or FEMA 4496 in the same concentration, comprising the following step:

applying an amount of a composition as defined in claim 2 which is sufficient for achieving a physiological cooling effect to the skin and/or mucosa.

\* \* \* \* \*